United States Patent
Bethell et al.

(10) Patent No.: US 10,822,360 B2
(45) Date of Patent: Nov. 3, 2020

(54) DIOXOLANE ANALOGUES OF URIDINE FOR THE TREATMENT OF CANCER

(71) Applicant: MEDIVIR AB, Stockholm (SE)

(72) Inventors: Richard Bethell, Huddinge (SE);
Anders Eneroth, Huddinge (SE);
Bjorn Klasson, Huddinge (SE);
Fredrik Oberg, Huddinge (SE)

(73) Assignee: MEDIVIR AB, Stockholm (SE)

( * ) Notice: Subject to any disclaimer, the term of this patent is extended or adjusted under 35 U.S.C. 154(b) by 0 days.

(21) Appl. No.: 16/847,477

(22) Filed: Apr. 13, 2020

(65) Prior Publication Data

US 2020/0239502 A1    Jul. 30, 2020

Related U.S. Application Data

(63) Continuation of application No. 16/459,165, filed on Jul. 1, 2019, now Pat. No. 10,654,877, which is a continuation of application No. 16/208,083, filed on Dec. 3, 2018, now Pat. No. 10,336,780, which is a continuation of application No. 15/506,692, filed as application No. PCT/EP2015/069370 on Aug. 24, 2015, now Pat. No. 10,144,750.

(30) Foreign Application Priority Data

Aug. 25, 2014  (SE) ........................ 1450983
Jun. 22, 2015  (SE) ........................ 1550858

(51) Int. Cl.

| C07D 405/04 | (2006.01) |
| C07F 9/6558 | (2006.01) |
| C07F 9/24 | (2006.01) |
| A61K 45/06 | (2006.01) |
| A61K 31/675 | (2006.01) |
| A61K 31/506 | (2006.01) |

(52) U.S. Cl.
CPC ........ *C07F 9/65586* (2013.01); *A61K 31/506* (2013.01); *A61K 31/675* (2013.01); *A61K 45/06* (2013.01); *C07D 405/04* (2013.01); *C07F 9/24* (2013.01)

(58) Field of Classification Search
CPC ........ C07D 405/04; C07F 9/24; A61K 31/506
USPC .................... 544/243, 309, 317; 514/86, 274
See application file for complete search history.

(56) References Cited

U.S. PATENT DOCUMENTS

| 10,144,750 B2 | 12/2018 | Bethell et al. |
| 10,336,780 B2 | 7/2019 | Bethell et al. |
| 10,654,877 B2 * | 5/2020 | Bethell ................. A61K 31/675 |
| 2013/0143835 A1 | 6/2013 | Eneroth et al. |

FOREIGN PATENT DOCUMENTS

| WO | 1998020879 A1 | 5/1998 |
| WO | 2002030922 A2 | 4/2002 |
| WO | 2005012327 A2 | 2/2005 |
| WO | 2005012327 A3 | 4/2005 |
| WO | 2008048128 A1 | 4/2008 |
| WO | 2008030373 A3 | 6/2008 |
| WO | 2015081133 A2 | 6/2015 |

OTHER PUBLICATIONS

Balzarini J. et al., Anti-HIV and Anti-HBV Activity and Resistance Profile of 2',3'-Dideoxy-3'-Thiacytidine (3TC) and Its Arylphosphoramidate Derivative CF 1109, Biochemical and Biophysical Research Communication , 1996, 225:363-369.
European Search Report dated Oct. 9, 2019.
Gura et al., Systems for identifying new drugs are often faulty, Science, 278:1041-1042, 1997.
International Search Report dated Oct. 15, 2015.
Johnson et al., Relationships between drug activity in NCI preclinical in vitro and in vivo models and early clinical trials, British Journal of Cancer, 84 (10):1424-1431, 2001.
Kulik, K. et al., Synthesis and an antiviral activity evluation of nucleoside 5'-O-(N-acyl) phosphoramidates, Antiviral Chemistry & Chemotherapy, 2011, 21:143-150.
Pearce et al., Failure modes in anticancer drug discovery and development, Cancer Drug Design and Discovery Edited by Stephen Neidle, Chapter 18, 99. 424-435, 2008.
Simone, Oncology: Introduction, Cecil Textbook of Medicine, 20th Edition, vol. 1, pp. 1004-101 O, 1995.

* cited by examiner

*Primary Examiner* — Deepak R Rao
(74) *Attorney, Agent, or Firm* — Gorman IP Law, IPC

(57) ABSTRACT

The invention provides compounds of the formula:

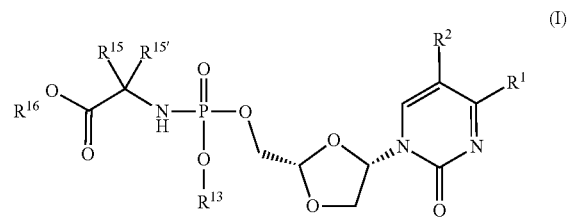

$R^1$ is $OR^{11}$, or $NR^5R^{5'}$;
$R^2$ is H or F;
$R^5$ is H, $C_1$-$C_6$alkyl, OH, $C(=O)R^6$, $O(C=O)R^6$ or $O(C=O)OR^6$;
$R^{5'}$ is H or $C_1$-$C_6$alkyl;
$R^6$ is $C_1$-$C_6$alkyl or $C_3$-$C_7$cycloalkyl;
$R^{13}$ is H, phenyl, pyridyl, benzyl, indolyl or naphthyl wherein the phenyl, pyridyl, benzyl, indolyl and naphthyl is optionally substituted with 1, 2 or 3 $R^{22}$;
and the other variables are as defined in the claims, which are of use in the treatment of cancer, and related aspects.

13 Claims, No Drawings

DIOXOLANE ANALOGUES OF URIDINE FOR THE TREATMENT OF CANCER

This Nonprovisional application is a Continuation application of co-pending application Ser. No. 16/459,165 which was filed on Jul. 1, 2019, which is a Continuation application of application Ser. No. 16/208,083, now U.S. Pat. No. 10,336,780, which was filed on Dec. 3, 2018, which is a Continuation of application Ser. No. 15/506,692 filed on Feb. 24, 2017, now U.S. Pat. No. 10,144,750, which is the National Phase Under 35 USC § 371 of PCT International Application No. PCT/EP2015/069370 filed on Aug. 24, 2015, which claims priority under 35 U.S.C. § 119 on Patent Application No. 1450983-0 filed in Sweden on Aug. 25, 2014, and Patent Application No. 1550858-3 filed in Sweden on Jun. 22, 2015, the entire contents of each of which are hereby incorporated by reference.

TECHNICAL FIELD

The present invention relates to phosphorus prodrugs of troxacitabine and derivatives thereof which are useful in the treatment of cancers, in particular liver cancer such as hepatocellular carcinoma (HCC) and secondary liver cancers. The invention further relates to compositions and combinations comprising these compounds, and methods for their use in the treatment of cancers, particularly liver cancer such as HCC.

BACKGROUND TO THE INVENTION

Primary liver cancer is the sixth most frequent cancer globally and the second leading cause of cancer death. The most frequent liver cancer, accounting for approximately 85% of all primary malignant liver cancers and has a rising incidence, is hepatocellular carcinoma (HCC), which is formed by hepatocytes that become malignant. Another type of cancer formed by hepatocytes is hepatoblastoma, a rare malignant tumour that primarily develops in children, and accounts for approximately 1% of all cancers in children and 79% of all primary liver cancers under the age of 15. Secondary liver cancer, or metastasis in the liver, is a cancer that starts somewhere else in the body and then spreads to the liver. Examples of secondary liver cancer includes many common types of cancer, such as colon, rectum, lung, and breast cancer. Liver cancer can also form from other structures within the liver such as the bile duct, blood vessels and immune cells. Cancer of the bile duct (cholangiocarcinoma and cholangiocellular cystadenocarcinoma) account for approximately 6% of primary liver cancers.

While surgical resection and liver transplantation are potentially curative therapies for early stage HCC, more than 20% of the patients will eventually relapse or encounter further problems, and the majority of HCC diagnosis take place at a stage that is too advanced for these treatments. Regional therapies, such as radiofrequency ablation are associated with response rates above 60%, but they are only suitable for a certain proportion of patients and are not always curative. Chemotherapy used so far has been minimally effective in HCC and to date response rates have not exceeded 25%. At present, sorafenib is the only effective drug on the market for the treatment of advanced or unresectable HCC, therefore, there is a great need for further treatments of HCC to reduce relapse rates and increase overall survival rates.

Many nucleoside analogues have been found to possess anticancer activity and they constitute a major class of chemotherapeutic agents that are widely used for the treatment of patients with cancer. This group of agents, known as antimetabolites, includes a variety of pyrimidine and purine nucleoside derivatives with cytotoxic activity.

Cellular nucleotide kinases phosphorylate nucleosides to their corresponding 5'-monophosphates which are further converted into their diphosphate and subsequently to the pharmacologically active triphosphate. It is known that some nucleosides are weakly active because they cannot be efficiently phosphorylated by kinases or are not substrates for kinases at all. In the phosphorylation sequence, the first phosphorylation of nucleoside analogues is rate limiting whereas the second and third phosphorylations are less sensitive to modifications to the nucleoside. Nucleoside monophosphates (nucleotides) per se are generally unstable in blood and show poor membrane permeation and hence are not suitable for use as drugs. Due to the high instability and poor cellular permeation of triphosphate of nucleosides and nucleoside analogues they cannot either be considered as possible drug candidates.

Troxacitabine, (beta-L-dioxolane cytidine) is a cytotoxic deoxycytidine analogue with an unnatural L-configuration which has demonstrated broad activity against both solid and hematopoietic malignancies in vitro and in vivo. Particularly, impressive activity has been observed against human cancer cell lines and xenografts of hepatocellular, prostate, and renal origin (Cancer Res., 55, 3008-3011, 1995). Troxacitabine has shown to give rise to a mutation of the kinase deoxycytidine kinase (dCK) which is normally responsible for the first phosphorylation step of the nucleoside, leading to no or very low levels of troxacitabine monophosphate, thereby leading to resistance.

Troxacitabine entered phase III clinical trials in 2008 in the acute myologenous leukemia indication, but did not proceed to registration. Discontinued phase II trials with troxacitabine include breast cancer, colorectal cancer, pancreatic cancer, melanoma, NSCLC, renal, prostate and ovarian tumours. Troxacitabine was generally administered as an intravenous infusion, thereby exposing many tissues to the drug, irrespective of the site of the cancer.

It has been shown that troxacitabine, despite its hydrophilic character, is transported into cells by passive diffusion, but is only very slowly accumulated in cancer cells in comparison with other, carrier transported nucleosides.

In WO2008/030373 derivatives of troxacitabine carrying a prodrug group on the cytosine base moiety are disclosed and the relationship between the lipophilicity of the prodrugs and their antitumor activity is evaluated. The patent states that base modification is desirable to avoid esterase difficulties with 5'-OH modification.

Phosphoramidate prodrugs at the 5' hydroxyl function of D-nucleosides have been successfully employed in antiviral drugs, such as sofosbuvir used in the treatment of HCV infection.

Unmasking of the sofosbuvir prodrug to reveal the monophosphate intracellularly is a complex, multistep process involving several hydrolase enzymes in a particular sequence.

The use of phosphoramidate prodrugs on cancer nucleosides has been less successful. Nucana is developing Acelerin (Nuc-1031), a phosphoramidate prodrug of the D-nucleoside gemcitabine for the treatment of pancreatic cancer (for structure: see page 71 of WO2005012327). However, even though the phosphoramidate would be thought to enhance lipophilicity and cell permeability of the compound, the Acelarin prodrug must still be administered as an IV infusion, thus exposing many healthy tissues to the cytotoxic metabolite.

There is even less experience with monophosphate prodrugs of L-nucleosides such as troxacitabine. WO2008048128 discloses a small number of troxacitabine monophosphate prodrugs including the compound at Example 14:

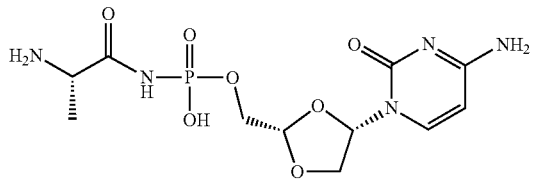 [SMILES: C[C@H](N)C(=O)NP(=O)(O)OC[C@H]1OC[C@@H](n2ccc(N)nc2=O)O1]

No cancer or other biological activity is disclosed for any of the compounds, either in the WO2008048128 specification or elsewhere in the academic literature. There are no reports of such a prodrug entering clinical trials. However, the inventors of WO2008048128 have published broadly similar prodrugs on the D-nucleoside gemcitabine (Baraniak et al Biorg Med Chem 2014 2133-2040) where the prodrug approach appears to work in certain tissues, and the D-nucleoside azidothymidine (Kulic et al Antivir Chem Chemother 2011 21(3) 143-150) where the prodrugs were 2-20 times less potent than the corresponding parent nucleoside. Kulic speculates that the azidothymidine prodrugs tended to be first dephosphorylated to the nucleoside and only then phosphorylated to the active triphosphate species. In that the prodrug approach works on gemcitabine (which resembles RNA by virtue of its substituted 2' function), and does not work on azidothymidine (which is 2'-deoxy thereby resembling DNA), it is hypothesised that the WO2008048128 prodrugs of troxacitabine (which is a DNA analog, albeit L-DNA), are likely to be inactive, like the azidothymidine prodrugs.

Balzarini et al Biochem Biophys Res Comm 225, 363-369 (1996) describe the HIV and HBV activity of CF 1109, a phosphoramidate prodrug of the L-nucleoside lamivudine/3TC, having the structure:

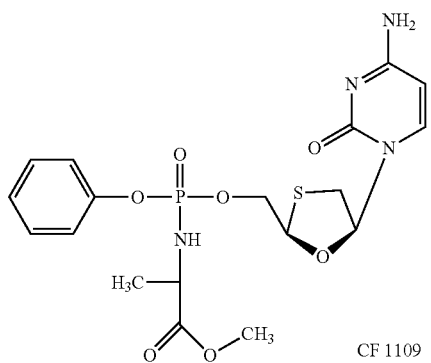 [SMILES: COC(=O)C(C)NP(=O)(OC[C@@H]1O[C@H](n2ccc(N)nc2=O)CS1)Oc1ccccc1]

CF 1109

Balzarini states that this phosphoramidate prodrug was ~250 fold less active against HIV than its parent nucleoside 3TC, but that the prodrug as "virtually equally effective against HBV in Hep G2.2.15 cells". In other words, addition of this large, phosphoramidate methyl ester prodrug, group did not improve antiviral potency in a liver cell line. Balzarini did not assay whether the prodrug was being metabolized to 3TC prior to being phosphorylated to the active triphosphate.

The present invention provides phosphorus prodrugs of troxacitabine, particularly liver targeted prodrugs such as phosphoramidates, which are suitable for oral administration. These prodrugs have the advantage of improved cell permeability due to increased lipophilicity compared to troxacitabine per se, and to more efficient form the active triphosphate due to bypassing the rate limiting first phosphorylation step. Further, the compounds of the invention are primarily metabolised to the active triphosphate in the liver thereby providing a high concentration of active compound in the target organ and at the same time keeping side effects due to toxicity in other organs to a minimum.

DESCRIPTION OF THE INVENTION

In one aspect, the present invention provides compounds represented by Formula (I):

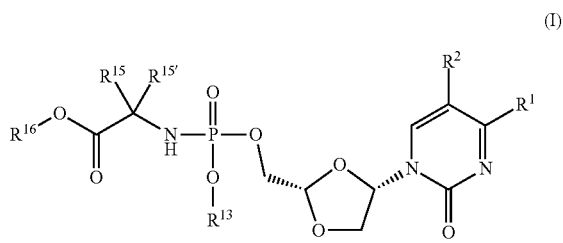

wherein:
$R^1$ is $OR^{11}$, or $NR^5R^{5'}$;
$R^2$ is H or F;
$R^5$ is H, $C_1$-$C_6$alkyl, OH, $C(=O)R^6$, $O(C=O)R^6$ or $O(C=O)OR^6$;
$R^{5'}$ is H or $C_1$-$C_6$alkyl;
$R^6$ is $C_1$-$C_{22}$alkyl or $C_3$-$C_7$cycloalkyl;
$R^{11}$ is H or $C_1$-$C_6$alkyl;
$R^{13}$ is H, phenyl, pyridyl, benzyl, indolyl or naphthyl wherein the phenyl, pyridyl, benzyl, indolyl and naphthyl is optionally substituted with 1, 2 or 3 $R^{22}$;
$R^{15}$ is H, $C_1$-$C_6$alkyl, $C_3$-$C_7$cycloalkyl, $C_3$-$C_7$cycloalkylC$_1$-C$_3$alkyl, phenyl, benzyl or indolyl;
$R^{15'}$ is H or $C_1$-$C_6$alkyl; or
$R^{15}$ and $R^{15'}$ together with the carbon atom to which they are attached from a $C_3$-$C_7$cycloalkylene group, wherein each $C_1$-$C_6$alkyl is optionally substituted with a group selected from halo, $OR^{18}$ and $SR^{18}$, and each $C_3$-$C_7$cycloalkyl, $C_3$-$C_7$cycloalkylene, phenyl and benzyl is optionally substituted with one or two groups independently selected from $C_1$-$C_3$alkyl, halo and $OR^{18}$;
$R^{16}$ is H, $C_1$-$C_{10}$alkyl, $C_2$-$C_{10}$alkenyl, $C_3$-$C_7$cycoalkyl, $C_3$-$C_7$cycloalkylC$_1$-C$_3$alkyl, benzyl, or phenyl, any of which is optionally substituted with 1, 2 or 3 groups, each independently selected from halo, $OR^{18}$ and $N(R^{18})_2$;
each $R^{18}$ is independently H, $C_1$-$C_6$alkyl, $C_1$-$C_6$haloalkyl or $C_3$-$C_7$cycloalkyl;
each $R^{22}$ is independently selected from halo, $C_1$-$C_6$alkyl, $C_1$-$C_6$alkenyl, $C_1$-$C_6$haloalkyl, $C_1$-$C_6$alkoxy, $C_1$-$C_6$haloalkoxy, phenyl, hydroxyC$_1$-C$_6$alkyl, $C_3$-$C_6$cycloalkyl, $C_1$-$C_6$alkylcarbonyl, $C_3$-$C_6$cycloalkylcarbonyl, carboxyC$_1$-C$_6$alkyl, hydroxy, amino CN, and $NO_2$, or any two $R^{22}$ groups attached to adjacent ring carbon atoms can combine to form —O—(CR$^{23}$R$^{23'}$)$_{1-6}$—O—;
$R^{23}$ and $R^{23'}$ are independently H or $C_1$-$C_3$alkyl;
or a pharmaceutically acceptable salt and/or solvate thereof.

In one embodiment, the invention provides compounds represented by formula I:

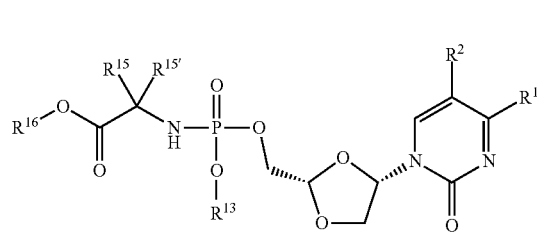

wherein:
$R^1$ is $OR^{11}$, or $NR^5R^{5'}$;
$R^2$ is H or F;
$R^5$ is H, $C_1$-$C_6$alkyl, OH, $C(=O)R^6$, $OC(=O)R^6$ or $OC(=O)OR^6$;
$R^{5'}$ is H or $C_1$-$C_6$alkyl;
$R^6$ is $C_1$-$C_2$alkyl or $C_3$-$C_7$cycloalkyl;
$R^{11}$ is H or $C_1$-$C_6$alkyl;
$R^{13}$ is H, phenyl, pyridyl, benzyl, indolyl or naphthyl wherein the phenyl, pyridyl, benzyl, indolyl and naphthyl is optionally substituted with 1, 2 or 3 $R^{22}$;
$R^{15}$ is H, $C_1$-$C_6$alkyl, $C_3$-$C_7$cycloalkyl, $C_3$-$C_7$cycloalkyl$C_1$-$C_3$alkyl, phenyl, benzyl or indolyl;
$R^{15'}$ is H or $C_1$-$C_6$alkyl; or
$R^{15}$ and $R^{15'}$ together with the carbon atom to which they are attached from a $C_3$-$C_7$cycloalkylene group, wherein each $C_1$-$C_6$alkyl is optionally substituted with a group selected from halo, $OR^{18}$ and $SR^{18}$, and each $C_3$-$C_7$cycloalkyl, $C_3$-$C_7$cycloalkylene, phenyl and benzyl is optionally substituted with one or two groups independently selected from $C_1$-$C_3$alkyl, halo and $OR^{18}$;
$R^{16}$ is H, $C_1$-$C_{10}$alkyl, $C_2$-$C_{10}$alkenyl, $C_3$-$C_7$cycloalkyl, $C_3$-$C_7$cycloalkyl$C_1$-$C_3$alkyl, benzyl, or phenyl, any of which is optionally substituted with 1, 2 or 3 groups, each independently selected from halo, $OR^{18}$ and $N(R^{18})_2$;
each $R^{18}$ is independently H, $C_1$-$C_6$alkyl, $C_1$-$C_6$haloalkyl or $C_3$-$C_7$cycloalkyl;
each $R^2$ is independently selected from halo, $C_1$-$C_6$alkyl, $C_2$-$C_6$alkenyl, $C_1$-$C_6$haloalkyl, $C_1$-$C_6$alkoxy, $C_1$-$C_6$haloalkoxy, phenyl, hydroxy$C_1$-$C_6$alkyl, $C_3$-$C_6$cycloalkyl, $C_1$-$C_6$alkylcarbonyl, $C_3$-$C_6$cycloalkylcarbonyl, carboxy$C_1$-$C_6$alkyl, hydroxy, amino CN, $NO_2$ and trimethylsilyl, or any two $R^{12}$ groups attached to adjacent ring carbon atoms can combine to form —O—$(CR^{23}R^{23'})_{1-6}$—O—;
$R^{23}$ and $R^{23'}$ are independently H or $C_1$-$C_3$alkyl;
or a pharmaceutically acceptable salt and/or solvate thereof.

The compounds of Formula (I) may optionally be provided in the form of a pharmaceutically acceptable salt and/or solvate. In one embodiment the compound of the invention is provided in the form of a pharmaceutically acceptable salt. In a second embodiment the compound of the invention is provided in the form of a pharmaceutically acceptable solvate. In a third embodiment the compound of the invention is provided in its free form.

In typical embodiments of the invention, $R^1$ is $NR^5R^{5'}$, such as $NH_2$ or $NHC(=O)C_1$-$C_6$alkyl.

$R^2$ is typically H.

In preferred embodiments, $R^1$ is $NH_2$ and $R^2$ is H.

In alternative embodiments, $R^1$ is $NH_2$ and $R^2$ is F.

Typically in compounds of formula (I), the moiety —$NHC(R^{15})(R^{15'})$—$C(=O)OR^{16}$ forms an amino acid ester residue, including natural and non-natural amino acid residues. Of particular interest are amino acid residues wherein $R^{15'}$ is hydrogen and $R^{15}$ is methyl, isopropyl, isobutyl or benzyl. In a typical configuration, $R^{15'}$ is H and $R^{15}$ is $C_1$-$C_3$alkyl, such as methyl, ethyl, propyl, isopropyl.

In compounds wherein $R^{15'}$ is hydrogen and $R^{15}$ is other than hydrogen, the configuration at the asymmetric carbon atom is typically that of an L-amino acid, thus providing compounds having the stereochemistry indicated in formula (Ia):

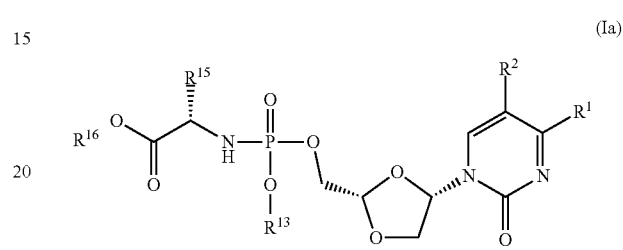

In a preferred configuration of compounds of formula Ia, $R^{15}$ is methyl.
In a further configuration of compounds of formula Ia, $R^{15}$ is benzyl.
In a representative configuration of compounds of formula Ia,
$R^1$ is $NH_2$;
$R^2$ is H;
$R^{13}$ is phenyl naphthyl or indolyl, any of which is optionally substituted with halo e.g. bromo or $C_3$-$C_4$cycloalkyl e.g. cyclopropyl;
$R^{15}$ is $C_1$-$C_3$alkyl
$R^{16}$ is $C_1$-$C_6$alkyl
In a further representative configuration of compounds of formula Ia,
$R^1$ is $NH_2$;
$R^2$ is H;
$R^{13}$ is naphthyl;
$R^{15}$ is $C_1$-$C_3$alkyl;
$R^{16}$ is $C_1$-$C_8$alkyl or benzyl;
In a further representative configuration of compounds of formula Ia,
$R^1$ is $NH_2$;
$R^2$ is H;
$R^{13}$ is phenyl which is optionally substituted in the 4-position with halo e.g. bromo or with $C_3$-$C_4$cycloalkyl, e.g. cyclopropyl;
$R^{15}$ is methyl;
$R^{16}$ is $C_3$-$C_8$alkyl.
In a further representative configuration of compounds of formula Ia,
$R^1$ is $NH_2$;
$R^2$ is H;
$R^{13}$ is phenyl;
$R^{15}$ is methyl;
$R^{16}$ is $C_3$-$C_8$alkyl
In a further representative configuration of compounds of formula Ia,
$R^1$ is $NH_2$;
$R^2$ is F;
$R^{13}$ is phenyl naphthyl or indolyl, any of which is optionally substituted with halo e.g. bromo or with $C_3$-$C_4$cycloalkyl e.g. cyclopropyl;

$R^{15}$ is $C_1$-$C_3$alkyl
$R^{16}$ is $C_1$-$C_8$alkyl

In a further representative configuration of compounds of formula Ia,
$R^1$ is $NH_2$;
$R^2$ is F;
$R^{13}$ is naphthyl;
$R^{15}$ is $C_1$-$C_3$alkyl;
$R^{16}$ is $C_1$-$C_6$alkyl or benzyl;

In a further representative configuration of compounds of formula Ia,
$R^1$ is $NH_2$;
$R^2$ is F;
$R^{13}$ is phenyl which is optionally substituted in the 4-position with halo e.g. bromo or with $C_3$-$C_4$cycloalkyl, e.g. cyclopropyl;
$R^{15}$ is methyl;
$R^{16}$ is $C_3$-$C_8$alkyl.

In a further representative configuration of compounds of formula Ia,
$R^1$ is $NH_2$;
$R^2$ is F;
$R^{13}$ is phenyl;
$R^{15}$ is methyl;
$R^{16}$ is $C_3$-$C_8$alkyl In a further configuration, $R^{15}$ and $R^{15'}$ together with the carbon atom to which they are attached form $C_3$-$C_7$cycloalkyl, for example cyclopropyl or cyclobutyl.

$R^{16}$ is typically $C_1$-$C_{10}$alkyl or $C_3$-$C_7$cycloalkyl.

Representative values for $R^{16}$ include $C_1$-$C_3$alkyl, such as methyl, ethyl, propyl, isopropyl. A preferred value for $R^{16}$ is methyl, a further preferred value for $R^{16}$ is isopropyl.

In one embodiment, $R^{16}$ is $C_3$-$C_{10}$alkyl.

Representative values for $R^{16}$ according to this embodiment include branched $C_5$-$C_8$alkyl. In one embodiment, the branching point of $R^{16}$ is at $C_1$. In an alternative embodiment, the branching point of $R^{16}$ is at $C_2$. Typically according to these embodiments, $R^{15'}$ is H, and the stereochemistry at the carbon atom to which $R^{15}$ is attached is that of an L-amino acid, thus providing compounds of the general formulae:

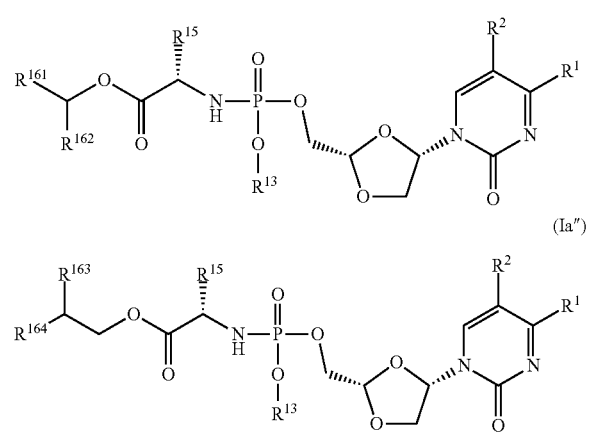

(Ia')

(Ia")

wherein $R^{161}$ and $R^{162}$ are the same or different $C_1$-$C_3$alkyl, and $R^{163}$ and $R^{164}$ are the same or different $C_1$-$C_3$alkyl.

Typically in compounds of formula (Ia'), $R^{16}$ is 2-pentyl, i.e. $R^{161}$ is propyl and $R^{162}$ is methyl.

In a further typical configuration of compounds of formula (Ia'), $R^{16}$ is 2-butyl, i.e. $R^{161}$ is ethyl and $R^{162}$ is methyl.

Typically in compounds of formula (Ia"), $R^{16}$ is 2-propylpentyl or 2-ethylbutyl, i.e. $R^{163}$ and $R^{164}$ are both propyl or ethyl respectively.

Further representative values for $R^{16}$ include $C_3$-$C_7$cycloalkyl, such as cyclohexyl.

A further representative value for $R^{16}$ is cyclopentyl.

A further representative value for $R^{16}$ is benzyl.

$R^{13}$ is typically phenyl, naphthyl or indolyl, any of which is optionally substituted with 1 or 2 $R^{22}$.

In one embodiment of the invention, $R^{13}$ is phenyl or naphthyl any of which is optionally substituted.

In one embodiment of the invention, $R^{13}$ is naphthyl.

In a preferred embodiment of the invention, $R^{13}$ is phenyl.

Representative examples of $R^{13}$ include phenyl which is optionally substituted with one, two or three $R^2$, thus providing compounds of the formula (II-aa):

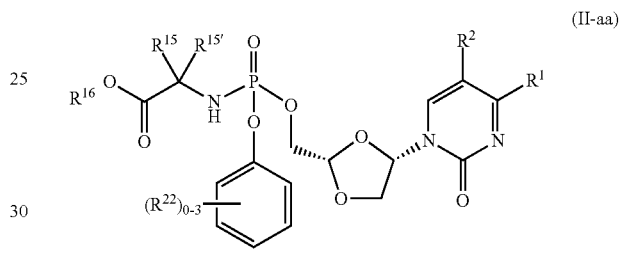

(II-aa)

wherein each $R^{22}$, when present, is independently selected from halo, $C_1$-$C_6$alkyl, $C_2$-$C_6$alkenyl and $C_1$-$C_6$alkoxy. Typically, the phenyl ring is unsubstituted or substituted with one $R^{22}$.

In one configuration of compounds of Formula (II-aa), the phenyl ring is unsubstituted.

In a further configuration of Formula (II-aa), the phenyl ring is substituted with one $R^{22}$. Typically in this configuration, the substituent $R^{22}$ is located to the 4-position of the phenyl ring.

In one embodiment of compounds of the inventions, $R^{13}$ is phenyl which is substituted in the 4-position with halo, e.g. bromo or with $C_3$-$C_4$cycloalkyl, e.g. cyclopropyl.

In one configuration of compounds of Formula (II-aa), the phenyl ring is substituted with carboxy$C_1$-$C_6$alkyl. A representative example of this configuration is illustrated in the partial formula:

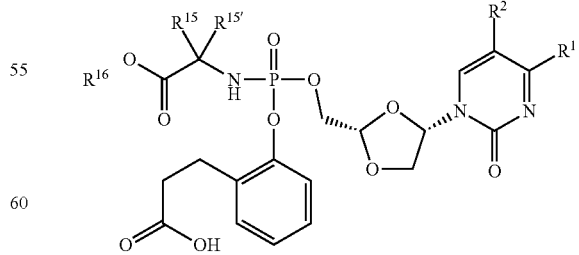

In a further configuration of compounds of Formula (II-aa), the phenyl ring is substituted with two $R^{22}$ located on adjacent carbon atoms and the two $R^2$ combine to form —O—$CH_2$O—, thus forming the partial structure:

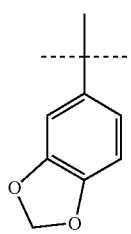

Further representative values for $R^{13}$ include optionally substituted pyridyl. Typically, the pyridyl moiety is unsubstituted or substituted with one or two substituents each independently selected from halo, $C_1$-$C_6$haloalkyl, $C_1$-$C_6$alkyl, $C_2$-$C_6$alkenyl, $C_1$-$C_6$alkoxy, hydroxy, amino.

In a typical embodiment of compounds of formula (I),
$R^1$ is $NH_2$ or $NHC(=O)C_1$-$C_6$alkyl;
$R^{13}$ is phenyl, naphthyl or indolyl, any of which is optionally substituted with halo, $C_1$-$C_3$alkyl, $C_1$-$C_3$alkoxy, $C_3$-$C_6$cycloalkyl or $C_1$-$C_3$haloalkyl;
$R^{15'}$ is H and $R^{15}$ is $C_1$-$C_3$alkyl or benzyl;
$R^{16}$ is $C_1$-$C_{10}$alkyl or $C_3$-$C_7$cycloalkyl.

In a typical embodiment of compounds of formula (I) or (Ia),
$R^1$ is $NH_2$ or $NHC(=O)C_1$-$C_6$alkyl;
$R^{13}$ is phenyl or naphthyl, any of which is optionally substituted with halo, $C_1$-$C_3$alkyl, $C_1$-$C_3$alkoxy, $C_3$-$C_6$cycloalkyl or $C_1$-$C_3$haloalkyl;
$R^{15'}$ is H and $R^{15}$ is $C_1$-$C_3$alkyl or benzyl;
$R^{16}$ is $C_2$-$C_{10}$alkyl or $C_3$-$C_7$cycloalkyl.

In a further typical embodiment of compounds of formula (I),
$R^1$ is $NH_2$;
$R^2$ is H;
$R^{13}$ is phenyl;
$R^{15'}$ is H and $R^{15}$ is $C_1$-$C_3$alkyl;
$R^{16}$ is $C_1$-$C_3$alkyl or cyclohexyl.

In a further typical embodiment of compounds of Formula (I) or (Ia),
$R^1$ is $NH_2$;
$R^2$ is H;
$R^{13}$ is phenyl;
$R^{15'}$ is H and $R^{15}$ is $C_1$-$C_3$alkyl or benzyl;
$R^{16}$ is $C_3$-$C_6$alkyl, cyclopentyl or cyclohexyl.

The compounds of the present invention show activity against cancer especially liver cancer such as HCC, and can be used as medicine in the treatment of warm-blooded animals, particularly humans, having cancer. Especially the compounds can be used as medicine in the treatment of humans having liver cancer such as HCC.

In order to avoid undesired side effects, particularly toxicity in other organs, delivery of the drug to the site of the tumour while reducing exposure to normal tissue is crucial. The compounds of the invention are stable in gastric fluid but readily metabolized by liver enzymes, they may therefore be absorbed in the stomach and transported as a masked cytotoxic agent to the liver where absorption, metabolism and formation of the active cytotoxic triphosphate occurs. Accordingly, the invention provides compounds which are absorbed and processed primarily in the liver, thus minimizing exposure to other organs in the body and toxic side effects.

Without wishing to be bound by theory, the anti-oncogenic activity of the compounds of the invention may be exerted directly against cellular processes of the rapidly acting tumourogenic cells of the cancer, but may additionally or alternatively exert their effects through modulation of the tumour's microenvironment, such as inhibition of angiogenesis, thereby starving the tumour of nourishment leading to inhibition of tumour growth.

The compounds of the present invention are also useful in the treatment of secondary liver cancers, metastasis in the liver, i.e. cancer that originate from organs elsewhere in the body, such as the colon, lung or breast and migrates to the liver.

The present invention also relates to a method of treating warm-blooded animals, in particular humans, having cancer, especially liver cancer such as HCC, said method comprises the administration of an effective amount of a compound of Formula (I) or any subgroup thereof.

The present invention also relates to a method of treating warm-blooded animals, in particular humans, having a secondary liver cancer, said method comprises the administration of an effective amount of a compound of Formula (I) or any subgroup thereof.

Said use as a medicine or method of treatment comprises the systemic administration to a subject having cancer of an effective amount of a compound of Formula (I).

In one aspect, the invention provides a pharmaceutical composition comprising a compound of Formula (I) in association with a pharmaceutically acceptable adjuvant, diluent, excipient or carrier.

In a further aspect, the invention provides a pharmaceutical composition for use in the treatment of cancer comprising a compound of Formula (I) in association with a pharmaceutically acceptable adjuvant, diluent, excipient or carrier.

In a further aspect, the invention provides a pharmaceutical composition for use in the treatment of liver cancer, such as HCC comprising a compound of Formula (I) in association with a pharmaceutically acceptable adjuvant, diluent, excipient or carrier.

In a further aspect, the invention provides a pharmaceutical composition for use in the treatment of a secondary liver cancer comprising a compound of Formula (I) in association with a pharmaceutically acceptable adjuvant, diluent, excipient or carrier.

In a further aspect, the invention relates to a process of preparing a pharmaceutical composition as specified herein, which comprises intimately mixing a pharmaceutically acceptable adjuvant, diluent, excipient and/or carrier with a therapeutically effective amount of a compound of Formula (I).

In a further aspect, the invention provides a pharmaceutical composition for use in the treatment or inhibition mentioned above, which further comprises one or more additional therapeutic agents.

The pharmaceutical compositions mentioned above will typically contain an effective amount (e.g. for humans) of the compound of Formula (I), although sub-therapeutic amounts of the compound of Formula (I) may nevertheless be of value when intended for use in combination with other agents or in multiple doses.

In this context a therapeutically effective amount is an amount sufficient to produce an intended result. The therapeutically effective amount will vary depending on individual requirements in each particular case. Features that influence the dose are e.g. the severity of the disease to be treated, age, weight, general health condition etc. of the subject to be treated. With respect to an anti-cancer effect, that effect may be inhibition of further tumour growth, reduction of the likelihood or elimination of metastasis or producing cell death in the tumour, resulting in a shrinkage of the tumour or preventing the regrowth of a tumour after the patient's tumour is in remission.

In a further aspect, the present invention provides a compound of Formula (I) for use as a medicament.

In a further aspect, the present invention provides a compound of Formula (I) for use in the treatment of cancer.

In a further aspect, the present invention provides a compound of Formula (I) for use in the treatment of liver cancer such as HCC.

In a further aspect, the present invention provides a compound of Formula (I) for use in the treatment of a secondary liver cancer.

In a further aspect, the present invention provides a compound of Formula (I) for use in the treatment as described above in combination with one or more additional cancer treatment(s) such as other anti-cancer drugs, surgery, immunotherapy and/or regional therapies like radiofrequency ablation.

In a further embodiment, an additional anticancer treatment is radiotherapy.

In one embodiment, an additional anticancer treatment is one or more other nucleoside analogue(s) which exhibit potent antitumor activity.

In one aspect the present invention provides a pharmaceutical combination comprising a therapeutically effective amount of compound of formula and one or more additional therapeutic agent(s) selected from the group consisting of chemotherapeutical agent, multi-drug resistance reversing agent and biological response modifier.

In one embodiment of this aspect, a further therapeutic agent is a chemotherapeutical agent.

In a further aspect, the present invention provides a compound of Formula (I) for use in the manufacture of a medicament.

In a further aspect, the present invention provides a compound of Formula (I) for use in the manufacture of a medicament for the treatment of cancer.

In a further aspect, the present invention provides a compound of Formula (I) for use in the manufacture of a medicament for the treatment of liver cancer such as HCC.

In a further aspect, the present invention provides a compound of Formula (I) for use in the manufacture of a medicament for the treatment of a secondary liver cancer.

In a further aspect, the present invention provides a method for the treatment of cancer comprising the administration of a therapeutically effective amount of a compound of Formula (I), to a subject, e.g. a human in need thereof.

In a further aspect, the present invention provides a method for the treatment of liver cancer such as HCC, comprising the administration of a therapeutically effective amount of a compound of Formula (I) to a subject, e.g. a human in need thereof.

In a further aspect, the present invention provides a method for the treatment of a secondary liver cancer, comprising the administration of a therapeutically effective amount of a compound of Formula (I) to a subject, e.g. a human in need thereof.

In a further aspect, the present invention provides a method for the treatment as described above in combination with additional cancer treatment(s) such as other anti-cancer drugs, surgery, immunotherapy and/or regional therapies like radiofrequency ablation.

In one aspect the present invention provides a method of treatment of a primary or secondary liver cancer comprising the administration of a pharmaceutical combination comprising a therapeutically effective amount of compound of formula I, further comprising one or more additional therapeutic agent(s) selected from the group consisting of chemotherapeutical agent, multi-drug resistance reversing agent and biological response modifier.

In one embodiment of this aspect, a further therapeutic agent is a chemotherapeutic agent. In one aspect, the invention provides a compound of Formula (I) which is selected from the compounds depicted below:

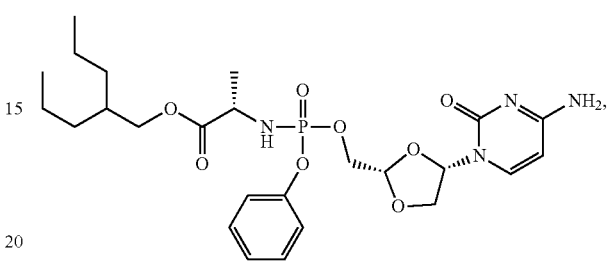

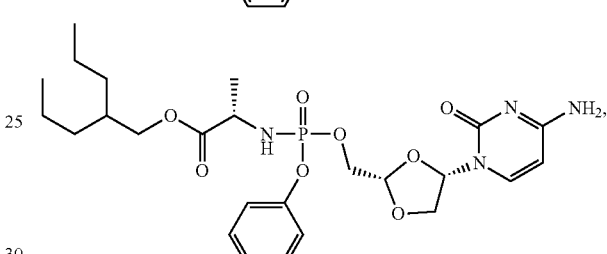

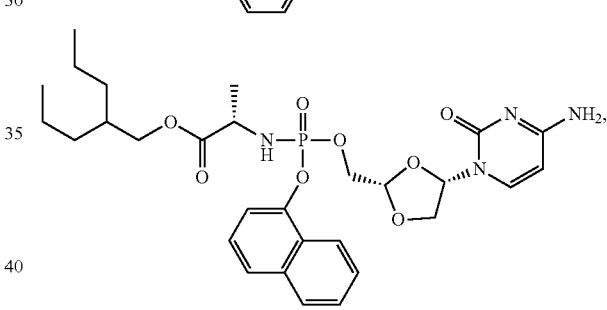

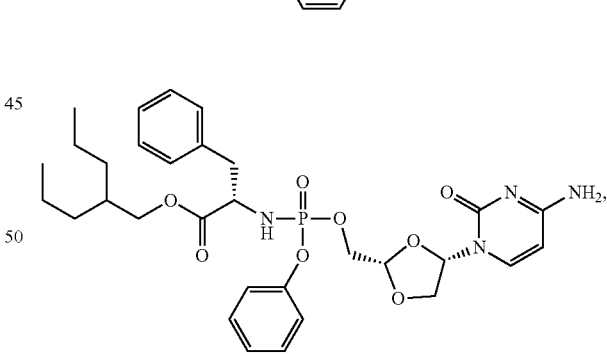

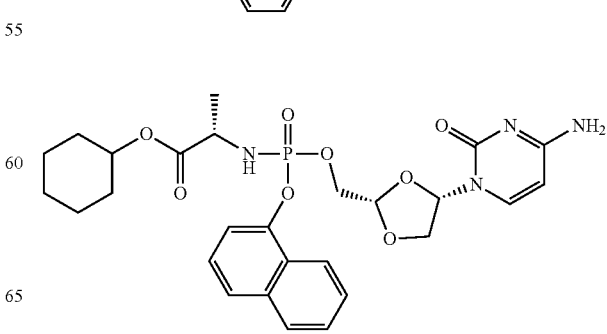

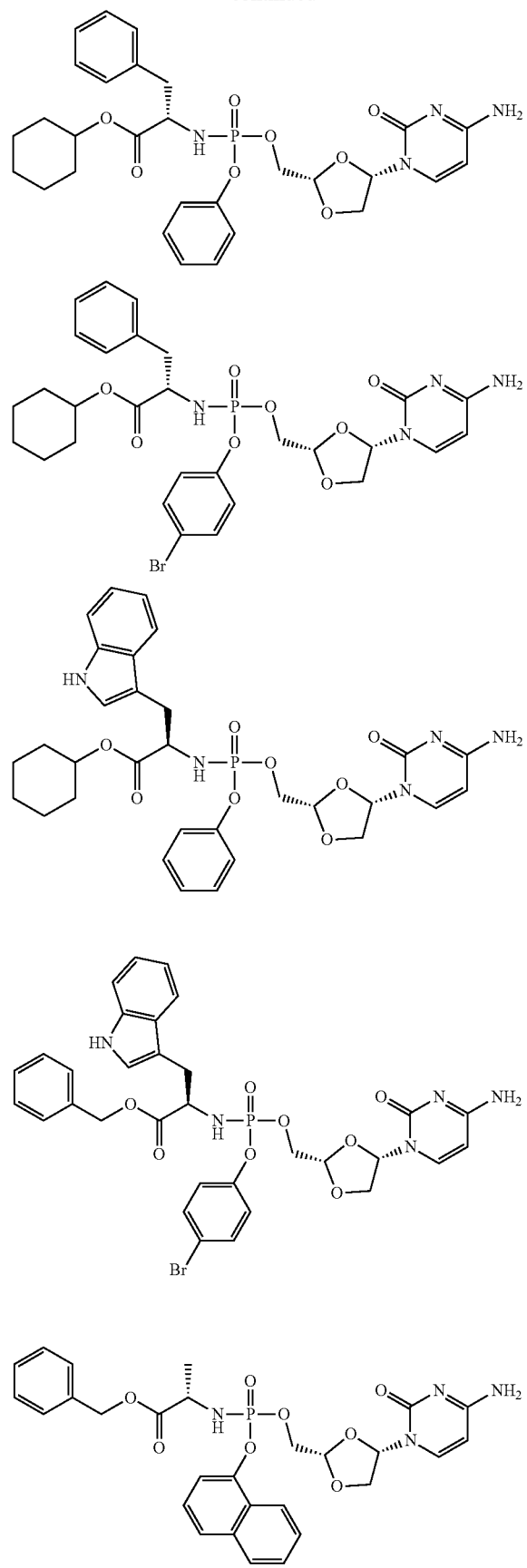
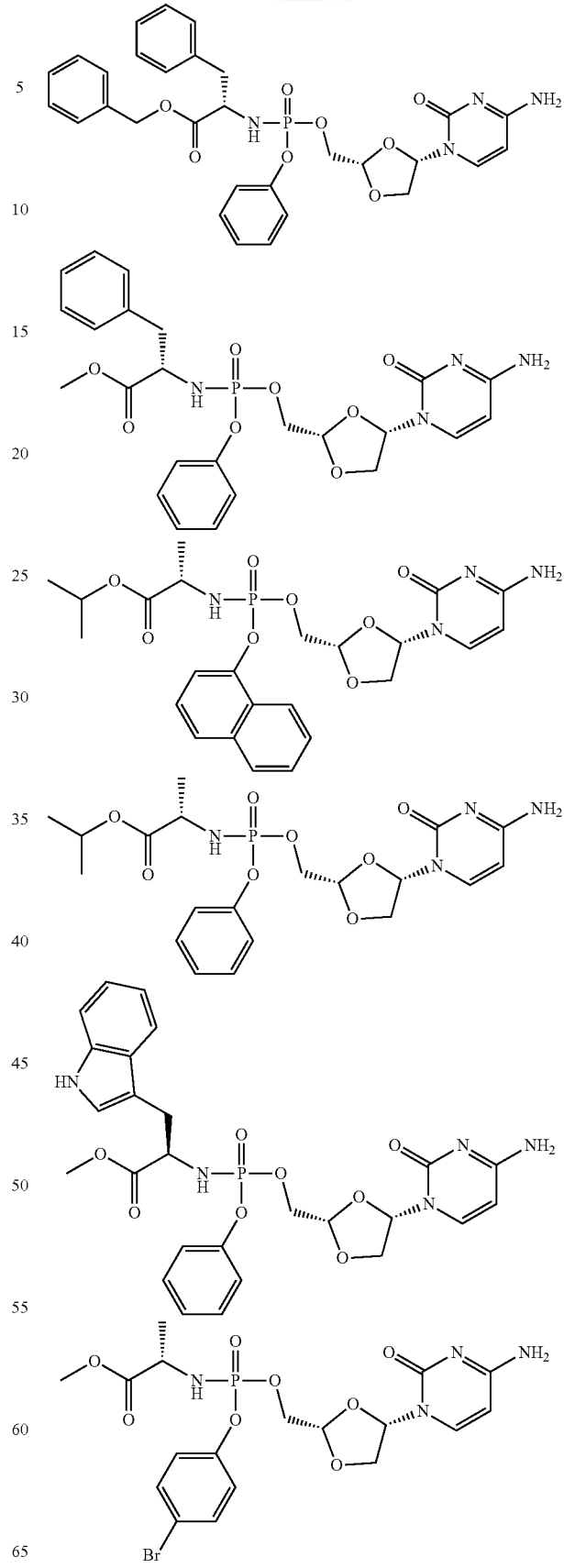

or a pharmaceutically acceptble salt thereof.

Furthermore, the invention relates to a method for manufacturing a compound of Formula (I), to novel intermediates for use in the manufacture of compounds of Formula (I) and to the manufacture of such intermediates.

Whenever the term 'compounds of Formula (I)', "the compounds of the invention", "the compounds of the present invention" or similar terms is used in the foregoing and hereinafter, it is meant to include the compounds of Formula (I) and any subgroup of compounds of Formula (I), including all possible stereochemically isomeric forms, their pharmaceutically acceptable salts, solvates, quaternary amines and metal complexes.

The compounds of the present invention may be formulated into various pharmaceutical forms for administration purposes. As appropriate compositions there may be cited all compositions usually employed for oral administration of drugs. To prepare the pharmaceutical compositions of this invention, an effective amount of the particular compound, optionally in addition salt form or solvate, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable for oral administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations intended to be converted, shortly before use, to liquid form preparations.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers and the like, and segregated multiples thereof.

In general it is contemplated that an an-cancer effective daily amount would be from about 0.01 to about 700 mg/kg, or about 0.5 to about 400 mg/kg, or about 1 to about 250 mg/kg, or about 2 to about 200 mg/kg, or about 10 to about 150 mg/kg body weight. It may be appropriate to administer the required dose as two, three, four or more sub-doses at appropriate intervals throughout the day. Said sub-doses may be formulated as unit dosage forms, for example, containing about 1 to about 5000 mg, or about 50 to about 3000 mg, or about 100 to about 1000 mg, or about 200 to about 600 mg, or about 100 to about 400 mg of active ingredient per unit dosage form.

The compounds of the present invention may exhibit an anticancer effect alone and/or enhance the ability of another anti-cancer agent to exhibit an anticancer effect.

The compounds of the invention are represented as a defined stereoisomer. The absolute configuration of such compounds can be determined using art-known methods such as, for example, X-ray diffraction or NMR and/or implication from start materials of known stereochemistry. Pharmaceutical compositions in accordance with the invention will preferably comprise substantially stereoisomerically pure preparations of the indicated stereoisomer.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoytartaric acid, ditoluoyltartaric acid and camphorsulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically.

Preferably, if a specific stereoisomer is desired, said compound is synthesized by stereospecific methods of preparation. These methods will advantageously employ enantiomerically pure starting materials.

The diastereomeric racemates of the compounds of the invention can be obtained separately by conventional methods. Appropriate physical separation methods that may advantageously be employed are, for example, selective crystallization and chromatography, e.g. column chromatography.

When a phosphorus atom is present in a compound of the invention, the phosphorus atom may represent a chiral centre. The chirality at this centre is designated "R" or "S" according to the Cahn-Ingold-Prelog priority rules. When the chirality is not indicated, it is contemplated that both the R- and S-isomers are meant to be included, as well as a mixture of both, i.e. a diastereomeric mixture.

In preferred embodiments of the invention, the stereoisomers having the S-configuration at the phosphorus atom are included. These stereoisomers are designated $S_P$.

In other embodiments of the invention, the stereoisomers having the R-configuration at the phosphorus atom are included. These stereoisomers are designated $R_P$.

In other embodiments of the invention, diastereomeric mixtures are included, i.e. mixtures of compounds having the R- or S-configuration at the phosphorus atom.

The present invention also includes isotope-labelled compounds of Formula (I), wherein one or more of the atoms is replaced by an isotope of that atom, i.e. an atom having the same atomic number as, but an atomic mass different from, the one(s) typically found in nature. Examples of isotopes that may be incorporated into the compounds of Formula (I), include but are not limited to isotopes of hydrogen, such as $^{2}$H and $^{3}$H (also denoted D for deuterium and T for tritium, respectively), carbon, such as $^{11}$C, $^{13}$C and $^{14}$C, nitrogen, such as $^{13}$N and $^{15}$N, oxygen, such as $^{15}$O, $^{17}$O and $^{18}$O, phosphorus, such as $^{31}$P and $^{32}$P, sulfur, such as $^{35}$S, fluorine, such as $^{18}$F, chlorine, such as $^{35}$Cl, bromine such as $^{75}$Br, $^{76}$Br, $^{77}$Br and $^{82}$Br, and iodine, such as $^{123}$I, $^{124}$I, $^{125}$I and $^{131}$I. The choice of isotope included in an isotope-labelled compound will depend on the specific application of that compound. For example, for drug or substrate tissue distribution assays, compounds wherein a radioactive isotope such as $^{3}$H or $^{14}$C is incorporated will generally be most useful. For radio-imaging applications, for example positron emission tomography (PET) a positron emitting isotope such as $^{11}$C, $^{18}$F, $^{13}$N or $^{15}$O will be useful. The incorporation of a heavier isotope, such as deuterium, i.e. $^{2}$H, may provide greater metabolic stability to a compound of Formula (I) which may result in, for example, an increased in vivo half life of the compound or reduced dosage requirements.

Isotope-labelled compounds of the invention can be prepared by processes analogous to those described in the Schemes and/or Examples herein below by using the appropriate isotope-labelled reagent or starting material instead of the corresponding non-isotope-labelled reagent or starting material, or by conventional techniques known to those skilled in the art.

The pharmaceutically acceptable addition salts comprise the therapeutically active acid and base addition salt forms of the compounds of Formula (I). Of interest are the free, i.e. non-salt forms of the compounds of Formula (I) or any subgroup thereof.

The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propionic, hydroxyacetic, lactic, pyruvic, oxalic (i.e. ethanedioic), malonic, succinic (i.e. butanedioic acid), maleic, fumaric, malic (i.e. hydroxylbutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

Some of the compounds of Formula (I) may also exist in their tautomeric form. For example, tautomeric forms of amide groups (—C(=O)—NH—) are iminoalcohols (—C (OH)=N—), which can become stabilized in rings with aromatic character. Such forms, although not explicitly indicated in the structural formulae represented herein, are intended to be included within the scope of the present invention.

The terms and expressions used herein throughout the abstract, specification and claims shall be interpreted as defined below unless otherwise indicated. The meaning of each term is independent at each occurrence. These definitions apply regardless of whether a term is used by itself or in combination with other terms, unless otherwise indicated. A term or expression used herein which is not explicitly defined, shall be interpreted as having its ordinary meaning used in the art. Chemical names, common names, and chemical structures may be used interchangeably to describe the same structure. If a chemical compound is referred to using both a chemical structure and a chemical name and an ambiguity exists between the structure and the name, the structure predominates.

"$C_m$-$C_n$alkyl" on its own or in composite expressions such as $C_m$-$C_n$haloalkyl, $C_m$-$C_n$alkylcarbonyl, $C_m$-$C_n$alkylamine, etc. represents a straight or branched aliphatic hydrocarbon radical having the number of carbon atoms designated, e.g. $C_1$-$C_4$alkyl means an alkyl radical having from 1 to 4 carbon atoms. $C_1$-$C_6$alkyl has a corresponding meaning, including also all straight and branched chain isomers of pentyl and hexyl. Preferred alkyl radicals for use in the present invention are $C_1$-$C_6$alkyl, including methyl, ethyl, n-propyl, isopropyl, n-butyl, isobutyl, sec-buty, tert-butyl, n-pentyl and n-hexyl, especially $C_1$-$C_4$alkyl such as methyl, ethyl, n-propyl, isopropyl, t-butyl, n-butyl and isobutyl. Methyl and isopropyl are typically preferred. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH (alkyl), —N(alkyl)$_2$, —NH(cycloalkyl), —O—C(=O)-alkyl, —O—C(=O)-aryl, —O— C(=O)-cycloalkyl, —C(=O)OH and —C(=O)O-alkyl. It is generally preferred that the alkyl group is unsubstituted, unless otherwise indicated.

"$C_2$-$C_n$alkenyl" represents a straight or branched aliphatic hydrocarbon radical containing at least one carbon-carbon double bond and having the number of carbon atoms designated, e.g. $C_2$-$C_4$alkenyl means an alkenyl radical having from 2 to 4 carbon atoms; $C_2$-$C_6$alkenyl means an alkenyl radical having from 2 to 6 carbon atoms. Non-limiting alkenyl groups include ethenyl, propenyl, n-butenyl, 3-methylbut-2-enyl, n-pentenyl and hexenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(=O)-alkyl, —O—C(=O)-aryl, —O—C(=O)-cycloalkyl, —C(=O)OH and —C(=O)O-alkyl. It is generally preferred that the alkenyl group is unsubstituted, unless otherwise indicated.

"$C_2$-$C_n$alkynyl" represents a straight or branched aliphatic hydrocarbon radical containing at least one carbon-carbon triple bond and having the number of carbon atoms designated, e.g. $C_2$-$C_4$alkynyl means an alkynyl radical having from 2 to 4 carbon atoms; $C_2$-$C_6$alkynyl means an alkynyl radical having from 2 to 6 carbon atoms. Non-limiting alkenyl groups include ethynyl, propynyl, 2-butynyl and 3-methylbutynyl pentynyl and hexynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkyithio, —NH$_2$, —NH(alkyl), —N(alkyl)$_2$, —NH(cycloalkyl), —O—C (=O)-alkyl, —O—C(=O)-aryl, —O—C(=O)-cycloalkyl, —C(O)OH and —C(O)O-alkyl. It is generally preferred that the alkynyl group is unsubstituted, unless otherwise indicated.

The term "$C_m$-$C_n$haloalkyl" as used herein represents $C_m$-$C_n$alkyl wherein at least one C atom is substituted with a halogen (e.g. the $C_m$-$C_n$haloalkyl group may contain one to three halogen atoms), preferably chloro or fluoro. Typical haloalkyl groups are $C_1$-$C_2$haloalkyl, in which halo suitably represents fluoro. Exemplary haloalkyl groups include fluoromethyl, difluromethyl and trifluoromethyl.

The term "$C_m$-$C_n$hydroxyalkyl" as used herein represents $C_m$-$C_n$alkyl wherein at least one C atom is substituted with one hydroxy group. Typical $C_m$-$C_n$hydroxyalkyl groups are $C_m$-$C_n$alkyl wherein one C atom is substituted with one hydroxy group. Exemplary hydroxyalkyl groups include hydroxymethyl and hydroxyethyl.

The term "$C_m$-$C_n$aminoalkyl" as used herein represents $C_m$-$C_n$alkyl wherein at least one C atom is substituted with one amino group. Typical $C_m$-$C_n$aminoalkyl groups are $C_m$-$C_n$alkyl wherein one C atom is substituted with one amino group. Exemplary aminoalkyl groups include aminomethyl and aminoethyl.

The term "$C_m$-$C_n$alkylene" as used herein represents a straight or branched bivalent alkyl radical having the number of carbon atoms indicated. Preferred $C_m$-$C_n$alkylene radicals for use in the present invention are $C_1$-$C_3$alkylene. Non-limiting examples of alkylene groups include —$CH_2$—, —$CH_2CH_2$—, —$CH_2CH_2CH_2$—, —$CH(CH_3)CH_2CH_2$—, —$CH(CH_3)$— and —$CH(CH(CH_3)_2)$—.

The term "Me" means methyl, and "MeO" means methoxy.

The term "$C_m$-$C_n$alkylcarbonyl" represents a radical of the formula $C_m$-$C_n$alkyl-C(=O)— wherein the $C_m$-$C_n$alkyl moiety is as defined above. Typically, "$C_m$-$C_n$alkylcarbonyl" is $C_1$-$C_6$alkyl-C(=O)—.

"$C_m$-$C_n$alkoxy" represents a radical $C_m$-$C_n$alkyl-O— wherein $C_m$-$C_n$alkyl is as defined above. Of particular interest is $C_1$-$C_4$alkoxy which includes methoxy, ethoxy, n-propoxy, isopropoxy, t-butoxy, n-butoxy and isobutoxy. Methoxy and isopropoxy are typically preferred. $C_1$-$C_6$alkoxy has a corresponding meaning, expanded to include all straight and branched chain isomers of pentoxy and hexoxy.

The term "$C_m$-$C_n$alkoxycarbonyl" represents a radical of the formula $C_m$-$C_n$alkoxy-C(=O)— wherein the $C_m$-$C_n$alkoxy moiety is as defined above. Typically, "$C_m$-$C_n$alkoxycarbonyl" is $C_1$-$C_6$alkoxy-C(=O)—.

The term "amino" represents the radical —$NH_2$.

The term "halo" represents a halogen radical such as fluoro, chloro, bromo or iodo. Typically, halo groups are fluoro or chloro.

The term "aryl" means a phenyl, biphenyl or naphthyl group.

The term "heterocycloalkyl" represents a stable saturated monocyclic 3-7 membered ring containing 1-3 heteroatoms independently selected from O, S and N. In one embodiment the stable saturated monocyclic 3-7 membered ring contains 1 heteroatom selected from O, S and N. In a second embodiment the stable saturated monocyclic 3-7 membered ring contains 2 heteroatoms independently selected from O, S and N. In a third embodiment the stable saturated monocyclic 3-7 membered ring contains 3 heteroatoms independently selected from O, S and N. The stable saturated monocyclic 3-7 membered ring containing 1-3 heteroatoms independently selected from O, S and N may typically be a 5-7 membered ring, such as a 5 or 6 membered ring. A heterocycloalkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(=O)-alkyl, —O—C(=O)-aryl, —O—C(=O)-cycloalkyl, —C(=O)OH and —C(=O)O-alkyl. It is generally preferred that the heterocycloalkyl group is unsubstituted, unless otherwise indicated.

The term "heteroaryl" represents a stable mono or bicyclic aromatic ring system containing 1-4 heteroatoms independently selected from O, S and N, each ring having 5 or 6 ring atoms. In one embodiment of the invention the stable mono or bicyclic aromatic ring system contains one heteroatom selected from O, S and N, each ring having 5 or 6 ring atoms. In a second embodiment of the invention the stable mono or bicyclic aromatic ring system contains two heteroatoms independently selected from O, S and N, each ring having 5 or 6 ring atoms. In a third embodiment the stable mono or bicyclic aromatic ring system contains three heteroatoms independently selected from O, S and N, each ring having 5 or 6 ring atoms. In a fourth embodiment the stable mono or bicyclic aromatic ring system contains four heteroatoms independently selected from O, S and N, each ring having 5 or 6 ring atoms.

One embodiment of heteroaryl comprises flavone.

The term "$C_3$-$C_n$cycloalkyl" represents a cyclic monovalent alkyl radical having the number of carbon atoms indicated, e.g. $C_3$-$C_7$cycloalkyl means a cyclic monovalent alkyl radical having from 3 to 7 carbon atoms. Preferred cycloalkyl radicals for use in the present invention are $C_3$-$C_4$alkyl i.e. cyclopropyl and cyclobutyl. A cycloalkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(=O)-alkyl, —O—C(=O)-aryl, —O—C(=O)-cycloalkyl, —C(=O)OH and —C(=O)O-alkyl. It is generally preferred that the cycloalkyl group is unsubstituted, unless otherwise indicated.

The term "amino$C_m$-$C_n$alkyl" represents a $C_m$-$C_n$alkyl radical as defined above which is substituted with an amino group, i.e. one hydrogen atom of the alkyl moiety is replaced by an $NH_2$-group. Typically, "amino$C_m$-$C_n$alkyl" is amino$C_1$-$C_6$alkyl.

The term "amino$C_m$-$C_n$alkylcarbonyl" represents a $C_m$-$C_n$alkylcarbonyl radical as defined above, wherein one hydrogen atom of the alkyl moiety is replaced by an $NH_2$-group. Typically, "amino$C_m$-$C_n$alkylcarbonyl" is amino$C_1$-$C_6$alkylcarbonyl. Examples of amino$C_m$-$C_n$alkylcarbonyl include but are not limited to glycyl: C(=O)$CH_2NH_2$, alanyl: C(=O)CH($NH_2$)$CH_3$, valinyl: C—OCH($NH_2$)CH($CH_3$)$_2$, leucinyl: C(=O)CH($NH_2$)($CH_2$)$_3CH_3$, isoleucinyl: C(=O)CH($NH_2$)CH($CH_3$)($CH_2CH_3$) and norleucinyl: C(=O)CH($NH_2$)($CH_2$)$_3CH_3$ and the like. This definition is not limited to naturally occurring amino acids.

As used herein, the term "(=O)" forms a carbonyl moiety when attached to a carbon atom. It should be noted that an atom can only carry an oxo group when the valency of that atom so permits.

The term "monophosphate, diphosphate and triphosphate ester" refers to the groups:

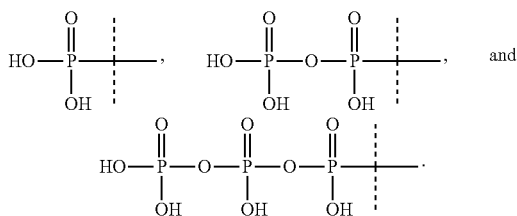

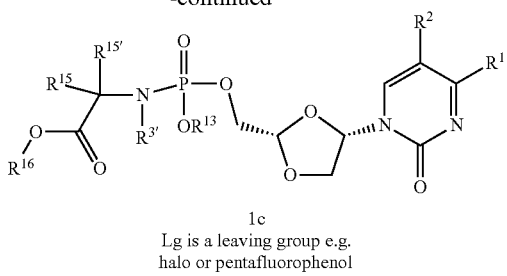

1c
Lg is a leaving group e.g.
halo or pentafluorophenol

As used herein, the radical positions on any molecular moiety used in the definitions may be anywhere on such a moiety as long as it is chemically stable. When any variable present occurs more than once in any moiety, each definition is independent.

The term "solvates" covers any pharmaceutically acceptable solvates that the compounds of Formula (I) as well as the salts thereof, are able to form. Such solvates are for example hydrates, alcoholates, e.g. ethanolates, propanolates, and the like, especially hydrates.

The term "prodrug" as used herein denotes a compound that is a drug precursor which upon administration to a subject are readily convertible in vivo by metabolic and/or chemical processes to yield the active compound.

The expression "liver targeted prodrug" as used herein denotes a prodrug which is metabolised to its active species predominantly in the liver.

The expression "liver cancer" as used herein is meant to include both primary and secondary liver cancer, i.e. cancer that origins in the liver, and liver metastasis from cancer in other organs respectively.

Related terms are to be interpreted in line with the definitions provided above and the common usage in the technical field.

In general, the names of compounds used in this application are generated using ChemDraw Ultra 12.0. In addition, if the stereochemistry of a structure or a portion of a structure is not indicated with for example bold or dashed lines, the structure or portion of that structure is to be interpreted as encompassing all stereoisomers of it.

General Synthetic Methods

Compounds of the present invention may be prepared by a variety of methods e.g. as depicted in the illustrative synthetic schemes shown and described below. The starting materials and reagents used are available from commercial suppliers or can be prepared according to literature procedures set forth in references using methods well known to those skilled in the art.

Scheme 1 illustrates a general route to compounds of Formula (I).

Scheme 1

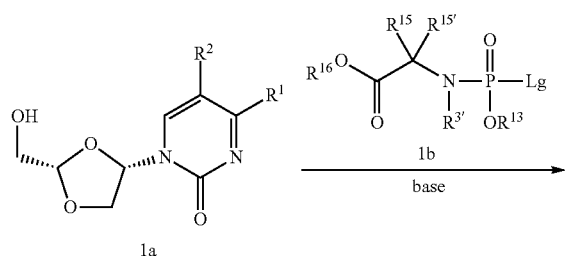

Condensation of commercially available troxacitabine derivative (1a), prepared as described above, with a desired phosphoramidate reagent (1b) wherein Lg is a suitable leaving group such as a halogen like chloride or an activated phenol like pentachlorophenol, p-nitrophenol, pentafluorophenol or the like, in an inert solvent such as an ether, e.g. diethyl ether or THF, or a halogenated hydrocarbon, e.g. dichloromethane, in the presence of a base such as a N-methylimidazole (NMI) or a Grignard reagent like tert-butylmagnesium chloride or the like, the phosphoramidate derivative (1c).

Phosphoramidate reagents (1b) to be used in the above scheme wherein Lg is chloro, i.e. phosphoramidochloridates, can be prepared in a two-step reaction starting from phosphorus oxychloride ($POCl_3$) as illustrated in Scheme 2.

Scheme 2

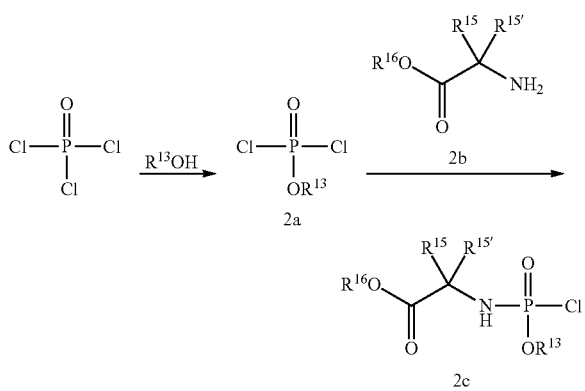

Condensation of $POCl_3$ with a desired alcohol $R^{13}OH$ in an inert solvent like $Et_2O$ provides alkoxy or aryloxy phosphorodichloridate (2a). Subsequent reaction with an amino acid derivative (2b) provides the phosphoramidochloridates wherein $R^{3'}$ is H (2c).

If desired, the obtained phosphoramidochloridates (2c) may be converted to the corresponding phosphorylating agent having an activated phenol as leaving group, for instance pentaflurorophenol or p-$NO_2$-phenol as generally illustrated in Scheme 3.

Scheme 3

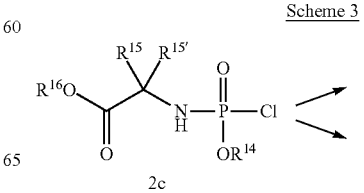

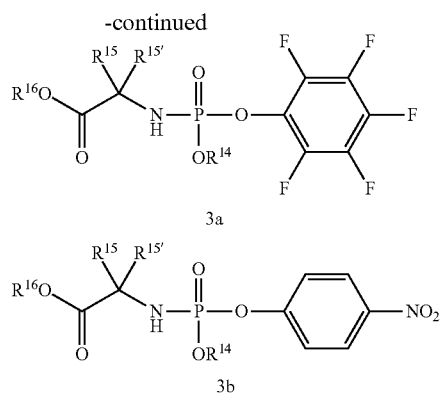

3a

3b

This conversion is conveniently performed by reaction of the chloro derivative (2c) with the desired activated phenol in the presence of a base like triethylamine or similar, thus providing phosphorylating agents (3a) and (3b).

The use of various protecting groups (PG) used in schemes above are known to the skilled person, and their utility and further alternatives are extensively described in the literature, see for instance Greene T. W., Wuts P. G. M. Protective groups in organic synthesis, 2nd ed. New York: Wiley; 1995.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in Greene. N-protecting groups include acyl groups such as formyl, acetyl, propionyl, pivaloyl, t-butylacetyl, 2-chloroacetyl, 2-bromoacetyl, trifluoroacetyl, trichbroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl, and the like; carbamate forming groups such as benzyloxycarbonyl, p-chlorobenzyloxy-carbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenyl)-1-methylethoxycarbonyl, α,α-dimethyl-3,5-dimethoxybenzyloxycarbonyl, benzhydryloxycarbonyl, t-butoxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenythiocarbonyl, and the like; alkyl groups such as benzyl, triphenylmethyl, benzyloxymethyl and the like; and silyl groups such as trimethylsilyl and the like. Favoured N-protecting groups include formyl, acetyl, benzoyl, pivaloyl, t-butylacetyl, phenylsulfonyl, benzyl (Bz), t-butoxycarbonyl (BOC) and benzyloxycarbonyl (Cbz).

Hydroxy and/or carboxy protecting groups are also extensively reviewed in Greene ibid and include ethers such as methyl, substituted methyl ethers such as methoxymethyl, methythiomethyl, benzyloxymethyl, t-butoxymethyl, 2-methoxyethoxymethyl and the like, silyl ethers such as trimethylsilyl (TMS), t-butyldimethylsilyl (TBDMS) tribenzylsilyl, triphenylsilyl, t-butyldiphenylsilyl, triisopropyl silyl and the like, substituted ethyl ethers such as 1-ethoxymethyl, 1-methyl-1-methoxyethyl, t-butyl, allyl, benzyl, p-methoxybenzyl, diphenylmethyl, triphenylmethyl and the like, aralkyl groups such as trityl, and pixyl (9-hydroxy-9-phenylxanthene derivatives, especially the chloride). Ester hydroxy protecting groups include esters such as formate, benzyformate, chloroacetate, methoxyacetate, phenoxyacetate, pivaloate, adamantoate, mesitoate, benzoate and the like. Carbonate hydroxy protecting groups include methyl vinyl, allyl, cinnamyl, benzyl and the like.

DETAILED DESCRIPTION OF THE EMBODIMENTS

Various embodiments of the invention and intermediates therefore will now be illustrated by the following examples. The Examples are just intended to further illustrate the invention and are by no means limiting the scope of the invention. The compound names were generated by ChemDraw Ultra software, Cambridgesoft, version 12.0.2.

In addition to the definitions above, the following abbreviations are used in the synthetic schemes above and the examples below. If an abbreviation used herein is not defined it has its generally accepted meaning.

Bn Benzyl
BOP-Cl Bis(2-oxo-3-oxazolidinyl)phosphinic chloride
DCC Dicyclohexylcarbodiimide
DCM Dichloromethane
DIEA Diisopropylethylamine
DMAP 4-Dimethylaminopyridine
DMF N,N-Dimethytformamide
EtOAc Ethyl acetate
Et$_3$N Triethylamine
EtOH Ethanol
Et$_2$O Diethyl ether
LC Liquid chromatography
HOAc Acetic acid
HPLC High performance liquid chromatography
MeCN Acetonitrile
MeOH Methanol
NT 3-Nitro-1,2,4-triazole
on Over night
Pg Protecting group
Ph Phenyl
rt Room temperature
TEST bis(triethoxysilyl)propyl-tetrasulfide
THF Tetrahydrofuran
TFA Trifluoroacetic acid
TFAA Trifluoroacetic anhydride
TIPS Triisopropylsilyl Preparation of troxacitabine

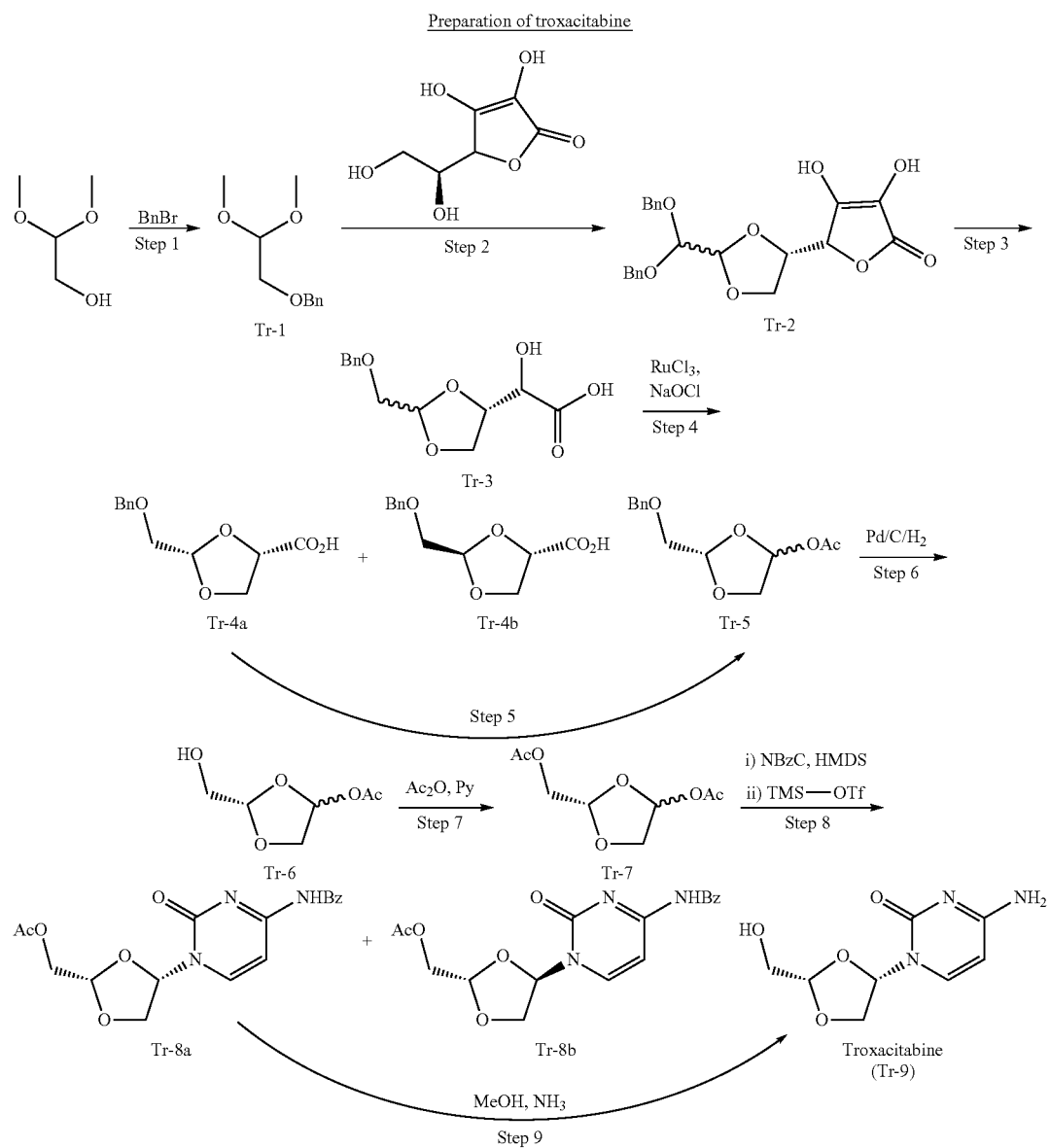

Step 1) ((2,2-dimethoxyethoxy)methyl)benzene (Tr-1)

To a stirred solution of 2,2-dimethoxyethanol (50 g, 0.471 mol) in DMF (200 mL), benzyl bromide (56.03 mL, 0.471 mol) and NaOH (20.7 g, 0.518 mol) were added at 0° C. and the reaction mixture was stirred at room temperature for 16 h. After completion of the reaction (TLC), saturated sodium chloride solution (500 mL) was added and the reaction mixture was extracted with DCM (1 L), the organic phase was dried (Na$_2$SO$_4$) and concentrated and the afforded crude was purified by silica gel column chromatography on 60-120 silica as 4-6% EtOAc in hexane to afford the title compound (60 g, 60%) as a liquid.

Step 2) (5S)-5-((4S)-2-((benzyloxy)methyl)-1,3-dioxolan-4-yl)-3,4-dihydroxyfuran-2(5H)-one (Tr-2)

L-Ascorbic acid (44.9 g, 0.255 mol) was added to a solution of compound Tr-1 (60 g, 0.306 mol) in dry acetonitrile (898 mL) followed by addition of pTSA monohydrate (15.5 g, 0.076 mol) and the reaction mixture was heated at 90° C. for 1 h. After completion of the reaction (TLC), half the volume of the acetonitrile was distilled off and the process was repeated twice. Solvent was removed completely and the title compound as a mixture of stereoisomers was obtained (91 g). The product was directly taken to the next step without further purification.

Step 3) (2R)-2-((4S)-2-((benzyloxy)methyl)-1,3-dioxolan-4-yl)-2-hydroxyacetic acid (Tr-3)

Compound Tr-2 (91.7 g, 0.297 mol) was added to a stirred solution of K$_2$CO$_3$ (86.3 g, 0.625 mol) in H$_2$O (509 mL) at room temperature. H$_2$O$_2$ (80 mL, 0.71 mol, 30% v/v) was slowly added and the solution was cooled to 0° C. and then stirred for 24 h. The solvent was removed under reduced pressure, EtOH (100 mL) was added and the mixture was heated at reflux for 30 min, then filtered. EtOH (100 mL)

was added to the afforded solid residue and the mixture was heated at reflux for 30 min (twice). The collected filtrates was concentrated under vacuum which gave the title compound (90 g) as a solid.

Step 4) (2S,4S)-2-((benzyloxy)methyl)-1,3-dioxolane-4-carboxylic acid (Tr-4a) & (2R,4S)-2-((benzyloxy)methyl)-1,3-dioxolane-4-carboxylic acid (Tr-4b)

Sodium hypochlorite (650 ml, 0.881 mol, 9-10% in water) was added drop wise over a period of 30 min to a vigorously stirred solution of compound Tr-3 (90 g, 0.294 mol) and $RuCl_3.xH_2O$ (1.22 g, 0.0058 mol) in water (ml pH=8 room temperature). The pH was maintained at 8 by addition of 1M NaOH solution. The reaction mixture was stirred for 3 h in room temperature then heated at 35° C. for 12 h. After completion of the reaction (TLC), 1.5 N HCl was added to the reaction mixture at 0° C. until pH 6 was reached, then EtOAc (1 L) was added. The organic phase washed with brine (2×100 mL), dried ($Na_2SO_4$), filtered and concentrated. The afforded crude was purified by silica gel column chromatography on 230-400 silica as 20% EtOAc in P.ether which gave compounds 4a+4b as a mixture of isomers. The isomers were then separated by column chromatography on silica 230-400 using 0.9% MeOH in DCM and 0.1% AcOH as an eluent, which gave the 2R isomer (20 g, 28%)

Step 5) (2S)-2-((benzyloxy)methyl)-1,3-dioxolan-4-yl acetate (Tr-5)

To a solution of compound Tr-4a (33 g, 0138 mol) in acetonitrile (660 mL) was added pyridine (13.2 ml) and lead acetate (79.8 g, 0.180 mol) and the mixture was stirred at room temperature for 16 h. After completion of the reaction (TLC) the reaction mixture was filtered, the filtrate was concentrated and the residue was taken in EtOAc (500 mL), washed with water (100 mL) and sat. sodium chloride solution (100 mL) and dried over $Na_2SO_4$. After removal of the solvent the crude was purified by column chromatography on 60-120 silica as 12-15% EtOAc/Pet.ether gradient which gave the title compound (16 g, 47%) as a liquid.

Step 6) (2S)-2-(hydroxymethyl)-1,3-dioxolan-4-yl acetate (Tr-6)

To a stirred solution of compound Tr-5 (16 g,) in dry methanol (160 mL), Pd/C (3.2 g, 20% w/w) was added the reaction mixture was hydrogenated for 3 h. After completion of the reaction (TLC), the reaction mixture was filtered through celite. The filtrate was concentrated under reduced pressure and the afforded crude title compound (10 g, 97%) was taken directly to the next step.

Step 7) ((2S)-4-acetoxy-1,3-dioxolan-2-yl)methyl acetate (Tr-7)

To a stirred solution of compound Tr-6 (5.74 g, 0.0354 mol) in pyridine (107 ml), acetic anhydride (8.22 ml, 0.080 mol) was added at 0° C. and the reaction mixture was stirred at room temperature for 16 h. After completion of the reaction (TLC), the reaction mixture was quenched with dil.HCl (10 ml) and extracted to EtOAc (100 mL). The organic phase was separated, dried ($Na_2SO_4$), filtered and concentrated. The afforded crude was purified by column chromatography on 230-400 silica eluted with a gradient of 10-15% EtOAc/Pet.ether which gave the title compound (4.97 g, 68%) as a liquid.

Step 8) ((2S,4S)-4-(4-(benzylamino)-2-oxopyrimidin-1(2H)-yl)-1,3-dioxolan-2-yl)methyl acetate (Tr-8a)

A mixture of N-benzoylcytosine (12.1 g, 56.3 mmol), ammonium sulfate (catalytic amount) and hexamethyldisilazane (HMDS) (67.4 ml, 418 mmol) were refluxed for 1 h. The HMDS was removed under reduced pressure at 40° C. and the residue was taken in dry 1, 2-dichloroethane (57 ml) and added the solution of compound Tr-7 (5.7 g, 27.9 mmol) in dry 1,2-dichloroethane (57 ml) followed by drop-wise addition of TMSOTf (10.2 ml, 45.7 mmol). The reaction mixture was stirred at room temperature for 1 h, then aqueous $NaHCO_3$ solution was added and the mixture was stirred for 30 min. The resulting solid was filtered through celite and the filtrate was taken in EtOAc (200 mL), washed with water (50 mL) and dried ($Na_2SO_4$). After removal of the solvent under reduced pressure the crude was purified by column chromatography on 230-400 silica using a gradient of 10-15% EtOAc/Pet.ether to afford a mixture of anomers which was further separated by SFC purification to afford the title compound (3 g, 30%) as a white solid.

Step 9) 4-amino-1-((2S,4S)-2-(hydroxymethyl)-1,3-dioxolan-4-yl)pyrimidin-2(1H)-one (Tr-9)

A mixture of compound Tr-8a (3 g), saturated methanolic ammonia solution (180 ml) was stirred at room temperature in a sealed tube for 16 h. After completion of the reaction (TLC), solvent was removed under reduced pressure and the crude was purified by column chromatography on 230-400 silica eluted with a gradient of 10-13% MeOH in DCM, which gave the title compound (1.5 g, 85%) as a solid.

$^1$H NMR 400 MHz DMSO-$d_6$ δ: 3.63-3.65 (2H), 4.04-4.07 (2H), 4.92-4.94 (1H), 5.18-5.21 (1H), 5.72-5.74 (1H), 6.16-6.18 (1H), 7.14 (1H), 7.26 (1H), 7.80-7.82 (1H).

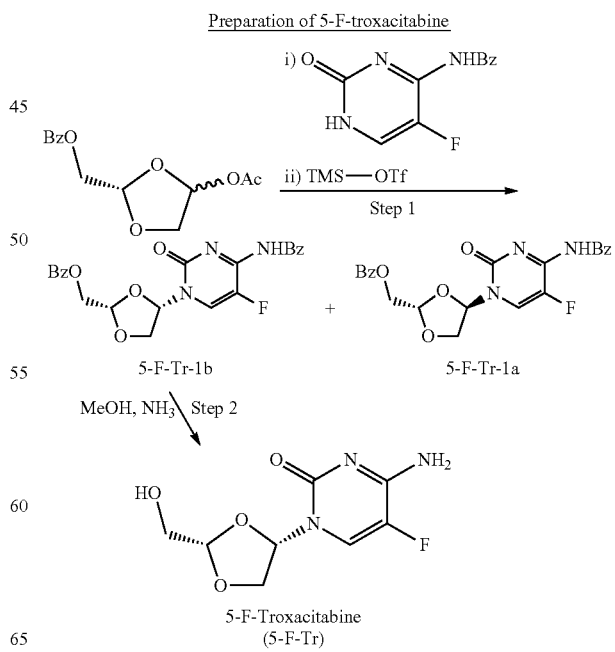

Preparation of 5-F-troxacitabine

Step 1) ((2S,4R)-4-(4-benzamido-5-fluoro-2-oxopyrimidin-1(2H)-yl)-1,3-dioxolan-2-yl)methyl benzoate (5-F-Tr-1a) & (2S,4S)-4-(4-benzamido-5-fluoro-2-oxopyrimidin-1(2H)-yl)-1,3-dioxolan-2-yl)methyl benzoate (5-F-Tr-1b)

A mixture of 5-fluoro benzoyl cytosine (9.1 g, 39.5 mmol), ammonium sulfate (catalytic amount) and hexamethyldisilazane (140 ml) was refluxed for 14 h. The HMDS was removed under reduced pressure at 40° C. and the residue was taken in dry 1,2-dichloroethane (50 ml) and added the solution of compound ((2S)-4-acetoxy-1,3-dioxolan-2-yl)methyl benzoate (7 g, 26.30 mmol) in dry 1,2-dichloroethane (50 ml) followed by the drop-wise addition of TMS-OTf (11.6 g, 52.6 mmol). The reaction mixture was stirred at room temperature for 2 h, then aqueous NaHCO₃ solution was added to the reaction mixture and the mixture was stirred for an additional 30 min. The resulting solid was filtered through celite and the filtrate was taken in EtOAc (500 mL), washed with water (50 mL) and dried (Na$_2$SO$_4$). The solvent was removed under reduced pressure and the crude was purified by column chromatography on 230-400 silica as 50-60% EtOAc/Pet.ether gradient to afford pure title compound (1.7 g, 18%) as a solid.

Step 2) 4-amino-5-fluoro-1-((2S,4S)-2-(hydroxymethyl)-1,3-dioxolan-4-yl)pyrimidin-2(1H)-one (5-F-Tr)

A mixture of compound 5-F-Tr-1b (1.7 g), saturated methanolic ammonia solution (34 ml) was stirred at room temperature in a sealed tube for 16 h, then the solvent was removed under reduced pressure and the crude was purified by column chromatography on 230-400 silica as 5% MeOH in DCM gradient to afford the title compound (0.8 g, 68%) as a solid.

The following phenols were prepared and used in the preparation of intermediates to the compounds of the invention:

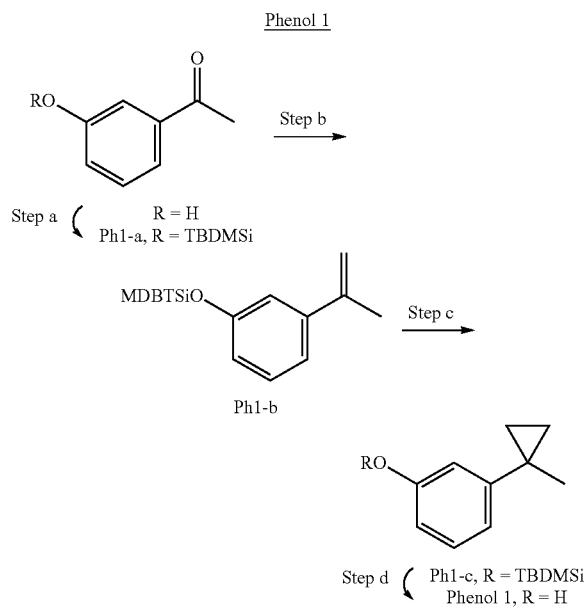

Phenol 1

Step a) 1-(3-((Tert-butyldimethylsilyl)oxy)phenyl)ethanone (Ph1-a)

Imidazole (4.46 g, 65.5 mmol) was added to a solution of 3-hydroxyacetophenone (4.46 g, 32.8 mmol) in DMF (6 mL). After 5 min, a solution of TBDMS-Cl (4.69 g, 31.1 mmol) in DMF (4 mL) was added. The reaction mixture was stirred at room temperature for 90 min, then poured into hexane containing 5% EtOAc (200 mL) and washed with 1M HCl (60 mL), water (60 mL), saturated sodium bicarbonate (2×60 mL), water (60 mL) and brine (60 mL). The organic layer was dried over Na$_2$SO$_4$, filtered and concentrated and the afforded residue was purified by flash chromatography on silica gel eluted with hexane/EtOAc, which gave the title compound (5.7 g, 69%).

Step b) Tert-butyldimethyl(3-(prop-1-en-2-yl)phenoxy)silane (Ph1-b)

Methyl(triphenylphosphonium)bromide (10.2 g, 28.4 mmol) was suspended in dry THF (30 mL) under nitrogen and the suspension was cooled to 0° C. n-Butyllithium (17.8 mL, 28.4 mmol) was added drop-wise to the mixture and the resulting solution was stirred at room temperature for 30 min. Ph1-a (5.7 g, 22.8 mmol) was added to the mixture and the reaction allowed to proceed at room temperature for 60 min. The reaction was quenched with aqueous sodium bicarbonate and extracted with diethyl ether (50 mL). The organic layer was washed with sodium bicarbonate solution, dried (Na$_2$SO$_4$), filtered and concentrated. The afforded residue was purified through a plug of silica-gel using eluted with hexane, which gave the title compound (3.9 g, 69%).

Step c) tert-butyldimethyl(3-(1-methylcyclopropyl)phenoxy)silane (Ph1-c)

Diethylzinc in hexane (439.2 mmol) was added drop-wise under nitrogen during 10 minutes to a cooled (0° C.) solution of the olefin Ph1-b (3.9 g, 15.7 mmol) in 1,2-dichloroethane (60 mL). Diiodomethane (6.32 mL, 78.5 mmol) was added drop-wise and the resulting mixture was stirred at 0° C. for 30 min and then allowed to attain room temperature overnight. The mixture was poured into an ice-cold solution of ammonium chloride and extracted with diethyl ether. The organic layer was washed with saturated sodium bicarbonate, dried (Na$_2$SO$_4$), filtered and concentrated. The crude was taken into hexane and the remaining diiodomethane was discarded. The hexane layer was concentrated to a crude that was taken into the next step without further purification.

Step d) 3-(1-Methylcyclopropyl)phenol (Phenol 1)

Ph1-c (3.45 g, 13.1 mmol) was taken into 1M solution of tetrabutylammonium fluoride in THF (20 mL, 20 mmol) and the resulting solution was stirred at room temperature overnight. The reaction was quenched with 1M HCl (50 mL) and extracted with ethyl acetate (100 mL). The organic layer was washed with brine (2×50 mL), dried (Na$_2$SO$_4$), filtered and concentrated. The residue was purified by flash chromatography on silica gel eluted with a mixture of 2-propanol, EtOAc and hexane, which gave the title compound (0.56 g, 29%). MS 147.1 [M–H]⁻.

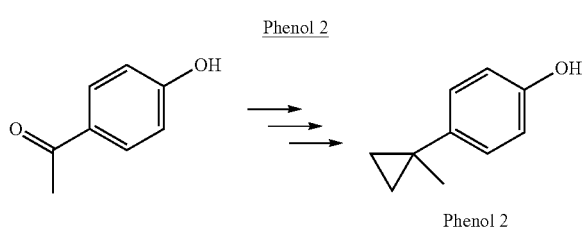

The title compound was prepared from 4-hydroxyacetophenone (6.0 g, 44.1 mmol) using the method described for the preparation of Phenol 1. Yield 53%.

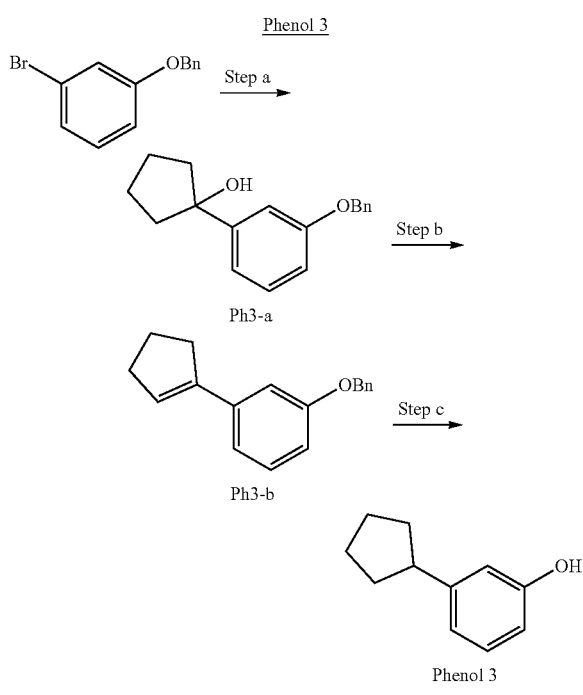

Step a) 1-(3-(benzyloxy)phenyl)cyclopentanol (Ph3-a)

Iodine, warmed up with magnesium, was added to a suspension of magnesium tunings (1.29 g, 52.8 mmol) in dry THF (50 mL). The mixture was refluxed and about 5% of a solution of 3-bromophenol (13.9 g, 52.8 mmol) was added. When the reaction had started, the solution of the bromide was added drop-wise and the mixture was then refluxed for one more hour. The mixture was cooled down to about 5° C. and a solution of the cyclopentanone (4.44 g, 52.8 mmol) in THF (50 mL) was added drop-wise. The mixture was stirred at rt for 72 h, then the reactio was quenched with cooled saturated ammonium chloride solution and extracted with diethyl ether (×3). The organic phase was washed with brine, dried (Na₂SO₄), filtered and concentrated. The product was purified by silica gel chromatography (isohexane/EtOAc), which gave the title compound (8.5 g, 54%).

Step b) 1-(benzyloxy)-3-(cyclopent-1-en-1-yl)benzene (Ph3-b)

p-Toluenesulfonic acid was added to a solution of Ph3-a (8.4 g, 28.2 mmol) in benzene (100 mL). The mixture was refluxed for three hours with a DMF trap, then cooled to rt, diluted with diethyl ether and washed with a saturated solution of sodium hydrogen carbonate and brine. The organic phase was dried (Na₂SO₄), filtered and concentrated. The product was purified by silica gel chromatography (isohexane/EtOAc), which gave the title compound (6.45 g, 91%). MS 249.4 [M−H]⁻.

Step c) 3-Cyclopentylphenol (Phenol 3)

A solution of Ph3-b (6.4 g, 26 mmol) in EtOAc (75 mL) and EtOH (75 mL) was hydrogenated at 22° C. and 40PSI in the presence of 10% Pd on carbon (1.5 g) in a Parr overnight. The catalyst was filtered off and washed with EtOAc and EtOH. The solvent was evaporated under reduced pressure and the product was isolated by silica gel chromatography (isohexane/EtOAc), which gave the title compound (3.6 g, 82%). MS 161.2 [M−H]⁻.

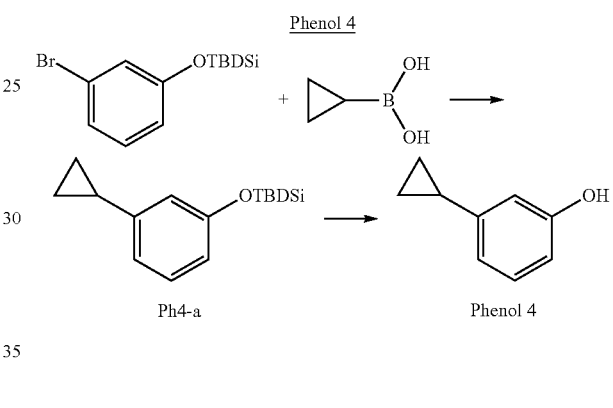

Step a) Tert-butyl(3-cyclopropylphenoxy)dimethylsilane (Ph4-a)

A suspension of (3-bromophenoxy)(tert-butyl)dimethylsilane (5.46 g, 19 mmol), cyclopropylboronic acid (2.12 g, 24.7 mmol), potassium phosphate, tribasic (14.1 g, 66.5 mmol), tricyclohexylphosphine (0.53 g, 1.9 mmol) and Pd(OAc)₂ (0.21 g, 0.95 mmol) in toluene (80 mL) and water (4 mL) was stirred at 110° C. overnight. The slurry was diluted with diethyl ether and washed with water and brine. The organic phase was dried (MgSO₄), filtered and concentrated. The crude was purified by flash column chromatography (EtOAc/hexane) which gave the title compound (1.94 g, 41%).

Step b) 3-Cyclopropylphenol (Phenol 4)

1M tetrabutylammonium fluoride (10.1 ml, 10.1 mmol) was added to a solution of Ph4-a (1.94 g, 7.81 mmol) in THF (25 ml). The solution was stirred for 2 hours, then the solvent was evaporated and the residue dissolved in EtOAc and washed twice with concentrated NH₄Cl (aq) and once with brine. The organic phase was dried (MgSO₄), filtered and concentrated. The crude was purified by flash column chromatography (hexane/ethyl acetate 9:1 with 1% isopropanol) which gave slightly impure title compound (1.24 g, 119%).

Phenol 5

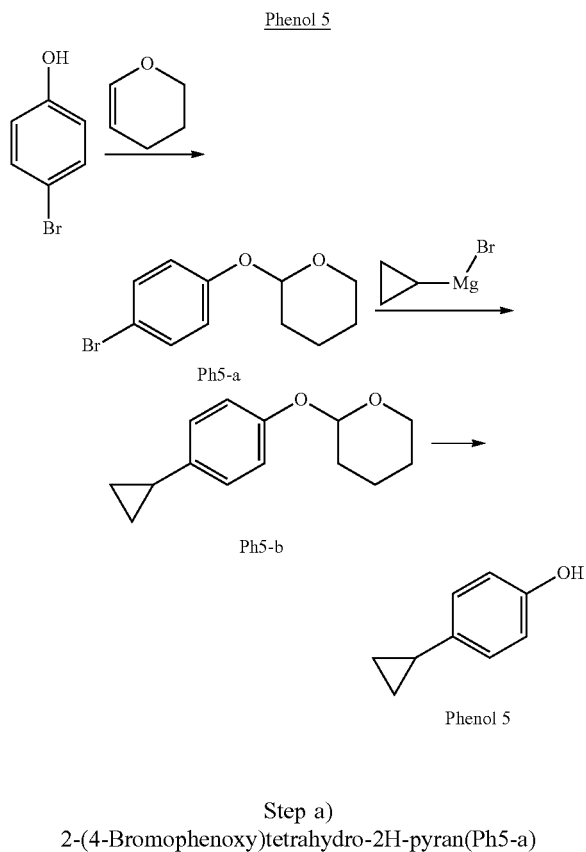

Step a) 2-(4-Bromophenoxy)tetrahydro-2H-pyran(Ph5-a)

4-Bromphenol (3.75 g, 21.7 mmol) was dissolved in 3,4-dihydro-2H-pyran (16 ml, 175 mmol), a catalytic amount of p-Toluenesulfonic acid (15 mg, 0.09 mmol) was added and the mixture was stirred at 22° C. for 45 min. The mixture was diluted with diethyl ether and washed with 1 M NaOH (aq) ×2, water, dried (Na$_2$SO$_4$) and concentrated which gave the title compound (5.57 g, 99%).

Step b) 2-(4-Cyclopropylphenoxy)tetrahydro-2H-pyran (Ph5-b)

A solution of 0.5 M cyclopropyl magnesium bromide in THF (6.5 ml, 3.25 mmol) was added during 15 min to a solution of Ph5-a (552.5 mg, 2.15 mmol), ZnBr (144 mg, 0.64 mmol), tri-tert-butylphosphine tetrafluoroborate (35.6 mg, 0.12 mmol) and Pd(OAc)$_2$ (29.5 mg, 0.13 mmol) in THF (4 ml). The mixture was stirred at 22° C. for 90 min then cooled on an ice bath and ice water (10 ml) was added. The mixture was extracted with EtOAc ×3 and the extracts washed with brine and then dried (Na$_2$SO$_4$), filtered and concentrated. The residue was purified by column chromatography on silica (petroleum ether/EtOAc) which gave the title compound (292 mg, 62%).

Step c) 4-Cyclopropylphenol (Phenol 5)

p-Toluenesulfonic acid monohydrate (18.9 mg, 0.1 mmol) was added to a solution of Ph5-b (2.28 g, 10.45 mmol) in MeOH (15 ml). The mixture was heated at 120° C. for 5 min in a microwave reactor, then concentrated and purified by column chromatography on silica (petroleum ether/EtOAc). The afforded solids were crystallized from petroleum ether which gave the title compound (1.08 g, 77%).

Phenol 6

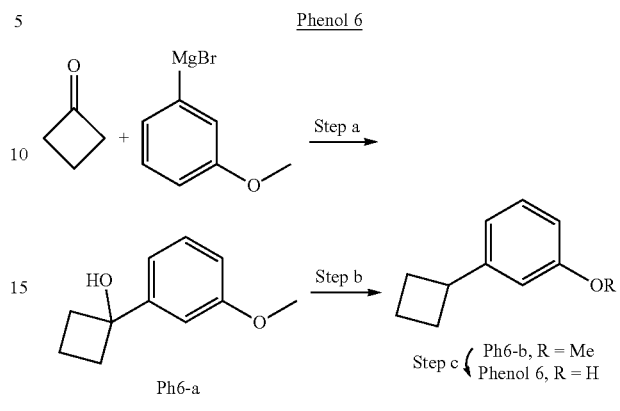

Step a) 1-(3-Methoxyphenyl)cyclobutanol (Ph6-a)

A 1 M solution of 3-methoxyphenyl magnesium bromide in THF (2.11 g, 99.8 mmol) was added dropwise between 0 and 10° C. to a stirred solution of cyclobutanone (6.66 g, 95 mmol) in diethyl ether (65 mL). The mixture was stirred for three hours at 0-10° C., then the mixture was added to an ice cooled solution of saturated NH$_4$Cl (300 mL) and water (300 mL). The mixture was stirred for 10 min then extracted three times with diethyl ether. The organic phase was dried, (Na$_2$SO$_4$), filtered and concentrate. The afforded crude product was purified by silica gel chromatography (isohexane/EtOAc), which gave the title compound (16.9 g, 86%).

Step b) 1-cyclobutyl-3-methoxybenzene (Ph6-b)

10% Pd on carbon (2.5 g) was added to a solution of Ph6-a (15.4 g, 86.1 mmol) in ethanol (200 mL) and the mixture was hydrogenated in a Parr at 60 psi. After 18 h, additional 10% Pd on carbon (1.5 g) was added and the mixture was hydrogenated for further 18 hours at 60 psi. The catalyst was filtered of and washed with EtOH and EtOAc. The solution was concentrated under reduced pressure and the crude product was isolated by silica gel chromatography (isohexane/EtOAc), which gave the title compound (14.0 g, 77%).

Step c) 3-cyclobutylphenol (Phenol 6)

A solution of 1M boron tribromide (18.1 g, 72.2 mmol) in DCM was added dropwise at 0° C. to a solution of Ph6-b (10.6 g, 65.6 mmol) in dry DCM (65 mL). The mixture was stirred for 2.5 hours at −5° C., then the reaction was quenched with cooled saturated solution of NH$_4$Cl and extracted three times with DCM. The organic phase was dried (Na$_2$SO$_4$), filtered and concentrate. The afforded crude product was purified by silica gel chromatography (isohexane/EtOAc), which gave the title compound (9.73 g, 88%).

Phenol 7

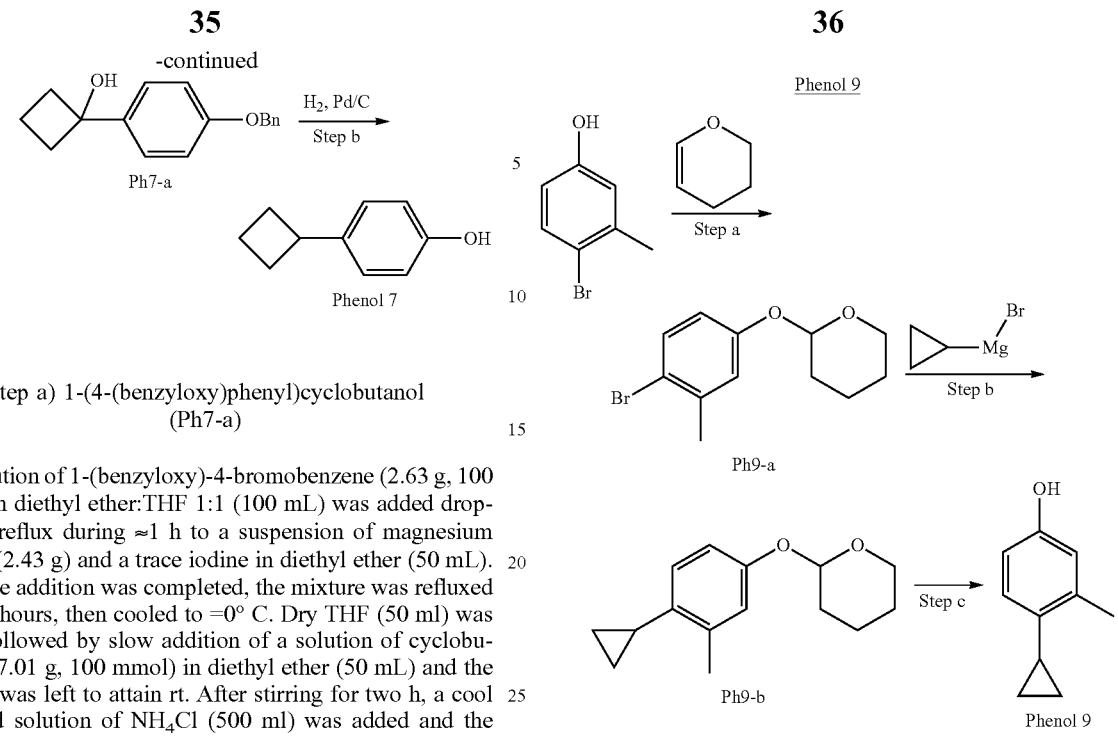

Step a) 1-(4-(benzyloxy)phenyl)cyclobutanol (Ph7-a)

A solution of 1-(benzyloxy)-4-bromobenzene (2.63 g, 100 mmol) in diethyl ether:THF 1:1 (100 mL) was added dropwise at reflux during ≈1 h to a suspension of magnesium tunings (2.43 g) and a trace iodine in diethyl ether (50 mL). When the addition was completed, the mixture was refluxed for four hours, then cooled to =0° C. Dry THF (50 ml) was added followed by slow addition of a solution of cyclobutanone (7.01 g, 100 mmol) in diethyl ether (50 mL) and the mixture was left to attain rt. After stirring for two h, a cool saturated solution of $NH_4Cl$ (500 ml) was added and the mixture was stirred for 15 minutes, then extracted twice with EtOAc. The organic phase was washed with brine, dried with sodium sulfate and evaporated under reduced pressure. The product was purified by column chromatography on silica gel, which gave the title compound (12.5 g, 42%).

Step b) 4-cyclobutylphenol (Phenol 7)

Pd 10% on carbon (2.55 g, 21.5 mmol) was added under argon to a solution of Ph7-a (12.4 g, 41.4 mmol) in abs EtOH (110 mL) the and the mixture was hydrogenated at 45 psi at rt for 18 h. The catalyst was filtered of, washed with ethanol and the solution was concentrated. The product was purified by silica gel chromatography (isohexane-EtOAc). Appropriate fractions were pooled and concentrated and the residue crystallized from petrol ether which gave the title compound (3.15 g, 51%).

Phenol 8

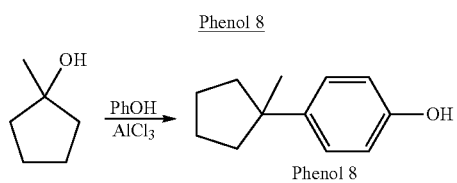

4-(1-Methylcyclopentyl)phenol (Phenol 8)

A solution of 1-methylcyclopentanol (2.00 g, 20.0 mmol) and phenol (2.07 g, 22.0 mmol) in pentane (50 mL) were added dropwise during 30 min to a suspension of fresh $AlCl_3$ (1.33 g, 10 mmol) in pentane (100 mL). The resulting mixture was stirred under $N_2$ at rt for 72 h, then the reaction mixture was poured into water/ice and HCl (12 M, 20 mmol, 1.66 mL). The organic phase was washed with water (50 mL) and brine (50 mL), dried ($Na_2SO_4$) filtered and concentrated. The crude was purified by column chromatography on silica (MeOH-DCM), which gave the title compound (426 mg, 12%).

Step a) 2-(4-Bromo-3-methylphenoxy)tetrahydro-2H-pyran (Ph9-a)

pTs (16 mg, 0.086 mmol) was added to a solution of 4-bromo-3-methylphenol (4.0 g, 21.4 mmol) in 3,4-dihydro-2-H-pyran (16 mL, 175 mmol). The reaction mixture was stirred at room temperature for 1 h, then diluted with diethyl ether and washed with 1M NaOH (aq) and water. The organic phase was dried ($Na_2SO_4$) filtered and concentrated. The crude was purified by column chromatography on silica (EtOAc/heptane) which gave the title compound (3.32 g, 57%).

Step b) 2-(4-Cyclopropyl-3-methylphenoxy)tetrahydro-2H-pyran (Ph9-b)

Ph9-a (3.12 g, 11.5 mmol), $ZnBr_2$ (2.59 g, 11.5 mmol), tri-tert-butylphosphine tetrafluoroborate (0.2 g, 0.69 mmol) and $Pd(OAc)_2$ (258 mg, 1.15 mmol) were put in a flask and the flask was flushed with $N_2$ a couple of times. THF (10 mL) was added while stirring, followed by dropwise addition of 0.5 M cyclopropylmagnesium bromide in THF (35 mL, 17.4 mmol) during 5 minutes. The mixture was stirred at rt on, then filtered through a Celite plug, eluted with MeOH. The solution was concentrates and the crude was purified by column chromatography on silica (EtOAc/heptane) which gave the title compound (1.69 g, 57%).

Step c) 4-Cyclopropyl-3-methylphenol (Phenol 9)

Ph9-b (1.70 g, 7.30 mmol) was dissolved in MeOH (20 ml) and $pTsxH_2O$ (318 mg, 1.67 mmol) was added. The mixture was stirred at 22° C. for 30 minutes, then concentrated. The crude was purified by column chromatography (EtOAc/heptane), which gave the title compound (704 mg, 65%).

Phenol 10

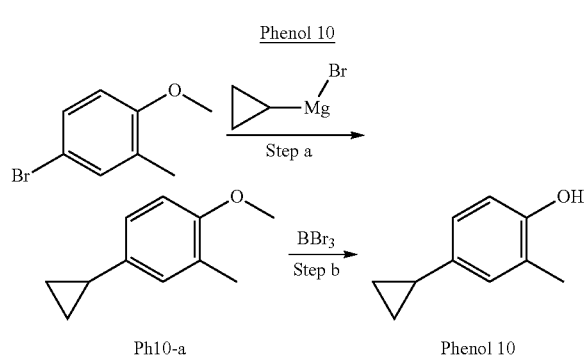

Step a) 4-cyclopropyl-1-methoxy-2-methylbenzene (Ph10-a)

4-Bromo-1-methoxy-2-methylbenzene (4.39 g, 21.9 mmol) was reacted with cyclopropylmagnesium bromide according to the procedure described in Ph9 step b, which gave the title compound (1.54 g, 43%).

Step b) 4-cyclopropyl-2-methylphenol (Phenol 10)

BBr$_3$ (5 mL, 5 mmol) was added under N$_2$ at 0° C. to a solution of Ph10-a (1.54 g, 9.49 mmol) in DCM (7.5 mL). The reaction was stirred for 2 h, then quenched with MeOH (3 mL) and concentrated. The crude was dissolved in EtOAc and washed with brine. The organic phase was dried (Na$_2$SO$_4$), filtered and concentrated. The crude product was purified by column chromatography on silica, which gave the title compound (826 mg, 59%). MS 147.11 [M−H]$^-$.

Phenol 11

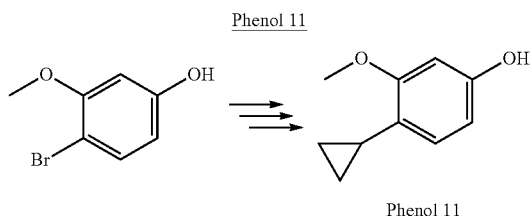

4-cyclopropyl-3-methoxyphenol (Phenol 11)

The title compound was prepared from 4-bromo-3-metoxyphenol (1.11 g, 5.49 mmol) according to the procedure described for the preparation of Phenol 9. Yield 40%.

Phenol 12

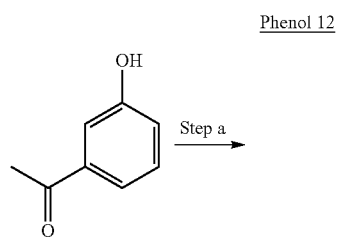

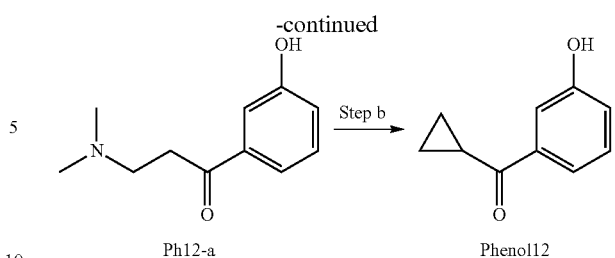

Step a) 3-(dimethylamino)-1-(3-hydroxyphenyl) propan-1-one (Ph12-a)

A few drops of HCl were added to a solution of 3-hydroxy acetophenone (4.08 g, 30 mmol), paraformaldehyde (4.05 g, 45 mmol) and dimethylamine hydrochloride (2.69 g, 33 mmol) in absolute EtOH (100 mL) and the reaction mixture refluxed for 18 h. Additional dimethylamine hydrochloride (0.55 eq., 1.22 g), paraformaldehyde (0.5 eq., 1.35 g) and HCl (0.5 mL) were added and the reaction mixture refluxed for additional 4 h, then cooled to rt. The precipitated white solid was collected and washed with cold EtOH (50 mL) and cold acetone (10 mL) and then freeze dried, which gave the title compound (2.59 g, 38%) that was used in the next step without further purification.

Step b) cyclopropyl(3-hydroxyphenyl)methanone (Phenol 12)

NaH (60% mineral oil dispersion) (1.13 g, 28.2 mmol) was added in portions at rt to a stirred suspension of trimethylsulfoxonium iodide (6.20 g, 28.2 mmol) in DMSO (100 mL). After 1 h, solid Ph12-a (2.59 g, 11.3 mmol) was added in portions under stirring and cooling. The reaction mixture was stirred at rt for 40 h, then poured into cold water (200 mL) and extracted with DCM (3×100 mL). The organic phase was washed with a saturated aqueous solution of NH$_4$Cl (2×100 mL), dried (Na$_2$SO$_4$), filtered and concentrated. The afforded crude was purified by column chromatography on silica (MeOH/DCM) which gave the title compound (883 mg, 48%).

Phenol 13

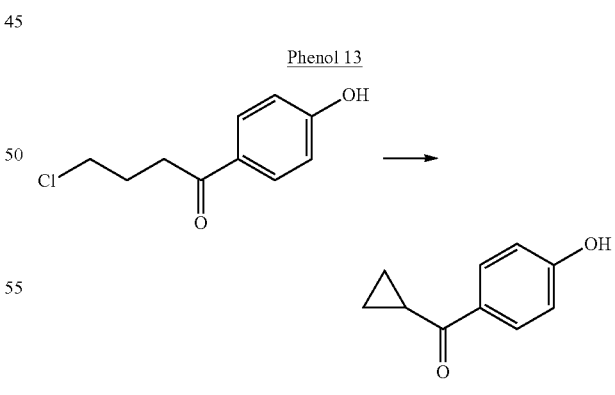

Step a) cyclopropyl(4-hydroxyphenyl)methanone (Ph13)

p-Hydroxy-γ-chlorobutyrophenone (4.95 g) was added in portions during approximately 30 min to a solution of NaOH (8 mL, aq, 50% w/w), then NaOH (35 mL, aq, 25% w/w) was added followed by p-hydroxy γ-chlorobutyrophenone (4.95 g) in one portion. The temperature was lowered to 140° C. and NaOH (8 g) was added. After 90 min, H$_2$O (10 mL) was added, and after additional 60 min, the reaction mixture was cooled, diluted with H$_2$O and neutralized with HOAc (≈27-30 ml) to pH ≈7 The formed precipitate was filtered, washed with H$_2$O and dried in vacuum. The solids were triturated in CHCl$_3$ (200 ml) at 40° C. during 10 min, then at RT overnight. The slurry was heated to 40° C. during 30 min, then filtered. The filtrate was dried (MgSO$_4$), filtered and concentrated to ≈70 ml. Hexane was added and an oil was formed that eventually became crystals. The slurry was filtered, solids washed with CHCl$_3$/hexane and dried, which gave the title compound (4.15 g, 51%).

Phenol 14

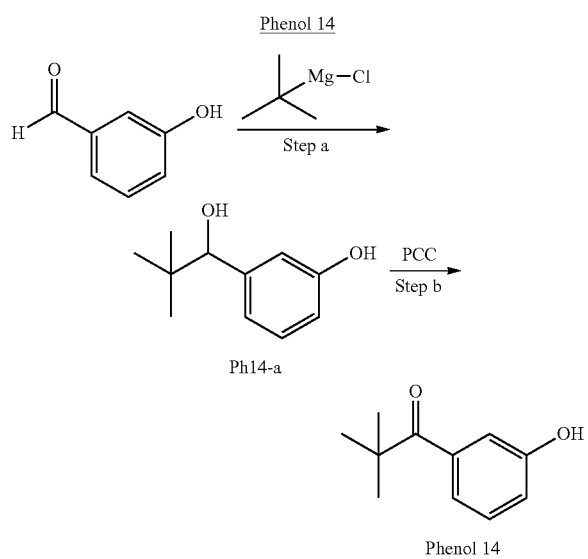

Ph14-a

Phenol 14

Step a) 3-(1-hydroxy-2,2-dimethylpropyl)phenol (Ph14-a)

t.Bu-MgBr (1.5 eq.) was added dropwise during 30 minutes to a cold (−10° C.) mixture of 3-hydroxybenzaldehyde (2.00 g, 16.4 mmol) in diethyl ether (20 mL). During the addition THF (20 mL) was added. The mixture was allowed to reach 23° C. and stirred for 6 hours. More t.Bu-MgBr (0.7 eq.) was added and the mixture was left stirring over night, then cooled and the reaction was quenched with aqueous saturated NH$_4$Cl. to give. EtOAc was added to the mixture followed by addition of 1 M aqueous HCl until a homogeneous mixture was obtained. The phases were separated and the organic phase was washed with brine, dried (Na$_2$SO$_4$), filtered and concentrated. The afforded crude was purified by column chromatography, which gave the title compound (1.1 g, 37%).

Step b) 1-(3-hydroxyphenyl)-2,2-dimethylpropan-1-one (Ph14)

To an oven dried round bottomed flask was added 3 Å MS and pyridinium chlorochromate (PCC) (1.97 g, 9.15 mmol) followed by dry DCM (5 mL). The mixture was stirred at 20° C. for 5 minutes whereafter a mixture of AA8019 (1.10 g, 6.10 mmol) in DCM (5 mL) was added slowly. After complete oxidation the mixture was filtered through a pad of Celite, washing the pad with diethyl ether. The filtrate was concentrated. The crude was purified by column chromatography which gave the title compound (402 mg, 37%). MS 179.25 [M+H]+.

Phenol 15

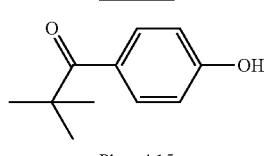

Phenol 15

1-(4-Hydroxyphenyl)-2,2-dimethylpropan-1-one (Ph15)

4-hydroxybenzaldehyde (3 g, 24.6 mmol) was reacted according to the procedure described for the preparation of Phenol 14, which gave the title compound (538 mg, 17%).

Amino Acid 1

Step a) (S)-(S)-sec-butyl 2-((tert-butoxycarbonyl)amino)propanoate (AA1-a)

L-Boc-Alanine (2.18 g, 11.5 mmol) was dissolved in dry DCM (40 mL) and the alcohol (R)-butan-2-ol (938 mg, 12.6 mmol) was added. The mixture was cooled to about 5° C. and EDC (3.31 g, 17.2 mmol) was added in one portion followed by portionwise addition of DMAP (140 mg, 1.15 mmol). The mixture was allowed to attain room temperature and stirred overnight, then diluted with ethyl acetate (~300 ml) and the organic phase was washed three times with a saturated solution of sodium hydrogen carbonate and once with brine. The organic phase was dried over sodium sulfate and concentrated under reduced pressure. The product was isolated by silica gel chromatography eluted with isohexane and 10% ethyl acetate, which gave the title compound (2.78 g, 98%).

Step b) (S)-(S)-Sec-butyl 2-aminopropanoate (AA1-b)

A mixture of AA1-a (2.77 g, 11.3 mmol) and p-toluene sulfonic acid mono hydrate (2.15 g, 11.3 mmol) in EtOAc (45 mL) was stirred for 16 h at 65° C., then concentrated under reduced pressure. The afforded residue was crystallised from diethyl ether, which gave the title compound (3.20 g, 89%).

Amino acid 2

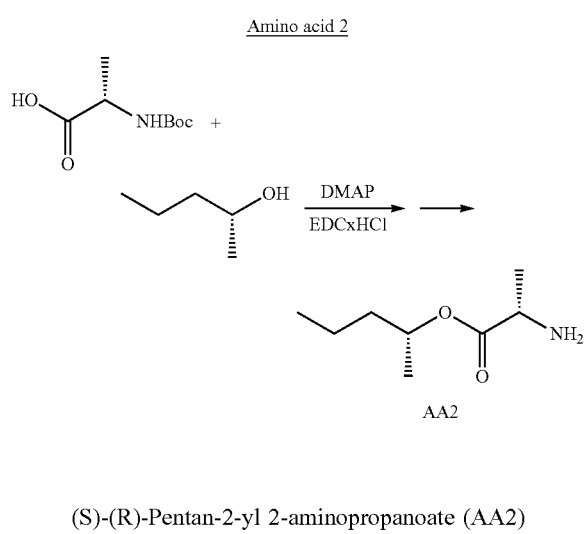

(S)-(R)-Pentan-2-yl 2-aminopropanoate (AA2)

The procedure described for the preparation of AA1 was followed but using (R)-pentan-2-ol instead of (R)-butan-2-ol, which gave the title compound (4.6 g).

Amino acid 3

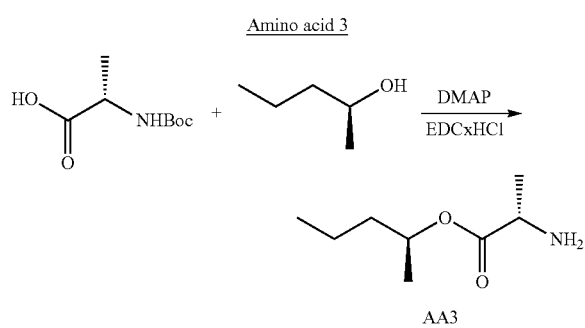

(S)-(S)-Pentan-2-yl 2-aminopropanoate (AA3)

The procedure described for the preparation of AA1 was followed but using (S)-pentan-2-ol instead of (R)-butan-2-ol, which gave the title compound (8.3 g).

The following intermediates were prepared and can be used in the preparation of compounds of the invention:

Intermediate 1

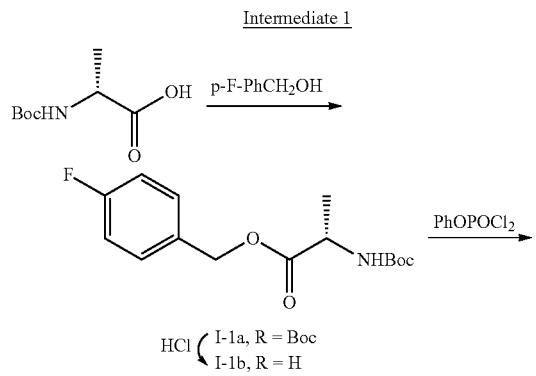

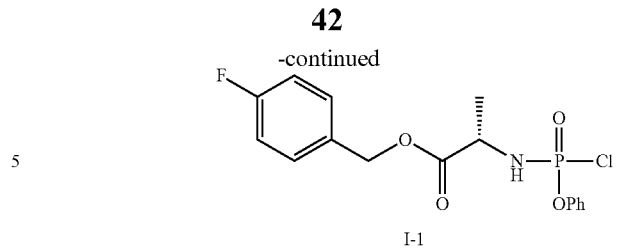

Step a) (R)-4-fluorobenzyl 2-((tert-butoxycarbonyl)amino)propanoate (I-1a)

Boc-L-AlaOH (19.92 mmol), DMAP (1.99 mmol) and (4-fluorophenyl)methanol (23.9 mmol) were dissolved in $CH_2Cl_2$ (100 mL). To this solution was added triethylamine (23.9 mmol) followed by EDCl (23.9 mmol) and the resulting reaction mixture was stirred overnight at room temperature under $N_2$. The reaction mixture was diluted with $CH_2Cl_2$ (100 mL), washed with saturated aqueous solution of $NaHCO_3$ (2×50 mL), saturated aqueous solution of NaCl (2×50 mL), dried ($Na_2SO_4$) and concentrated. The afforded residue was purified by column chromatography on silica gel eluted with n-hexane-EtOAc (95:5 to 60:40) which gave the title compound (4.44 g) as a white waxy solid. MS: 296 [M−H]⁻.

Step b) (R)-4-fluorobenzyl 2-aminopropanoate (I-1b)

Compound I-1a (14.93 mmol) was dissolved in 4M HCl/dioxane (40 mL) and stirred at room temperature for 30 minutes and evaporated to dryness which gave the hydrochloride salt of the title compound (3.4 g) as a white powder. MS: 198 [M+H]⁺.

Step c) (2R)-4-fluorobenzyl 2-((chloro(phenoxy)phosphoryl)amino)propanoate (I-1)

$PhOPOCl_2$ (4.28 mmol) was added dropwise at −78° C. to a solution of compound I-5b (4.28 mmol) in $CH_2Cl_2$. followed by dropwise addition of triethylamine (8.56 mmol). The resulting reaction mixture was stirred at −78° C. under Ar and allowed to attain room temperature overnight. The reaction mixture was evaporated on silica gel and purified by chromatography (n-hexane/EtOAc (88:12)-(0:100)). which gave the title compound (769 mg). ³¹P-NMR ($CDCl_3$) δ: 7.85 (s) and 7.54 (s) ($R_P$ and $S_P$ diastereomers).

Intermediate 2

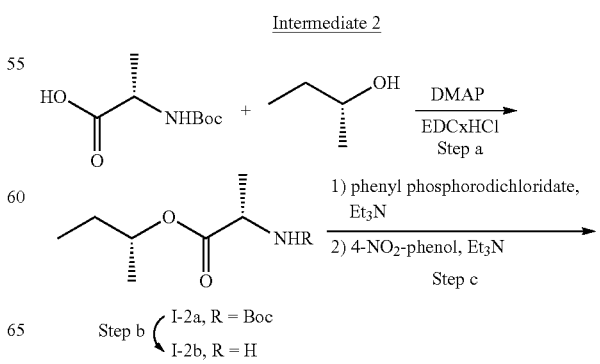

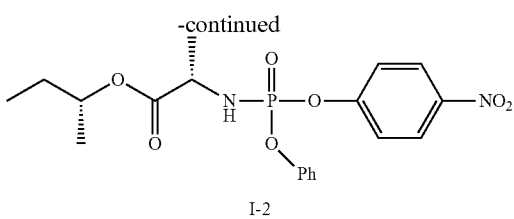

I-2

Step a) (S)-(R)-sec-butyl 2-((tert-butoxycarbonyl)amino)propanoate (1-2a)

L-Boc-Alanine (2.18 g, 11.5 mmol) was dissolved in dry DCM (40 mL) and the alcohol (R)-butan-2-ol (938 mg, 12.6 mmol) was added. The mixture was cooled to about 5° C. and EDC (3.31 g, 17.2 mmol) was added in one portion followed by portionwise addition of DMAP (140 mg, 1.15 mmol). The mixture was allowed to attain room temperature and stirred overnight, then diluted with ethyl acetate (~300 ml) and the organic phase was washed three times with a saturated solution of sodium hydrogen carbonate and once with brine. The organic phase was dried over sodium sulfate and concentrated under reduced pressure. The product was isolated by silica gel chromatography eluted with isohexane and 10% ethyl acetate, which gave the title compound (2.78 g, 98%).

Step b) (S)-(R)-Sec-butyl 2-aminopropanoate (I-2b)

A mixture of I-10a (2.77 g, 11.3 mmol) and p-toluene sulfonic acid mono hydrate (2.15 g, 11.3 mmol) in EtOAc (45 mL) was stirred for 16 h at 65° C., then concentrated under reduced pressure. The afforded residue was crystallised from diethyl ether, which gave the title compound (3.20 g, 89%).

Step c) (2S)—(R)-Sec-butyl 2-(((4-nitrophenoxy)(phenoxy)phosphoryl)amino)propanoate (I-2)

Phenyl dichlorophosphate (1 eq) was added under nitrogen at −30° C. to a solution of Compound I-10b (3.15 g, 9.92 mmol) in DCM (75 ml), followed by dropwise addition of triethylamine (2 eq). The mixture was allowed to attain room temperature and stirred overnight, then cooled to about 5° C. and 4-nitrophenol (1 eq, 15 mmol) was added as a solid followed by dropwise addition of triethylamine (1 eq g, 15 mmol) and the mixture was stirred for 4 hours at room temperature, then concentrated under reduced pressure, diluted with ethyl acetate (40 ml) and ether (40 ml) and left at room temperature overnight. The triethylamine-HCl salt was filtered of and the filtrate was concentrated under reduced pressure. The afforded residue was purified by column chromatography on silica gel eluted with isohexane-ethyl acetate, which gave the title compound (4.19 g, 79%).

The following compounds were prepared according to the procedure described for the preparation of I-2 using the appropriate alcohol:

| I-# | Structure | alcohol |
| --- | --- | --- |
| I-3 | 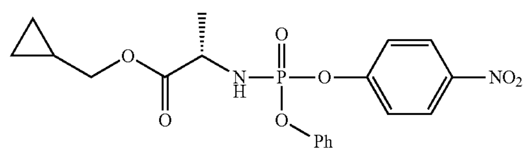 [SMILES: C[C@H](NP(=O)(Oc1ccccc1)Oc1ccc([N+](=O)[O-])cc1)C(=O)OCC1CC1] | cyclopropylmethanol |
| I-4 | 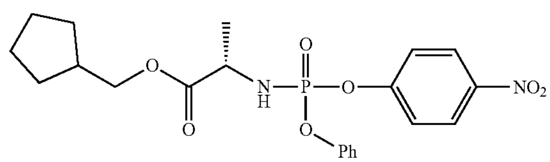 [SMILES: C[C@H](NP(=O)(Oc1ccccc1)Oc1ccc([N+](=O)[O-])cc1)C(=O)OCC1CCCC1] | cyclopentylmethanol |
| I-5 | 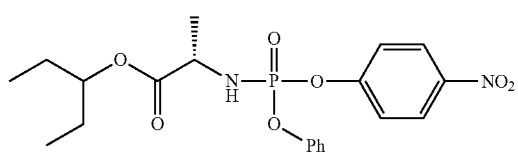 [SMILES: CCC(CC)OC(=O)[C@H](C)NP(=O)(Oc1ccccc1)Oc1ccc([N+](=O)[O-])cc1] | pentan-3-ol |
| I-6 | 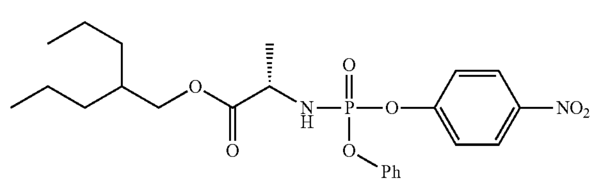 [SMILES: CCCC(CCC)COC(=O)[C@H](C)NP(=O)(Oc1ccccc1)Oc1ccc([N+](=O)[O-])cc1] | 2-propylpentan-1-ol |

Intermediate 6, Diastereomer-1 & -2

The two diastereomers of compound I-6 were separated by SFC, which gave I-6-dia-1 and I-6-dia-2.

Intermediate 7

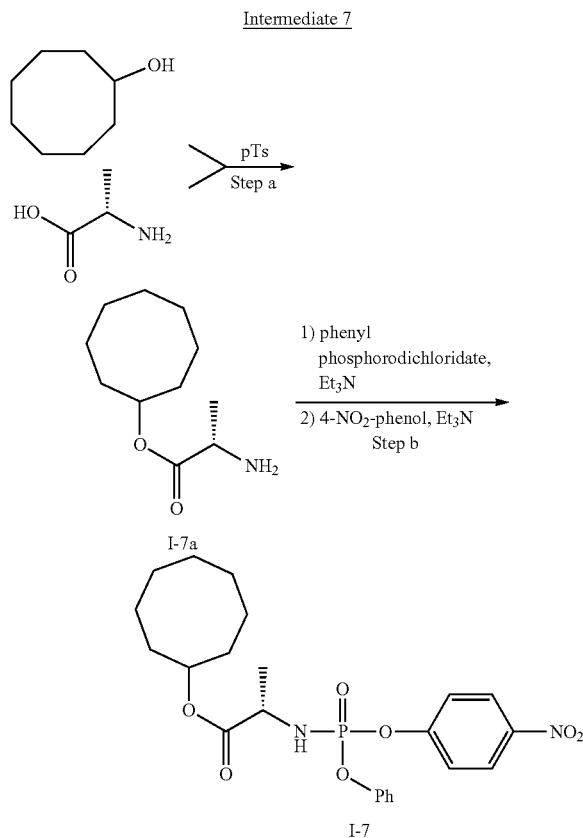

Step a) (S)-cyclooctyl 2-aminopropanoate (I-7a)

To a slurry of L-alanine (1.7 g, 19.1 mmol) and cyclooctanol (25 ml, 191 mmol) in toluene (100 ml) was added p-toluenesulfonic acid monohydrate (3.6 g, 19.1 mmol). The reaction mixture was heated at reflux temperature for 25 h and water was removed from the reaction using a Dean-Stark trap. The mixture was concentrated under reduced pressure and the residue kept under vacuum over night. To the residue (27 g) was added diethyl ether (100 ml). The white precipitate was collected by filtration, washed with diethyl ether (3×50 ml) and dried under vacuum which gave the title compound (4.84 g, 68%).

Step b) (2S)-cyclooctyl 2-(((4-nitrophenoxy)(phenoxy)phosphoryl)amino)propanoate (I-7)

Compound I-7a was reacted according to the method described for the preparation of I-2 step c, which gave the title compound (4.7 g, 76%)

Intermediate 8

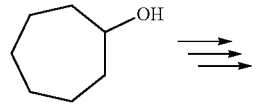

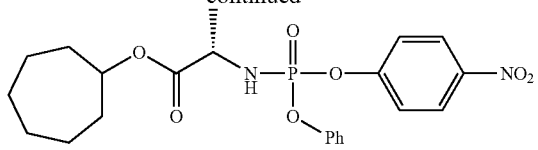

(2S)-cycloheptyl 2-(((4-nitrophenoxy)(phenoxy)phosphoryl)amino)propanoate (I-22)

The procedure described for the preparation of compound I-7 was followed but using cycloheptanol (27 ml, 224 mmol) instead of cyclooctanol, which gave the title compound (5.72 g, 55%).

Intermediate 9

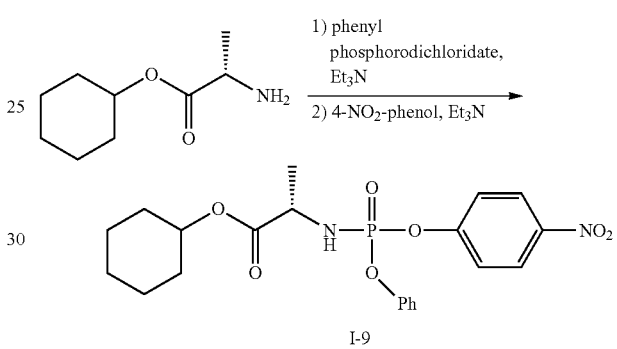

(2S)-Cyclohexyl 2-(((4-nitrophenoxy)(phenoxy)phosphoryl)amino)propanoate (I-23)

The procedure described for the preparation of 1-2 step c was followed but using (S)-cyclohexyl 2-aminopropanoate instead of (S)-3,3-dimethylbutyl 2-aminopropanoate, which gave the title compound (10.6 g, 82%).

Intermediate 10

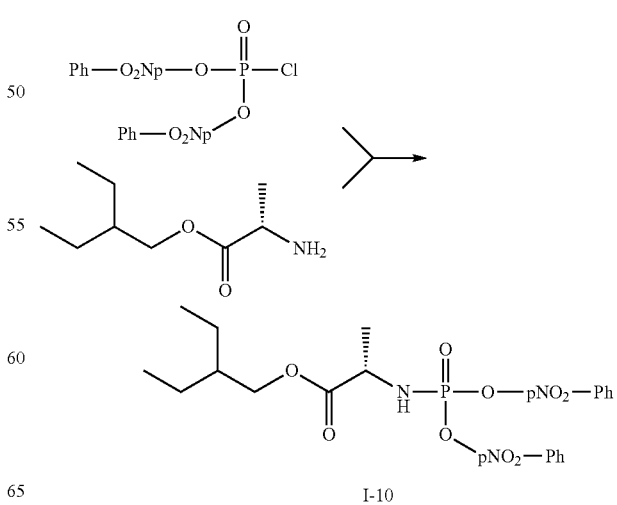

(S)-2-Ethylbutyl 2-((bis(4-nitrophenoxy)phosphoryl)amino)propanoate (I-10)

(S)-2-Ethylbutyl 2-aminopropanoate (5 g, 14.49 mmol) was added to a solution of bis(4-nitrophenyl) phosphorochloridate (6.14 g, 17.1 mmol) in DCM (50 ml), the mixture was cooled in an ice bath and Et$_3$N (4.77 mL, 34.2 mmol) was added drop wise. The cooling was removed after 15 min and the reaction mixture was stirred at 23° C. until complete reaction according to TLC. Diethyl ether was then added, the mixture was filtered and the filtrate was concentrated and purified by column chromatography on silica which gave the title compound (2.05 g, 82%).

Intermediate 11

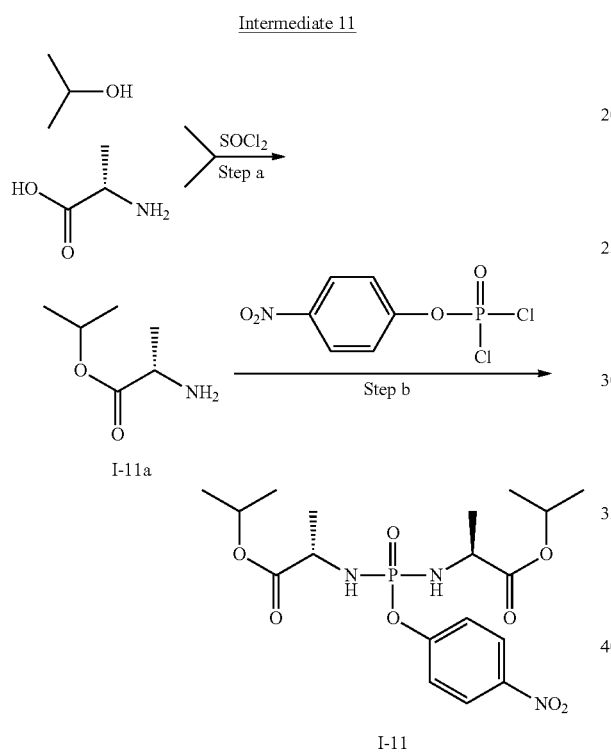

Step a) (S)-isopropyl 2-aminopropanoate (I-11a)

SOCl$_2$ (29 mL, 400 mmol) was added dropwise at 0° C. to a suspension of the HCl salt of L-alanine (17.8 g, 200 mmol) in isopropanol (700 mL). The suspension was stirred at room temperature over night, then concentrated, which gave the title compound (29.2 g, 87%).

Step b) (2S)-Isopropyl 2-(((((S)-1-isopropoxy-1-oxopropan-2-yl)amino)(4-nitrophenoxy)phosphoryl)-amino)propanoate (I-11)

A solution of 4-nitrophenyl dichlorophosphate (1.8 g 7 mmol) in DCM was added dropwise at −60° C. to a solution of the amine I-11a (2.35 g, 14 mmol) and triethylamine (7.7 mL, 56 mmol) in DCM. The reaction mixture was allowed to attain room temperature, stirred over night, concentrated and then diluted with ethyl acetate and ether and left at room temperature overnight. The triethylamine-HCl salt was filtered of, the filtrate was concentrated under reduced pressure and the afforded residue was purified by chromatography on silica gel eluted with iso-hexane-ethyl acetate, which gave the title compound (1.6 g, 50%).

Intermediate 12

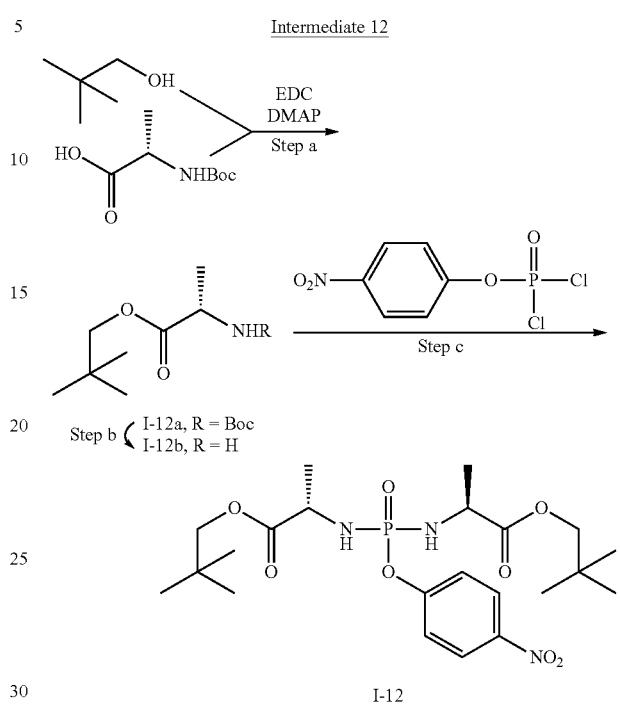

Step a) (S)-Neopentyl 2-((tert-butoxycarbonyl)amino)propanoate (I-12a)

EDAC and DMAP was added in portions at −5° C. to a solution of Boc-alanine (18.9 g, 100 mmol) and neopentylalcohol (13.0 mL, 120 mmol) in DCM (200 mL). The reaction mixture was allowed to attain room temperature and stirred for 72 h. EtOAc (700 mL) was added and the organic phase was washed three times with a saturated solution of NaHCO$_3$ and once with brine, then concentrated. The afforded residue was purified by column chromatography eluted with hexane-EtOAc 90/10 to 80/20, which gave the title compound (21 g, 81%).

Step b) (S)-Neopentyl 2-aminopropanoate (I-12b)

p-Toluene sulfonic acid (15.6 g, 82.0 mmol) was added at −65° C. to a solution of the Boc protected amine I-12a (21.1 g, 82.0 mmol) in EtOAc (330 mL). The reaction mixture was stirred at −65° C. for 8 h, then left to attain room temperature overnight. The mixture was then filtered and concentrated which gave the title compound (21 g, 78%).

(2S)-Neopentyl 2-(((((S)-1-(neopentyloxy)-1-oxopropan-2-yl)amino)(4-nitrophenoxy)-phosphoryl)amino)propanoate (I-12)

4-Nitrophenol dichlorophosphate was added dropwise during 1 h at −50° C. to a solution of the amine I-12b (3.90 g, 24.5 mmol) in DCM (100 mL). The reaction mixture was allowed to attain room temperature, stirred overnight, concentrated and then diluted with diethyl ether and left at room temperature overnight. The mixture was filtered, the filtrate was concentrated under reduced pressure and the afforded residue was purified by chromatography on silica gel eluted with iso-hexane-ethyl acetate, which gave the title compound (4.8 g, 77%).

Intermediate 32

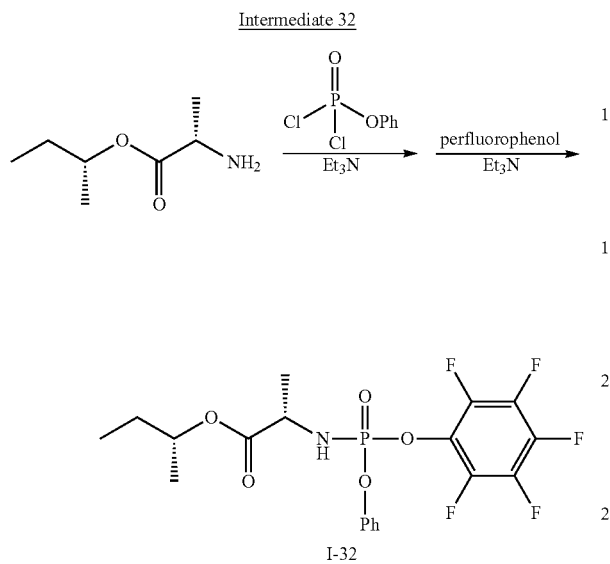

(2S)—(R)-sec-butyl 2-(((perfluorophenoxy)(phenoxy)phosphoryl)amino)propanoate (I-32)

Et$_3$N (10.9 mL, 78.1 mmol) was added dropwise at −70° C. under nitrogen during 15 minutes to a stirred solution of the pTs salt of (S)-(R)-sec-butyl 2-aminopropanoate (12.0 g, 37.7 mmol) in DCM (50 mL). To this mixture was added a solution of phenyl dichlorophosphate (5.61 mL, 37.7 mmol) in DCM (50 mL) during 1 h. The reaction mixture was stirred at −70° C. for additional 30 minutes, then allowed to warm to 0° C. during 2 h and stirred for 1 h. A solution of pentafluorophenol (6.94 g, 37.7 mmol) and Et$_3$N (5.73 mL, 41.1 mmol) in DCM (30 mL) was added to the mixture during 20 minutes. The crude mixture was allowed to stir at 0° C. for 18 h, and was then concentrated. The residue was taken in THF (100 mL), insolubles were filtered off and washed several times with THF. The solvent was evaporated and the residue triturated with tert.butyl methyl ether. Insolubles were filtered off and washed with tert.buty methyl ether. The combined filtrate was concentrated and the crude solid sonicated with n-hexane/EtOAc (80:20; 100 mL). The solid was filtered, washed with n-hexane/EtOAc (80:20) which gave the pure phosphorus stereoisomer of the title compound as a white solid (2.3 g, 13%).

Intermediate 33

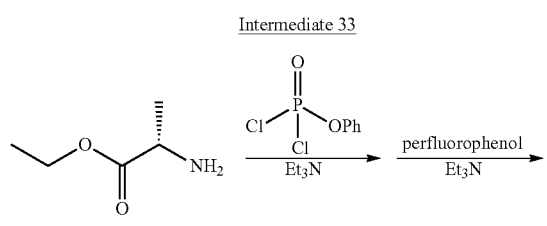

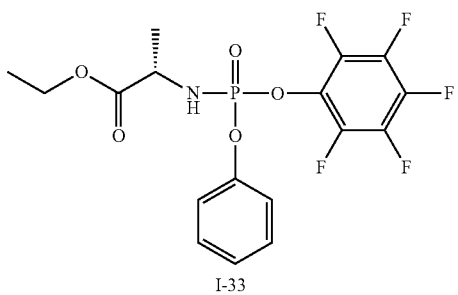

(2S)-ethyl 2-(((perfluorophenoxy)(phenoxy)phosphoryl)amino)propanoate (I-33)

The pure phosphorus stereoisomer of the title compound was prepared according to the method described for I-32, but starting from the HCl salt of (S)-ethyl 2-aminopropanoate (11.0 g, 71.1 mmol). Yield 8.56 g, 27%.

Intermediate 34

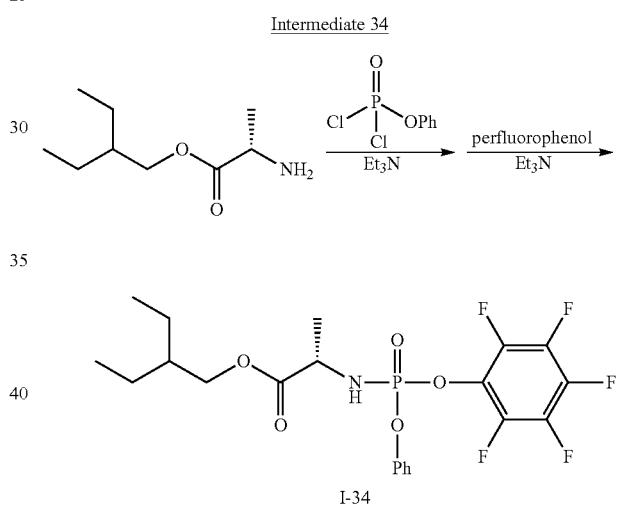

(2S)-2-ethylbutyl 2-(((perfluorophenoxy)(phenoxy)phosphoryl)amino)propanoate (I-34)

The pure phosphorus stereoisomer of the title compound was prepared according to the method described for I-32, but starting from the pTs salt of (S)-2-ethylbutyl 2-aminopropanoate (18.8 g, 54.4 mmol). Yield 27.0 g, 99%.

LC-MS 496.44 [M+H]$^+$.

Intermediate 35

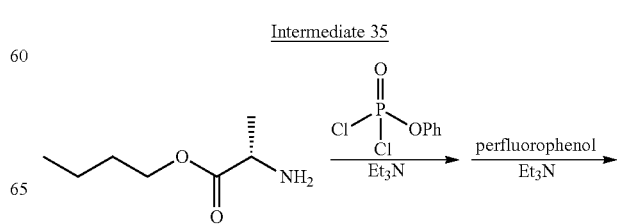

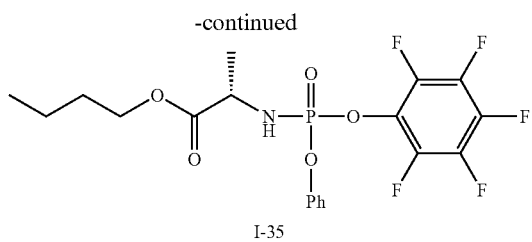

I-35

(2S)-butyl 2-(((perfluorophenoxy)(phenoxy)phosphoryl)amino)propanoate (I-35)

Phenyl dichlorophosphate (12.4 mL, 83.1 mmol) was added to a cooled (−20° C.) slurry of (S)-butyl 2-aminopropanoate (26.4 g, 83.1 mmol) in dichloromethane (200 mL). The mixture was stirred for 10 min then Et$_3$N (25.5 mL, 183 mmol) was added dropwise for 15 min. The mixture was stirred at −20° C. for 1 h then at 0° C. for 30 min. The mixture was kept cooled in an ice-bath and perfluorophenol (15.3 g, 0.08 mol) was added followed by a dropwise addition of Et$_3$N (11.6 mL, 0.08 mol). The mixture was stirred over night and slowly taken to 20° C. Diethyl ether was added and the mixture was filtered through Celite, concentrated and purified by column chromatography on silica gel eluted with petroleum ether/EtOAc (9:1→8:2). Appropriate fractions were pooled, concentrated and crystallized from petroleum ether EtOAc (9:1) which gave the pure phosphorus stereoisomer of the title compound as a white solid (2.23 g, 5.8%).

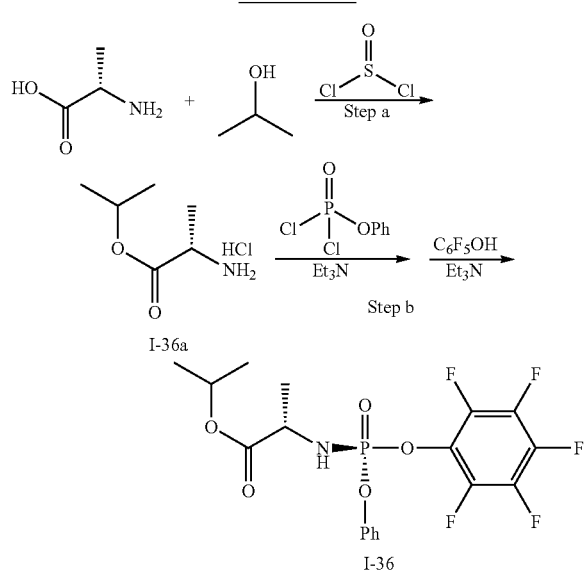

Step a) L-Alanine isopropylester hydrochloride (I-36a)

Thionylchloride (80.2 g, 0.674 mol, 1.5 eq) was added with cooling to 2-propanol (400 mL) at −7 to 0° C. over a period of 30 minutes, followed by addition of L-alanine (40.0 g, 0.449 mol) at 0° C. A flow indicator and a scrubber with a mixture of 27.65% sodium hydroxide (228 g) and water (225 g) were attached to the outlet. The reaction mixture was stirred at 67° C. for two hours, then at 70° C. for one hour and at 20-25° C. over night. The reaction mixture was distilled at 47-50° C. under reduced pressure (250-50 mBar) from a 60° C. bath. When the distillation became very slow, toluene (100 mL) was added to the residual oil, and the distillation at 48-51° C. under reduced pressure (150-50 mBar) from a 60° C. bath was continued until it became very slow. t-butylmethylether (tBME)(400 mL) was added to the residual oil, and the two-phase system was seeded under efficient stirring at 34-35° C. When crystallization was observed the mixture was cooled to 23° C. over a period of one hour, and the precipitate isolated by filtration. The filter cake was washed with tBME (100 mL) and dried to constant weight under reduced pressure without heating, which gave the title compound (67.7 g, 90%) as white solids.

Step b) (S)-Isopropyl 2-(((S)-(perfluorophenoxy)(phenoxy)phosphoryl)amino)propanoate (I-36)

Phenyl dichlorophosphate (62.88 g, 0.298 mol, 1.0 eq) was added under nitrogen to a solution of L-alanine isopropylester hydrochloride (50.0 g, 0.298 mol) in DCM (310 mL) at 0° C.—the addition was completed by wash with DCM (39 mL). The mixture was cooled and triethylamine (63.35 g, 0.626 mol, 2.1 eq) was added over a period of 70 minutes with cooling keeping the temperature not higher than −14° C., the addition was completed by wash with DCM (39 mL). The mixture was stirred for one hour at −15 to −20° C., then heated to −8° C. and a solution of pentafluorophenol (60.38 g, 0.328 mol, 1.1 eq) and triethylamine (33.19 g, 0.328 mol, 1.1 eq) in DCM (78 mL) was added over a period of 42 minutes with cooling keeping the temperature not higher than 0° C.—the addition was completed by wash with DCM (39 mL). The mixture was stirred for one hour at 0° C. and then over night at +5° C. The formed precipitate was removed by filtration, and the filter cake washed with DCM (95 mL). The combined filtrates were washed at 5° C. with water (2×190 mL). The organic phase was distilled at 32-38° C. at reduced pressure (650-600 mBar), and distillation was continued until a residual volume of approx. 170 mL partly crystallized mass was obtained. Ethyl acetate (385 mL) was added, and the resulting clear solution was distilled at 43-45° C. under reduced pressure (300-250 mBar). Distillation was continued until a residual volume of approx. 345 mL was obtained. The clear solution was cooled to 36° C., and crystallization is induced by addition of seed crystals of (S)-isopropyl 2-(((S)-(perfluorophenoxy)(phenoxy)phosphoryl)amino)propanoate (20 mg) prepared as described in J. Org. Chem., 2011, 76, 8311-8319. The mixture was cooled to 27° C. over a period of one hour, then n-heptane (770 mL) was added over a period of 47 minutes, and the mixture was stirred for an additional period of 37 minutes. Triethylamine (6.03 g, 0.2 eq) was added, and the mixture was stirred at 23-25° C. over night. The precipitate was isolated by filtration. The filter cake was washed with ethyl acetate:n-heptane (1:9, 80 mL) and dried to constant under reduced pressure (below 0.1 mBar) without heating, which gave the title compound (75.64 g, 56%) as a white crystalline material.

$^1$H NMR (CDCl$_3$, 300 MHz) δ 7.38-7.32 (m, 2H), 7.27-7.24 (m, 2H), 7.23-7.19 (m, 1H), 5.10-4.98 (m, 1H), 4.20-4.08 (m, 1H), 4.03-3.96 (m, 1H), 1.46 (dd, 7.2, 0.6 Hz, 3H), 1.26-1.23 (2xd, 6H);

$^{13}$CNMR (CDCl$_3$, 100 MHz) δ 172.7 (d, J=8.8 Hz), 150.4 (d, J=7.1 Hz), 143.4-143.0 (m), 141.0-140.2 (m), 140.0-139.8 (m), 137.6-137.2 (m), 136.8-136.2 (m), 130.0 (d,

J=0.82 Hz), 125.8 (d, J=1.4 Hz), 120.3 (d, J=5.0 Hz), 69.8, 50.6, (d, J=1.9 Hz), 21.8 (d, J=1.9 Hz), 21.2 (d, J=4.4 Hz);

The crystallization properties and NMR spectral data of the title compound were in agreement with published data (J. Org. Chem., 2011, 76, 8311-8319), thus confirming the S stereochemistry of the phosphorus atom of the title compound.

dissolved in EtOAc (300 mL), washed with water (50 mL), dried and the solvent was removed under reduced pressure. The obtained solid was triturated with 20% EtOAc in hexane, filtered, washed with hexane and dried to afford the title compound as a single diastereomer (3.0 g, 21%) as a solid.

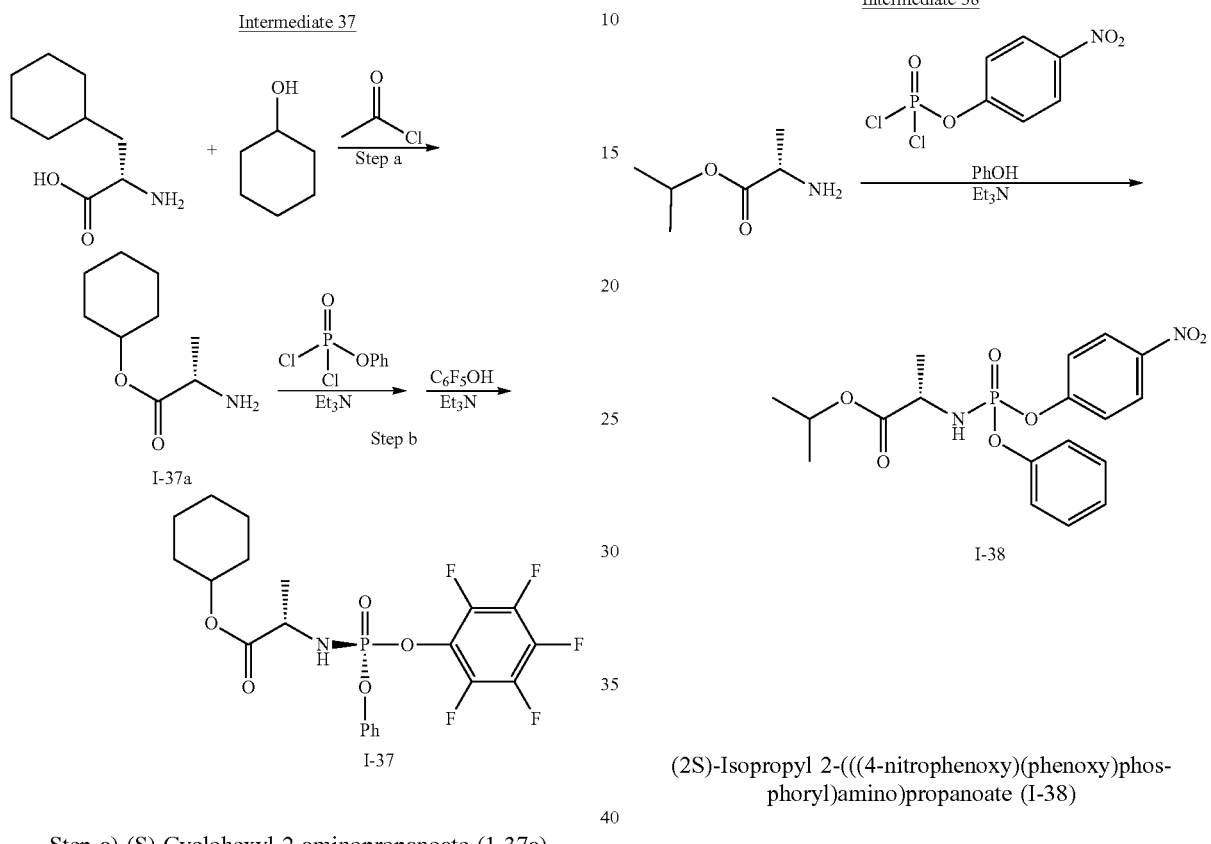

Step a) (S)-Cyclohexyl 2-aminopropanoate (I-37a)

Acetylchloride (4.2 mL, 59.3 mmol) was added drop-wise to a stirred solution of cyclohexanol (50 ml), followed by L-phenylalanine (4.0 g, 24.2 mmol). The reaction mixture was heated to 100° C. for 16 h, then concentrated under reduced pressure, triturated with diethyl ether/Hexane (1:1) and dried to afford the title compound (6 g, 88%) as white solid which was used in next step without further purification.

Step b) (S)-Cyclohexyl 2-(((S)-(perfluorophenoxy)(phenoxy)phosphoryl)amino)propanoate (I-37)

To a stirred solution of compound I-37a (7.0 g, 24.6 mmol) in dry DCM (42 mL) triethylamine (7.17 mL, 51.5 mmol) was drop wise added at −70° C. over 30 minutes, followed by addition of a solution of phenyl dichlorophosphate (5.15 g, 34.5 mmol) in dry DCM (21 mL) over 1 h. The reaction mixture was stirred at −70° C. for additional 30 min and then allowed to warm 0° C. over 2 h and stirred for 1 h. To this mixture was added a solution of pentafluorophenol (4.94 g, 26.8 mmol) and triethylamine (3.74 mL, 26.8 mmol) in dry DCM (28 mL) over 1 h. The mixture was allowed to stir at 0° C. for 4 h, and then left at 5° C. for 16 h. The reaction mixture was filtered and the filtrate was concentrated under reduced pressure. The crude solid was

(2S)-Isopropyl 2-(((4-nitrophenoxy)(phenoxy)phosphoryl)amino)propanoate (I-38)

To a stirred solution of 4-nitrophenyldichlorophosphate (5 g, 19.8 mmol) in dry DCM (40 ml) was added a solution of phenol (1.86 g, 19.8 mmol) and triethylamine (3 mL, 21.8 mmol) in dry DCM (50 mL) at −78° C. over a period of 30 min. The mixture was stirred at this temperature for 60 min, then transferred to another flask containing a solution of compound (S)-isopropyl 2-aminopropanoate (3.3 g, 19.8 mmol) in dry DCM (40 mL) at −5° C. over a period of 15 min. To this mixture was added a second portion of TEA (6 mL, 43.3 mmol) at −5° C. over a period of 20 min. The mixture was stirred at 0° C. for 3 h, then the solvent was removed under reduced pressure. The residue was taken in EtOAc (200 mL) and washed with water (50 mL), dried over $Na_2SO_4$ and the solvents were removed under reduced pressure to give the crude product as an oil, which was purified by column chromatography using 0-20% EtOAc/Hexane gradient and 230-400 mesh silica gel to give a mixture of diastereomers in about 1:1 ratio. The two diastereomers were separated by SFC which gave the title compound, Isomer 1 (1.5 g, 20%) and Isomer 2 (1.5 g, 18%) as solids.

The compounds listed in Table 1 were prepared and the diastereomers separated according to the procedure described for the preparation of Intermediate I-38, using the appropriate amino acid ester and phenol.

TABLE 1
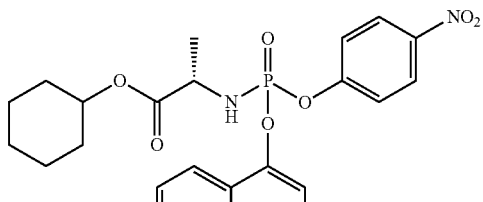
I-39, dia-1 & -2
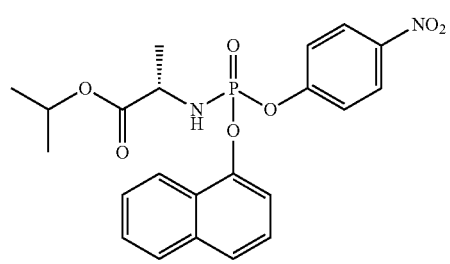
I-40, dia-1 & -2
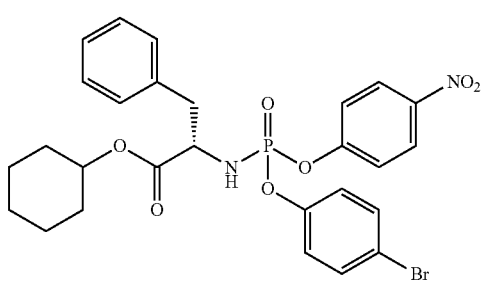
I-41, dia-1 & -2
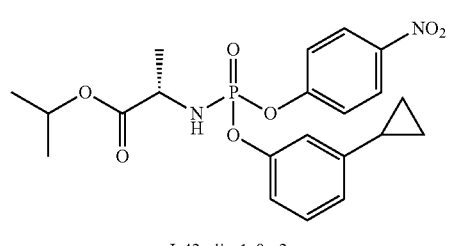
I-42, dia-1 & -2
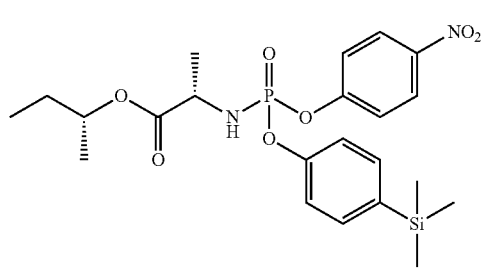
I-43, dia-1 & -2
TABLE 1-continued
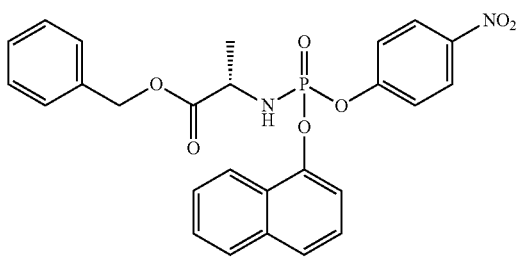
I-44, dia-1 & -2
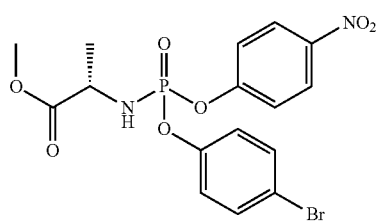
I-45, dia-1 & -2
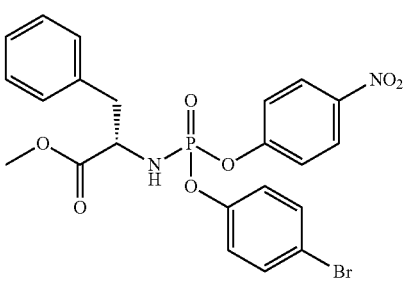
I-46, dia-1 & -2
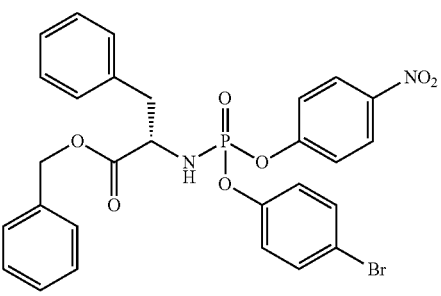
I-47, dia-1 & -2
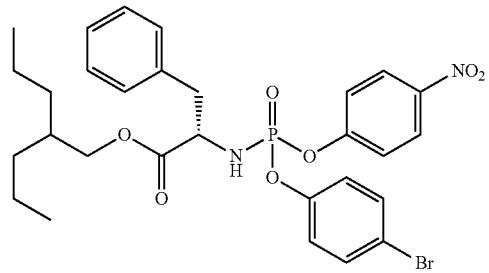
I-48,
4:1 mix of P-disastereomers TABLE 1-continued
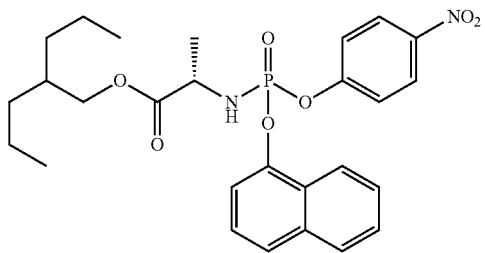
I-49, dia-1 & -2
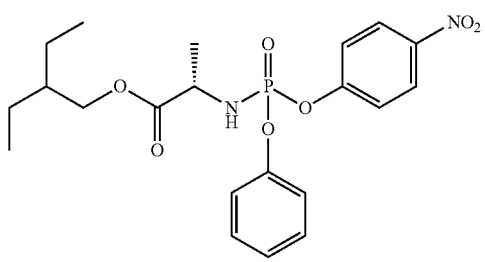
I-50, dia-1 & -2
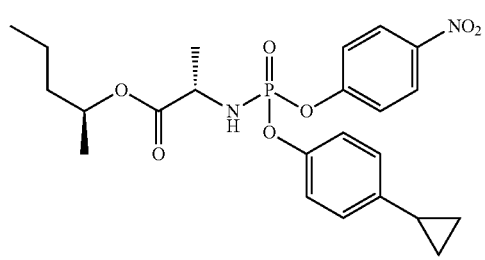
I-51, dia-1 & -2
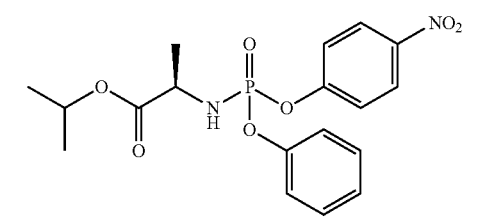
I-52, dia-1 & -2
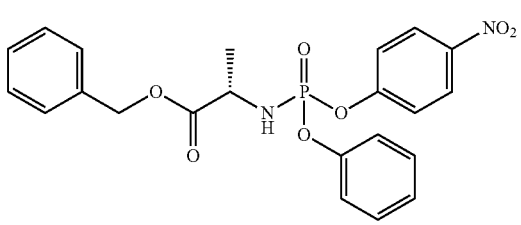
I-53, dia-1 & -2
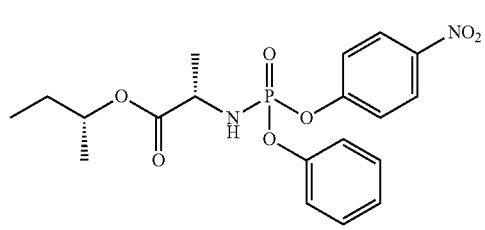
I-54, dia-1 & -2
TABLE 1-continued
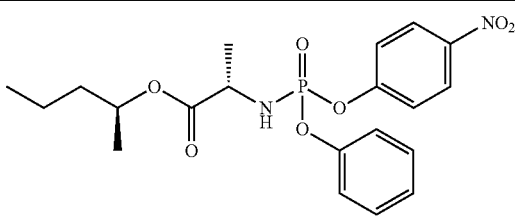
I-55, dia-1 & -2
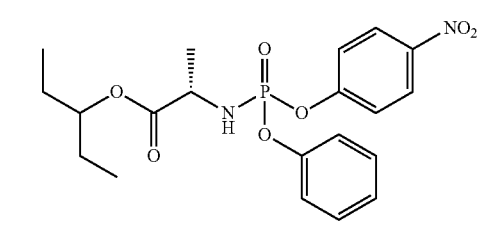
I-56, dia-1 & -2
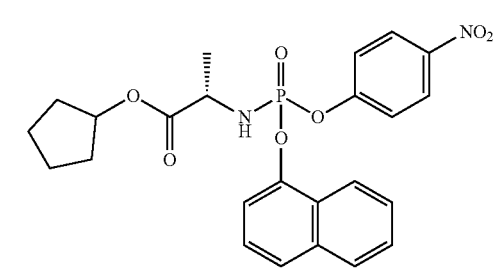
I-57, dia-1 & -2
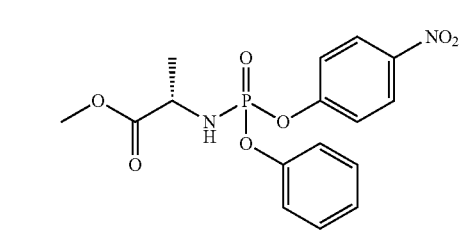
I-58, dia-1 & -2
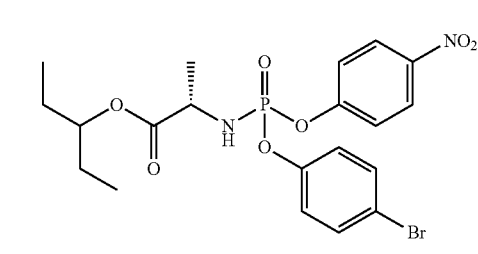
I-59, dia-1 & -2
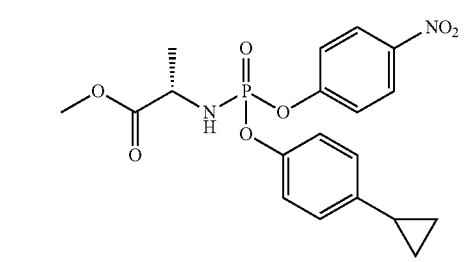
I-60, dia-1 & -2

Example 1

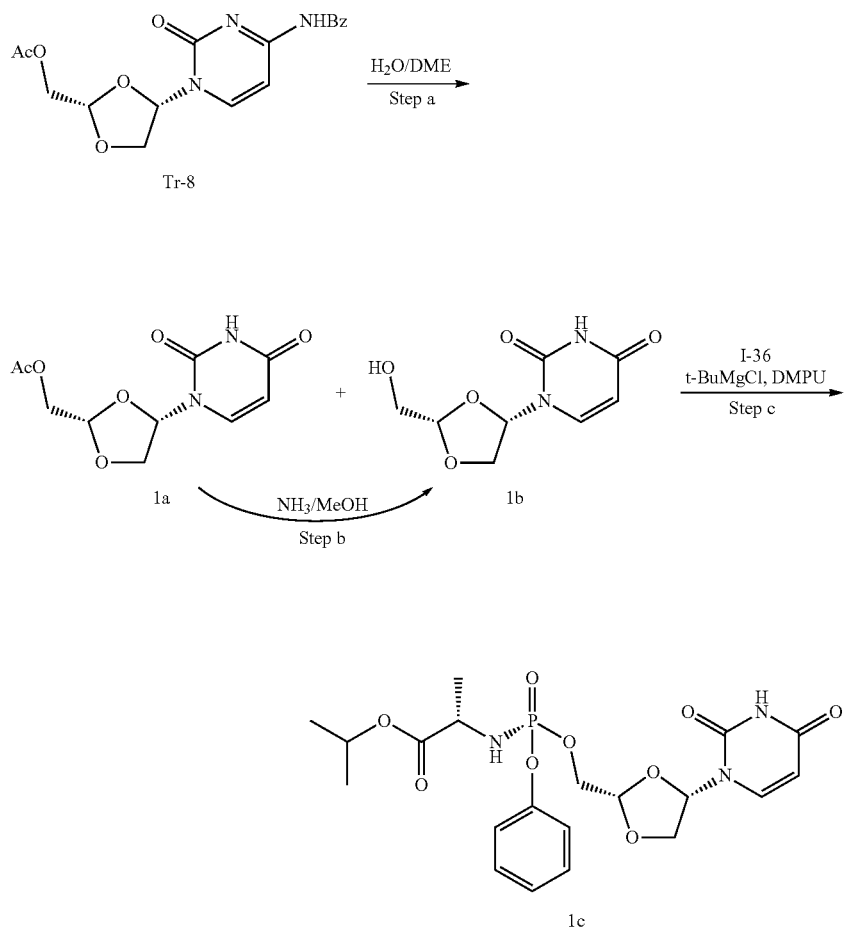

Step a) ((2S,4S)-4-(2,4-dioxo-3,4-dihydropyrimidin-1(2H)-yl)-1,3-dioxolan-2-yl)methyl acetate (1a)

A mixture of compound Tr-8 (0.15 g, 0.41 mmol), 1,2-dimethoxyethane (1.5 mL) and water (0.96 mL) were heated in the sealed tube at 125° C. for 48 h. After completion of the reaction (TLC), the reaction mixture was cooled to room temperature and solvents were removed under reduced pressure. The crude residue was purified by column chromatography on 230-400 silica as 3-7% MeOH/DCM gradient which gave compound 1a (0.08 g, 80%) as a solid and compound 1 b (0.02 g) as a solid.

Step b) 1-((2S,4S)-2-(hydroxymethyl)-1,3-dioxolan-4-yl)pyrimidine-2,4(1H,3H)-dione (1b)

Compound 1a (0.08 g, 0.31 mmol) in a saturated solution of $NH_3$ in MeOH (1.6 mL) was stirred in the sealed tube at room temperature for 4 h. After completion of the reaction (TLC), the solvents were removed under reduced pressure and the residue was purified by column chromatography on 60-120 silica using 5-7% MeOH/DCM to afford compound the title compound (0.06 g, 90%) as a solid.

Step c) (2S)-isopropyl 2-(((((2S,4S)-4-(2,4-dioxo-3,4-dihydropyrimidin-1(2H)-yl)-1,3-dioxolan-2-yl)methoxy)(phenoxy)phosphoryl)amino)propanoate (1c)

To a stirred solution of compound 1 b (60 mg, 0.28 mmol) in DMPU (0.6 mL), tert-butylmagnesiumchloride (0.57 mL, 0.98 mmol, 1.7 M in THF) was drop-wise added at −5° C. The mixture was stirred at −5° C. for 30 min, then at room temperature for 30 min. A solution of isopropyl ((perfluorophenoxy)(phenoxy)phosphoryl)-L-alaninate (0.25 g, 0.56 mmol) in dry THF (2.5 mL) was added at −5° C. and the reaction mixture was stirred at room temperature for 8 h. After completion of the reaction (TLC), water (15 mL) was added and the mixture was extracted with EtOAc (30 mL). The organic phase was washed with sat. sodium chloride solution (10 mL), dried ($Na_2SO_4$), filtered and concentrated, and the afforded crude was purified by column chromatography on 230-400 silica as 4-5% MeOH/DCM gradient which gave the title compound (55 mg, 38%) as a solid. MS (ES+) [484.0]$^+$.

$^1$H NMR (DMSO-$d_6$, 400 MHz) δ 1.15-1.20 (10H), 3.73-3.75 (1H), 4.11-4.27 (4H), 4.84-4.90 (1H), 5.14 (1H), 5.51-5.53 (1H), 6.06-6.12 (1H), 6.26-6.27 (1H), 7.17-7.23 (3H), 7.36-7.40 (2H), 7.57-7.60 (1H), 11.37 (1H).

Example 2

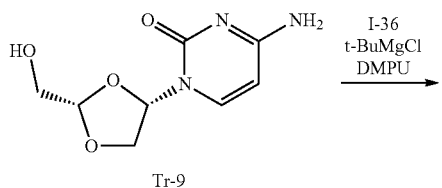

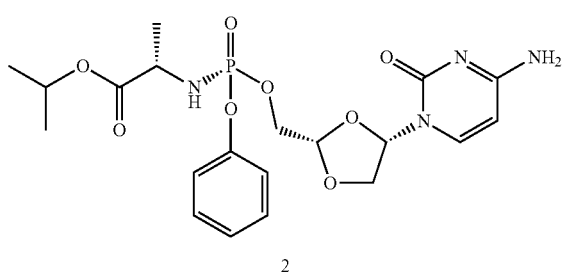

(2S)-Isopropyl 2-(((((2S,4S)-4-(4-amino-2-oxopy-rimidin-1(2H)-yl)-1,3-dioxolan-2-yl)methoxy)(phe-noxy)phosphoryl)amino)propanoate (2)

Troxacitabine (TR-9) (50 mg, 0.23 mmol) was reacted with the phosphorylating agent 1-36 (0.26 g, 0.58 mmol) according to the procedure described in Example 1 step c, which gave the title compound (30 mg, 26%) as a solid. MS (ES+) 483.34 [M+H]$^+$.

$^1$H NMR (DMSO-$d_6$, 400 MHz) δ 1.14-1.24 (9H), 3.32-3.38 (1H), 4.05-4.21 (4H), 4.84-4.26 (1H), 5.14 (1H), 5.68-5.70 (1H), 6.07-6.13 (1H), 6.23-6.25 (1H), 7.16-7.24 (5H), 7.34-7.39 (2H), 7.59-7.61 (1H).

Example 3

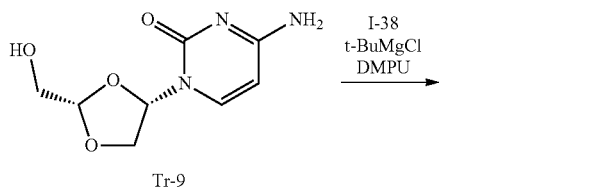

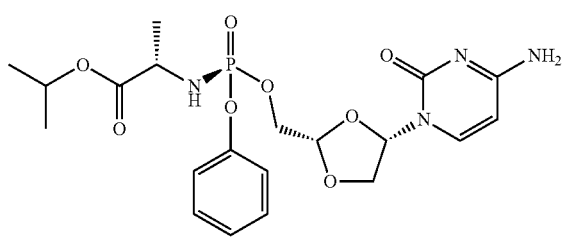

(2S)-Isopropyl 2-(((((2S,4S)-4-(4-amino-2-oxopy-rimidin-1(2H)-yl)-1,3-dioxolan-2-yl)methoxy)(phe-noxy)phosphoryl)amino)propanoate (3)

Troxacitabine (50 mg, 0.23 mmol) was reacted with the phosphorylating agent 1-38 (0.24 g, 0.58 mmol) according to the procedure described in Example 1 step c, which gave the title compound (40 mg, 35%) as a solid. MS (APCI) 481.0 [M−H]$^-$.

$^1$H NMR (DMSO-$d_6$, 400 MHz) δ 1.14-1.20 (9H), 3.76-3.77 (1H), 4.10-4.18 (2H), 4.22-4.25 (2H), 4.84-4.87 (1H), 5.17-5.186 (1H), 5.69-5.70 (1H), 6.03-6.08 (1H), 6.24-6.26 (1H), 7.17-7.25 (5H), 7.36-7.40 (2H), 7.62-7.64 (1H).

Example 4

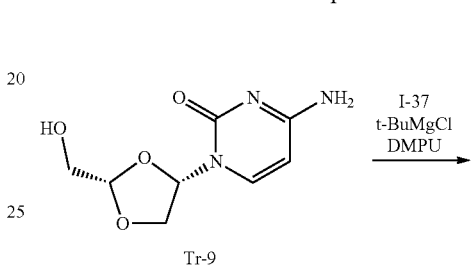

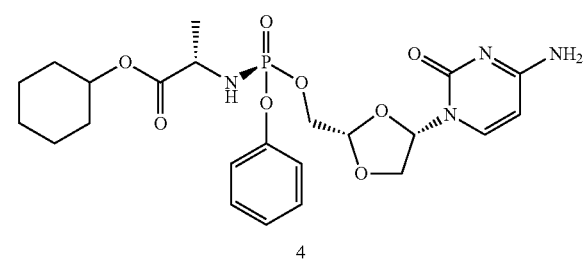

(2S)-Isopropyl 2-(((((2S,4S)-4-(4-amino-2-oxopy-rimidin-1(2H)-yl)-1,3-dioxolan-2-yl)methoxy)(phe-noxy)phosphoryl)amino)propanoate (4)

Troxacitabine (50 mg, 0.23 mmol) was reacted with the phosphorylating agent 1-37 (0.33 g, 0.58 mmol) according to the procedure described in Example 1 step c, which gave the title compound (30 mg, 22%) as a solid. MS (APCI) 599.47 [M+H]$^+$.

The compounds listed in TABLE 2 were prepared as pure diastereomers according to the procedure described in Example 1 step c using the appropriate intermediate, I-# dia-1 or I-# dia-2.

TABLE 2

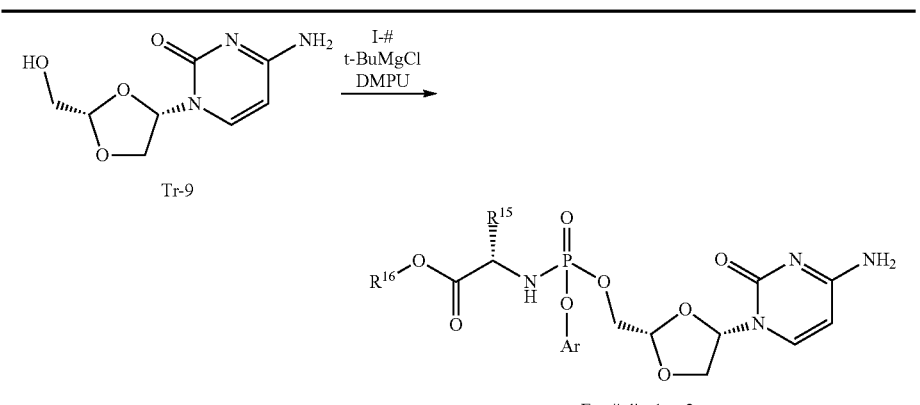

| Ex. | Interm. | R15 | R16 | Ar | diastereomer 1 Yield | diastereomer 1 MS [M + H]+ | diastereomer 2 Yield | diastereomer 2 MS [M + H]+ |
|---|---|---|---|---|---|---|---|---|
| 5 | I-40 | methyl | 2-propyl | 1-naphthyl | 25% | 533.40 | 33% | 533.36 |
| 6 | I-39 | methyl | cyclohexyl | 1-naphthyl | 19% | 573.35 | 22% | 573.2 |
| 7 | I-41 | benzyl | cyclohexyl | 4-Br-phenyl | 18% | na | 18% | na |
| 8 | I-6 | methyl | 2-propyl-pentyl | phenyl | 37% | 553.2 | 35% | 553.2 |
| 9 | I-44 | methyl | benzyl | 1-naphthyl | 25% | 581.2 | 30% | 581.2 |
| 10 | I-42 | methyl | 2-propyl | 2-cyclopropyl-phenyl | 34% | 523.2 | 27% | 523.2 |
| 11 | I-43 | methyl | 2-butyl | 4-(trimethyl-silyl)-phenyl | 37% | 569.2 | 37% | 569.2 |

Similarly, the compounds listed in TABLE 3 were prepared as pure diastereomers according to the procedure described in Example 1 step c using the appropriate intermediates.

TABLE 3

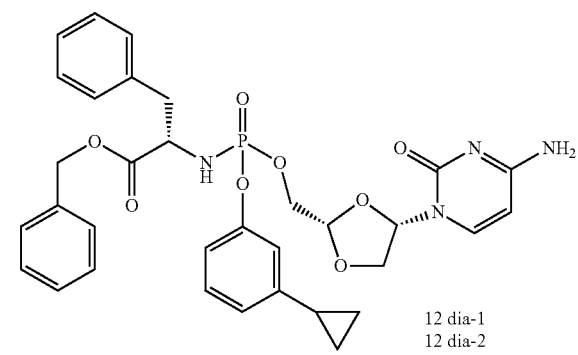 [SMILES: Nc1ccn([C@@H]2CO[C@H](COP(=O)(N[C@@H](Cc3ccccc3)C(=O)OCc3ccccc3)Oc3cccc(C4CC4)c3)O2)c(=O)n1]

12 dia-1
12 dia-2

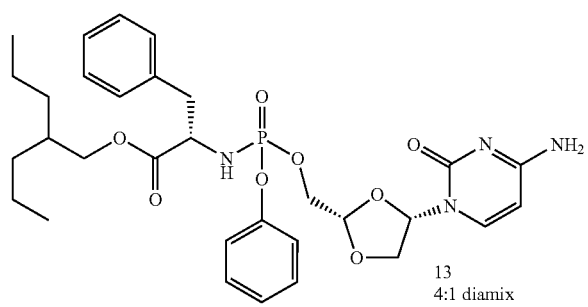 [SMILES: CCCC(CCC)COC(=O)[C@H](Cc1ccccc1)NP(=O)(OC[C@H]1OC[C@@H](n2ccc(N)nc2=O)O1)Oc1ccccc1]

13
4:1 diamix

TABLE 3-continued

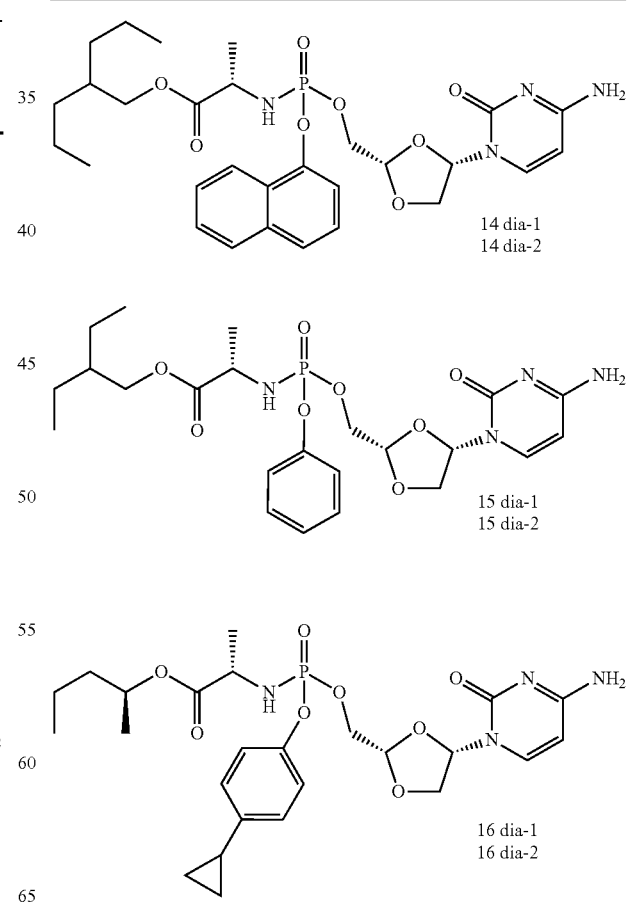

14 dia-1
14 dia-2

15 dia-1
15 dia-2

16 dia-1
16 dia-2

TABLE 3-continued
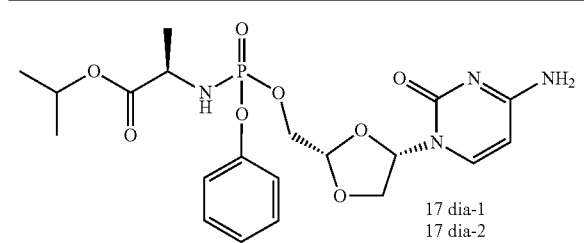
17 dia-1
17 dia-2
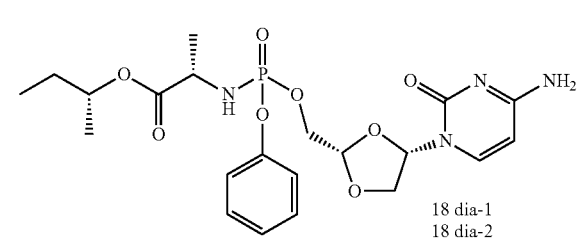 [SMILES: CC[C@@H](C)OC(=O)[C@H](C)NP(=O)(OC[C@H]1OC[C@@H](n2ccc(N)nc2=O)O1)Oc1ccccc1]
18 dia-1
18 dia-2
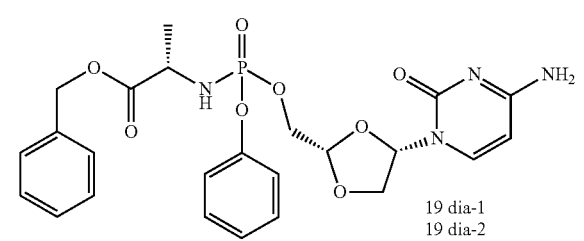 [SMILES: C[C@H](NP(=O)(OC[C@H]1OC[C@@H](n2ccc(N)nc2=O)O1)Oc1ccccc1)C(=O)OCc1ccccc1]
19 dia-1
19 dia-2
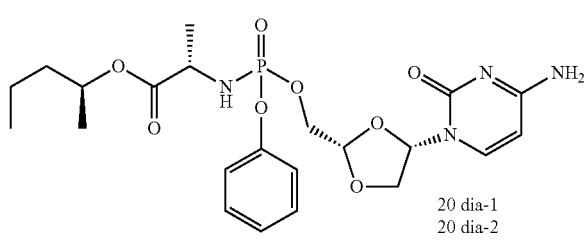 [SMILES: CCC[C@H](C)OC(=O)[C@H](C)NP(=O)(OC[C@H]1OC[C@@H](n2ccc(N)nc2=O)O1)Oc1ccccc1]
20 dia-1
20 dia-2
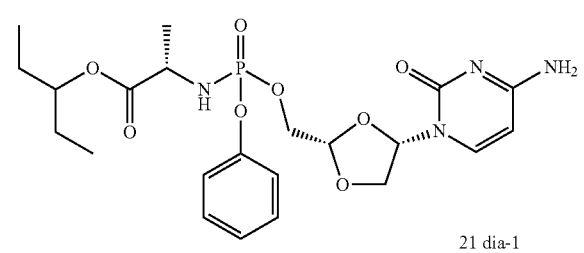
21 dia-1
21 dia-2
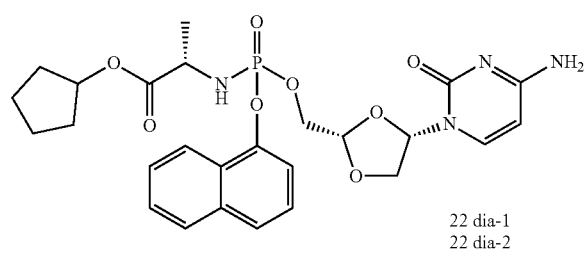 [SMILES: C[C@H](NP(=O)(OC[C@H]1OC[C@@H](n2ccc(N)nc2=O)O1)Oc1cccc2ccccc12)C(=O)OC1CCCC1]
22 dia-1
22 dia-2
TABLE 3-continued
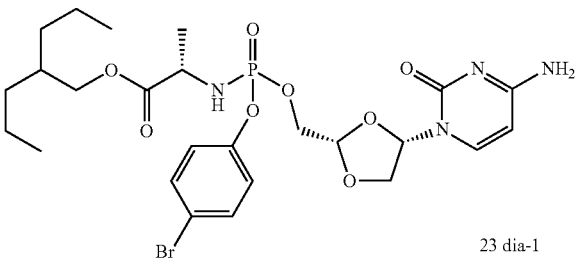
23 dia-1
23 dia-2
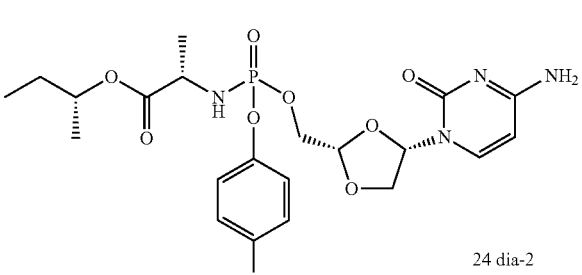
24 dia-2
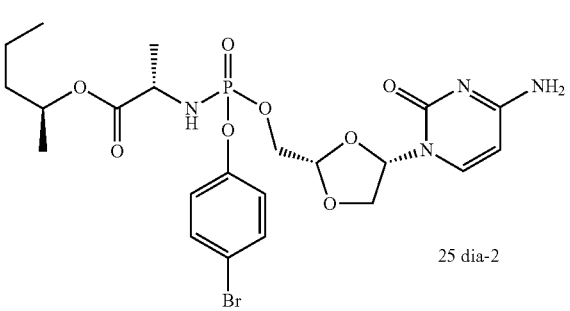 [SMILES: CCC[C@H](C)OC(=O)[C@H](C)NP(=O)(OC[C@H]1OC[C@@H](n2ccc(N)nc2=O)O1)Oc1ccc(Br)cc1]
25 dia-2
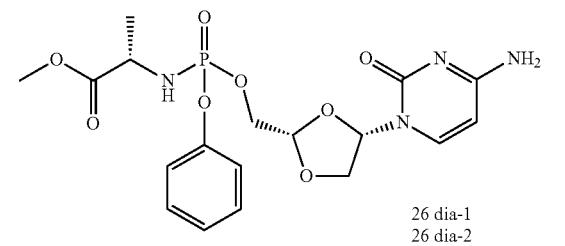 [SMILES: COC(=O)[C@H](C)NP(=O)(OC[C@H]1OC[C@@H](n2ccc(N)nc2=O)O1)Oc1ccccc1]
26 dia-1
26 dia-2
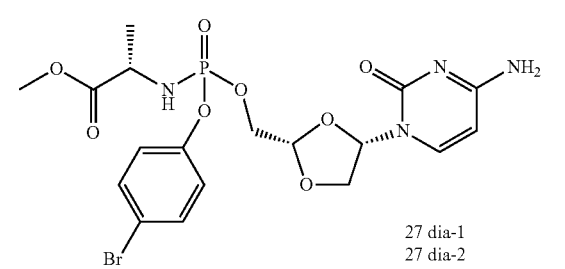 [SMILES: COC(=O)[C@H](C)NP(=O)(OC[C@H]1OC[C@@H](n2ccc(N)nc2=O)O1)Oc1ccc(Br)cc1]
27 dia-1
27 dia-2

TABLE 3-continued

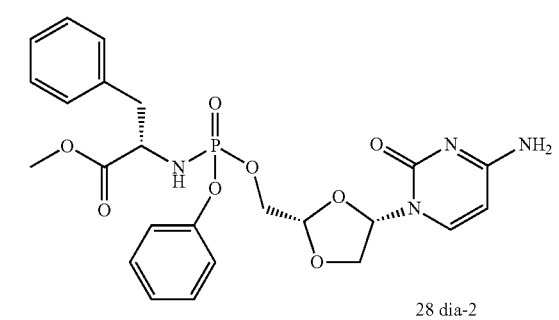 [SMILES: COC(=O)[C@H](Cc1ccccc1)NP(=O)(OC[C@H]1OC[C@@H](n2ccc(N)nc2=O)O1)Oc1ccccc1]

28 dia-2

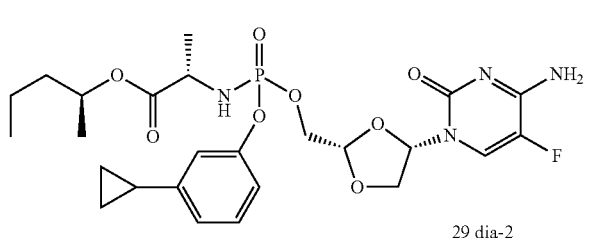 [SMILES: CCC[C@H](C)OC(=O)[C@H](C)NP(=O)(OC[C@H]1OC[C@@H](n2cc(F)c(N)nc2=O)O1)Oc1cccc(C2CC2)c1]

29 dia-2

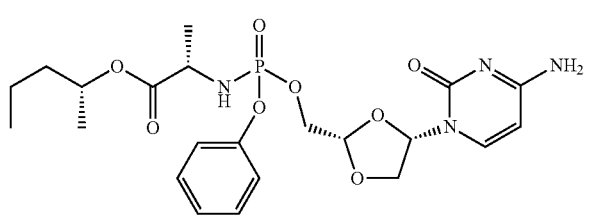

30 dia-2

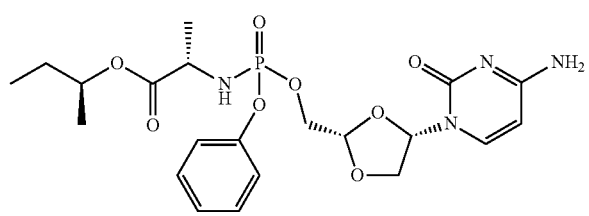

31 dia-2

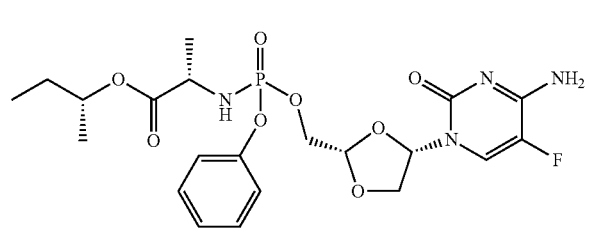

32 dia-2

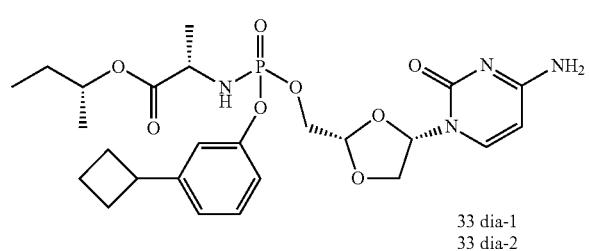 [SMILES: CC[C@@H](C)OC(=O)[C@H](C)NP(=O)(OC[C@H]1OC[C@@H](n2ccc(N)nc2=O)O1)Oc1cccc(C2CCC2)c1]

33 dia-1
33 dia-2

TABLE 3-continued

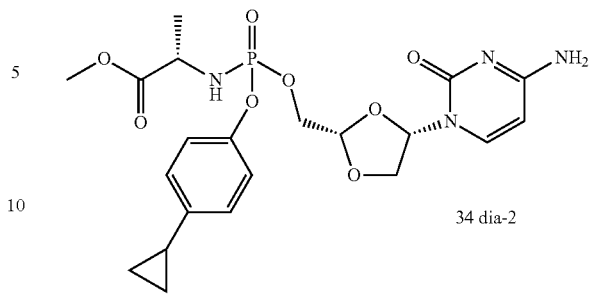

34 dia-2

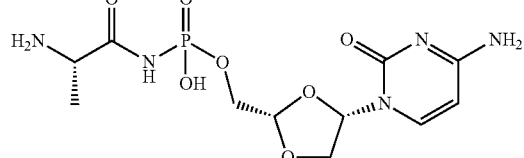

Comparative example

NMR and MS data were recorded for all exemplified compounds confirming their structures.

Example 35

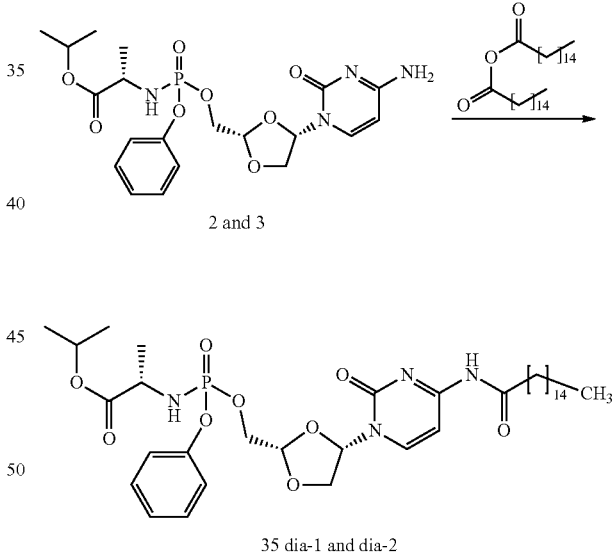

2 and 3

35 dia-1 and dia-2

(2S)-isopropyl 2-(((((2S,4S)-4-(2-oxo-4-palmitamidopyrimidin-1(2H)-yl)-1,3-dioxolan-2-yl)methoxy)(phenoxy)phosphoryl)amino)propanoate (35 dia1 & 35 dia-2)

Compound 2 and 3 were each acylated with palmitic anhydride according to the method described in WO2008/030373, which gave title compounds.

Example 36

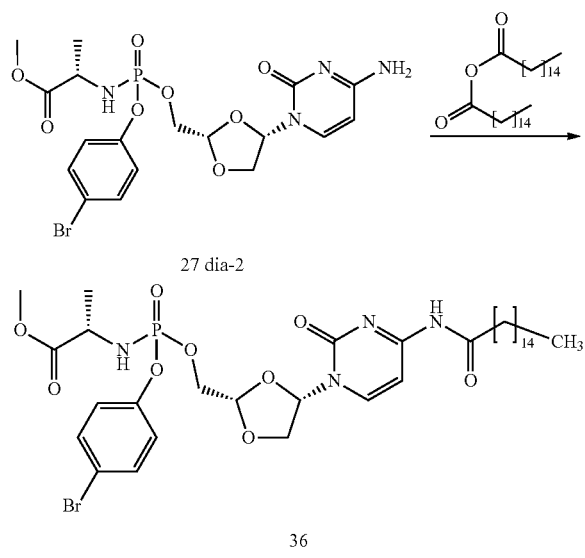

(2S)-methyl 2-(((((2S,4S)-4-(2-oxo-4-palmitami-dopyrimidin-1(2H)-yl)-1,3-dioxolan-2-yl)methoxy)(phenoxy)phosphoryl)amino)propanoate (36)

Compound 27 dia-2 was acylated with palmitic anhydride according to the method described in WO2008/030373, which gave title compound.

Comparative Example

Step a) (2S)-2-((bis(4-methoxyphenyl)(phenyl)methyl)amino)-N-(2-oxido-1,3,2-oxathiaphospholan-2-yl)propanamide To an ice-cold solution of (S)-2-((bis(4-methoxyphenyl)(phenyl)methyl)amino)propanamide (1.40 g, 3.58 mmol) and triethylamine (0.60 ml, 4.30 mol) in dichloromethane (8 ml) under nitrogen was added dropwise a solution of 2-chloro-1,3,2-oxathiaphospholane (0.542 g, 3.80 mmol). The reaction was allowed to attain room temperature and stirred over the week-end. The solution was cooled to 0° C. and a solution of (tert-butylperoxy)trimethylsilane (1.16 g, 7.17 mmol) in heptane was added slowly. The reaction mixture was stirred for 90 min, then concentrated in vacuum. The residue was suspended in ethyl acetate (10 mL), hydrochloride salts were removed by filtration and the solvent was removed in vacuum. The residue was dissolved in dry acetonitrile (10 mL) and the resulting solution used in the following step without further purification. Quantitative yield and 80% purity based on $^{31}$P-NMR were assumed.

Step b) ((2S,4S)-4-(4-amino-2-oxopyrimidin-1(2H)-yl)-1,3-dioxolan-2-yl)methyl hydrogen ((S)-2-((bis(4-methoxyphenyl)(phenyl)methyl)amino)pro-panoyl)phosphoramidate DMAP (229 mg, 1.88 mmol) was added under nitrogen to a solution of Compound Tr-9 (100 mg, 0.469 mmol) in dry pyridine (5 mL), followed by slow addition of a solution of (2S)-2-((bis(4-methoxyphenyl)(phenyl)methyl)amino)-N-(2-oxo-1,3,2-oxathia pholanyl)propanamide (361 mg, 0.563 mmol) in dry acetonitrile (2 mL). The resulting solution was stirred at RT under nitrogen for 46 h, then concentrated. The residue was purified by preparative HPLC on a Gemini-NX 5m C18 (100×30 mm) using a gradient from 20% B to 80% B in 17 min and a flow of 35 mL/min.

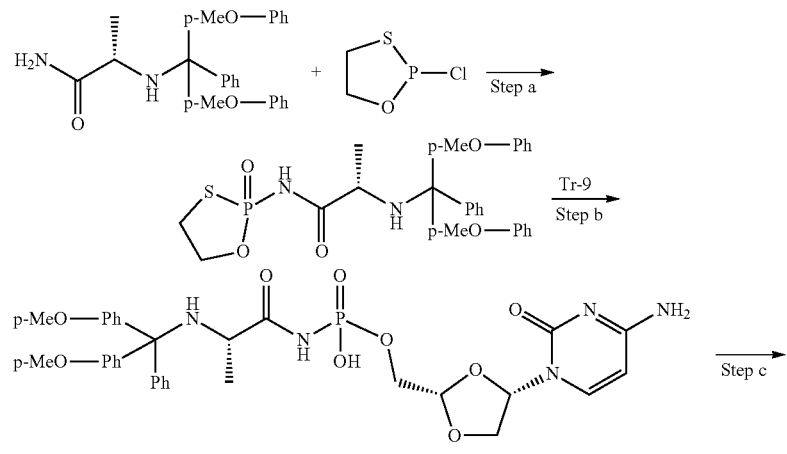

Comp. Ex.

Solvent A: 95% water, 5% acetonitrile (10 mM in ammonium acetate); Solvent B: 10% water, 90% acetonitrile (10 mM in ammonium acetate). Fractions containing the product were combined and freeze dried which gave the title compound (80 mg, 26%). MS (ES+) 664.26 [M+H]+.

Step c) ((2S,4S)-4-(4-amino-2-oxopyrimidin-1(2H)-yl)-1,3-dioxolan-2-yl)methyl hydrogen ((S)-2-aminopropanoyl)phosphoramidate Water (50 mL) was added to a solution of the compound from the previous step (80.5 mg, 0.121 mmol) in dichloromethane followed by addition of acetic acid (500 mL). The solution was stirred at rt for 12 min, then TFA (75 mL) was added and the resulting solution was stirred at RT for 5 min, diluted with toluene (10 mL), concentrated to dryness and dried under vacuum. The residue was taken into water containing 10% acetonitrile (10 mL) and washed with tert-butyl methyl ether containing 10% hexanes (2×10 mL). The aqueous layer was collected and freeze dried overnight to yield the desired product as the bis-TFA salt (80 mg) having a purity of ~75% according to LC-MS. The obtained residue was further purified by preparative HPLC on a Hypercarb (21.2×100 mm, I=271 nm), using a gradient from 0% to 35% acetonitrile in water. Fractions containing the product were combined and freeze dried. MS (ES+) 364.10 [M+H]+. The structure was confirmed by $^1$H and $^{13}$C NMR.

NMR data for a selection of the exemplified compounds:
Compound 8 dia-1
$^1$H NMR (DMSO-$d_6$, 400 MHz) δ 0.81-0.84 (6H), 1.20-1.22 (11H), 1.59 (1H), 3.82-3.97 (3H), 4.08-4.16 (2H), 4.22-4.23 (2H), 5.16 (1H), 5.67-5.69 (1H), 6.05-6.10 (1H), 6.23-6.24 (1H), 7.16-7.23 (m, 5H), 7.34-7.38 (m, 2H), 7.60-7.62 (m, 1H).
Compound 8 dia-2
$^1$H NMR (DMSO-$d_6$, 400 MHz) δ 0.81-0.84 (6H), 1.22-1.27 (11H), 1.57 (1H), 3.81-3.89 (2H), 3.95-3.98 (1H), 4.05-4.07 (1H), 4.10-4.20 (3H), 5.128 (1H), 5.68-5.69 (1H), 6.13-6.14 (1H), 6.22-6.24 (1H), 7.16-7.21 (5H), 7.34-7.38 (2H), 7.58-7.60 (1H).
Compound 9 dia-1
$^{31}$P NMR (DMSO-$d_6$) δ 4.354.
$^1$H NMR (DMSO-$d_6$, 400 MHz) δ 1.24-1.26 (3H), 3.98-4.01 (1H), 4.12-4.14 (2H), 4.27-4.29 (2H), 5.00-5.08 (2H), 5.16-5.18 (1H), 5.64-5.66 (2H), 6.25-6.27 (1H), 6.34 (1H), 7.17-7.22 (2H), 7.31-7.33 (5H), 7.45-7.46 (2H), 7.55-7.59 (2H), 7.63-7.64 (1H), 7.74-7.77 (1H), 7.95-7.97 (1H), 8.08-8.11 (1H).
Compound 9 dia-2
$^{31}$P NMR (DMSO-$d_6$) δ 4.159.
$^1$H NMR (DMSO-$d_6$, 400 MHz) δ 1.25-1.26 (3H), 3.97-4.01 (1H), 4.08-4.16 (2H), 4.23-4.29 (2H), 5.04-5.16 (3H), 5.65-5.66 (1H), 6.26 (1H), 6.36-6.42 (1H), 7.17-7.24 (2H), 7.326 (5H), 7.41-7.49 (2H), 7.57-7.64 (3H), 7.74-7.76 (1H), 7.95-7.97 (1H), 8.10-8.12 (1H).
Compound 11-dia-1
$^1$H NMR (DMSO-$d_6$, 400 MHz) δ 0.23 (9H), 0.78-0.82 (3H), 1.08-1.12 (3H), 1.20-1.22 (3H), 1.44-1.49 (2H), 3.77-3.79 (1H), 4.09-4.23 (4H), 4.67-4.72 (1H), 5.16-5.16 (1H), 5.69-5.70 (1H), 6.04-6.10 (1H), 6.23-6.25 (1H), 7.15-7.24 (4H), 7.48-7.50 (2H), 7.61-7.63 (1H).
Compound 11 dia-2
$^1$H NMR (DMSO-$d_6$, 400 MHz) δ 0.22-0.24 (9H), 0.78-0.82 (3H), 1.10-1.11 (3H), 1.22-1.24 (3H), 1.46-1.50 (2H), 4.05-4.07 (1H), 4.11-4.22 (4H), 4.70-4.71 (1H), 5.14 (1H), 5.69-5.71 (1H), 6.07-6.11 (1H), 6.23-6.25 (1H), 7.16-7.24 (4H), 7.49-7.51 (2H), 7.60-7.62 (1H).

For a prodrug to be liver targeted, a correct processing of the prodrug is crucial. The prodrug should be stable in intestinal fluid, and processed in the liver by liver enzymes in a first pass metabolism to form the monophosphate. The formed monophosphate is then to be anabolized by cellular kinases in the hepatocytes to the active triphosphate species. Additionally, the anti-cancer drug should be toxic to proliferating cells. Suitable methods to evaluate compounds for these properties are, for example, as set out below.

Stability in Human Intestinal S9 Fraction (HIS9) and in Human Liver S9 Fraction (HLS9), Stock solutions of each test compound (10 mM) were prepared in DMSO and stored at −20° C. Prior to the start of the experiment, the test compounds were diluted to 500 μM in 50% acetonitrile in water. The reaction mixture was prepared in a total volume of 250 μL containing 5 mM $MgCl_2$, 1 mM NADPH and 5 μM test compound in 50 mM potassium phosphate buffer (pH 7.4). The reaction was initiated by addition of human liver or intestinal S9 fraction with a final concentration of 0.4 mg protein/mL (Xeno Tech). The reaction mixture was incubated on an orbital shaker at 37° C. At the desired time points (0, 10, 30 and 60 minutes) aliquots of 50 μL were taken and the reaction was stopped by mixing with 150 μL acetonitrile containing internal standard. Standard solutions of each test compound were prepared from the 500 μM solution by diluting the solution to a final concentration of 5 μM in boiled human S9 (0.4 mg protein/mL), 5 mM $MgCl_2$ and 50 mM potassium phosphate buffer (pH 7.4). The standards and samples were kept on ice for 30 min then centrifuged at 3 000 g for 20 minutes at 10° C., there after 10 μL of supernatant was mixed with 200 μL 50% acetonitrile in water. 0.5 μM of each test compound in 50% acetonitrile in water was injected into the LC/MS-MS to determine the daughter ion, declustring potential (DP), collision energy (CE) and collision cell exit potential (CXP) in order to develop a LC/MS-MS method. The compounds were separated using a C18 column with a QTRAP5500 system. The mobile phase consisted of solvent A (98% water, 2% acetonitrile, 0.1% acetic acid or 10 mM ammonium acetate) and solvent B (80% acetonitrile, 20% water, 0.1% acetic acid or 10 mM ammonium acetate). Elution of the compounds was performed by using a gradient of solvent B from 0% to 100%. 5 μL of standard points and samples were injected for analysis with QTRAP5500.

The amount of parent compound was determined on the basis of the peak area for each time point compared to standard which was set to 5 μM. Intrinsic clearance ($CL_{int}$) and half-life ($t_{1/2}$) were determined from the disappearance curves of the test compound using Excel software.

Cell Cytotoxicity Assays

Cells were seeded 24 hours prior to compound addition. Each test compound (serially diluted from 100 μM) was added to Huh7 (1.5×10$^4$ cells/well) or HepG2 (1.5×10$^4$ cells/well), and allowed to incubate for 5 days at 37° C. A medium only control was used to determine the minimum absorbance value and an untreated cell value. At the end of the growth period, XTT dye from Polysciences Europe GmbH was added to each well. The absorbance at 450 nm with a reference wavelength of 600 nM was read with a Sunrise (Tecan) using the medium only control wells as blanks. The 50% inhibition value ($CC_{50}$) was determined by comparing the degree of inhibition (compared to cell control) plotted against compound concentration. Results from the dilution series were fitted to a sigmoidal dose-response curve.

Compounds of the invention were evaluated in these assays to assess the stability in human intestinal S9 fraction (HIS9) and human liver S9 fraction (HLS9), and for Cell Cytotoxicity in HUH7, HEP3B and HEPG2 cells. The results are summarised in TABLE B1.

TABLE B1

| Example | HUH7 $CC_{50}$ (μM) | HEP3B $CC_{50}$ (μM) | HEPG2 $CC_{50}$ (μM) | $CL_{int}$ Liver S9 (μL/min/mg) | $CL_{int}$ Intestinal S9 (μL/min/mg) |
|---|---|---|---|---|---|
| 1 | >100 | na | >100 | 12 | 6 |
| 2 | 1.75 | na | 0.248 | 13 | 6 |
| 3 | 3.28 | na | 0.371 | 8 | 6 |
| 4 | 12.0 | na | 0.936 | 84 | 123 |
| 4 dia-2 | 1.55 | na | 0.093 | 38 | 18 |
| 5 dia-1 | 0.465 | na | 0.107 | 32 | 21 |
| 5 dia-2 | 0.602 | na | 0.114 | 31 | 13 |
| 6 dia-1 | 0.258 | na | 0.092 | 91 | 36 |
| 6 dia-2 | 0.316 | na | 0.048 | 61 | 25 |
| 7 dia-1 | 1.02 | na | 0.24 | 148 | 147 |
| 7 dia-2 | 0.134 | na | 0.058 | 60 | 27 |
| 8 dia-1 | 0.123 | na | 0.007 | 130 | 86 |
| 8 dia-2 | 0.074 | 0.035 | 0.017 | 143 | 25 |
| 9 dia-1 | 0.164 | na | 0.023 | 133 | 171 |
| 9 dia-2 | 0.158 | na | 0.016 | 94 | 127 |
| 10 dia-1 | 0.392 | na | 0.062 | 26 | 12 |
| 10 dia-2 | 0.556 | na | 0.051 | 22 | 14 |
| 11 dia-1 | 0.026 | 0.018 | 0.054 | 51 | 6 |
| 11 dia-2 | na | 0.031 | 0.054 | 81 | 28 |
| 12 dia-1 | 4.33 | na | 0.481 | 182 | 300 |
| 12 dia-2 | 5.02 | na | 1.09 | 97 | 300 |
| 13 diamix 4:1 | 0.663 | na | 0.163 | 85 | 27 |
| 14 dia-1 | 0.216 | na | 0.016 | 88 | 30 |
| 14 dia-2 | 0.200 | na | 0.012 | 159 | 59 |
| 15 dia-1 | 0.025 | na | 0.037 | 167 | 87 |
| 15 dia-2 | 0.026 | na | 0.019 | 95 | 36 |
| 16 dia-1 | 1.20 | 0.106 | 0.151 | 50 | 8 |
| 16 dia-2 | 0.152 | 0.053 | 0.130 | 59 | 8 |
| 17 dia-1 | 50.0 | na | 50.0 | 6 | 6 |
| 17 dia-2 | 50.0 | na | 50.0 | 6 | 6 |
| 18 dia-1 | 0.461 | 0.228 | 0.248 | 21 | 6 |
| 18 dia-2 | 0.076 | 0.113 | 0.065 | 30 | 7 |
| 19 dia-1 | 0.091 | na | 0.018 | 19 | 26 |
| 19 dia-2 | 0.071 | 0.058 | 0.014 | 24 | 17 |
| 20 dia-1 | 0.216 | na | 0.074 | 45 | 21 |
| 20 dia-2 | 0.073 | 0.078 | 0.060 | 25 | 6 |
| 21 dia-1 | 0.574 | na | 0.163 | 61 | 29 |
| 21 dia-2 | 0.070 | na | 0.048 | 22 | 10 |
| 22 dia-1 | 0.033 | na | 0.012 | 49 | 52 |
| 22 dia-2 | 0.040 | na | 0.011 | 43 | 34 |
| 23 dia-1 | na | 0.01 | 0.0086 | 186 | 32 |
| 23 dia-2 | na | na | na | 300 | 20 |
| 24 dia-1 | na | na | na | na | na |
| 24 dia-2 | na | na | na | na | na |
| 25 dia-1 | na | na | na | na | na |
| 25 dia-2 | na | na | na | na | na |
| 26 dia-1 | na | 4.34 | 1.21 | 7 | 6 |
| 26 dia-2 | 4.73 | 4.02 | 1.06 | 10 | 6 |
| Troxacitabine | 0.646 | 0.279 | 0.218 | na | na |
| 27 dia-1 | 1.44 | na | 0.151 | 38 | 11 |
| 27 dia-2 | 1.02 | 0.348 | 0.223 | 57 | 6 |
| 28 dia-2 | 15.6 | na | 2.72 | 20 | 40 |
| 29 dia-2 | 0.495 | 0.075 | na | 36 | 18 |
| 30 dia-2 | na | na | na | 120 | 11 |
| 31 dia-2 | na | na | na | 8 | 6 |
| 32 dia-2 | na | na | na | 27 | 8 |
| 33 dia-1 | na | na | na | 180 | 27 |
| 33 dia-2 | na | na | na | 230 | 75 |
| 34 dia-2 | 0.524 | 0.210 | 0.236 | 64 | 6 |
| 35 dia-2 | 0.011 | na | 0.007 | 34 | 51 |
| 36 | 0.009 | 0.019 | na | na | | na = not availablena

Triphosphate Formation Assay

Each compound was tested in triplicates in the assay.

Fresh human plated hepatocytes (Biopredic, France) in 12-well plates were used. Each well was plated with 0.76× $10^6$ cells and incubated with a 10 μM DMSO solution of compound (0.1% DMSO) in 1 mL incubation medium in a $CO_2$ incubator at 37° C. for 8 hours. Huh7 cells grown in DMEM with antibiotics and 10% fetal calf serum were seeded in 12 well plates, 2×$10^6$ cells/well. After 24 hrs 1 mL of 10 μM compound in medium was added and the cells were incubated another 6-8 hrs.

The incubation was stopped by washing each well with 1 mL ice cold Hank's balanced solution, pH 7.2 twice, followed by addition of 0.5 mL ice cold 70% methanol. Immediately after the addition of methanol, the cell-layer was detached from the bottom of the well by a cell scraper and sucked up and down 5-6 times with an automatic pipet. The cell suspension was transferred to a glass vial and stored over night at −20° C.

The samples, each consisting of various levels of prodrug, free nucleoside, and mono-, di- and triphosphate were then vortexed and centrifuged at 10° C. for 10 minutes, at 14000 rpm in an Eppendorf centrifuge 5417R. The supernatants were transferred to 2 mL glass vials with insert and subjected to bioanalysis as follows:

An internal standard (Indinavir) was added to each sample and the samples (10 μL injection volume) were analysed on a two column system coupled to a QTRAP 5000 mass spectrometer. The two column system consisted of two binary pumps, X and Y, two switching valves and an autosampler. The two HPLC columns used were a Synergy POLAR-RP 50*4.6 mm, 4 μm particles and a BioBasic AX 50*2.1 mm 5 μm particles. The LC flow rates were 0.4-0.6 mL/min mUmin (the higher flow rate were used in the recondition step).

The HPLC mobile phases for the POLAR-RP column consisted of 10 mmol/L ammonium acetate in 2% acetonitrile (mobile phase A) and 10 mmol/L ammonium acetate in 90% acetonitrile (mobile phase B) and for the BioBasic AX column 10 mmol/L ammonium acetate in 2% acetonitrile (mobile phase C) and 1% ammonium hydroxide in 2% acetonitrile (mobile phase D). The HPLC gradient for pump Y started at 0% mobile phase B and was held for 2 min. During loading phase, the mobile phase went through the POLAR-RP and BioBasic AX column, and prodrug, nucleoside and internal standard were trapped on the POLAR-RP column; whereas the nucleotides (mono-, di- and triphosphates) eluted on to the BioBasic AX column and were trapped there.

In the next step, the flow was switched from the POLAR-RP column to the MS and the mobile phase C switched from pump X to the BioBasic AX column. The compounds on the POLAR-RP column were eluted with a gradient from 0% B up to 100% B in about two minutes and analyzed in positive or negative mode using the multiple reaction monitoring mode (MRM).

In the last step the flow from the BioBasic AX column was switched to the MS and the phosphates were eluted with a of about 7 minutes gradient up 50% D, and analyzed in positive or negative mode using MRM. During the last step both columns are reconditioned.

Triphosphate concentration for each compound was then determined by comparison with standard curves which were made by analysis of standard samples with known concentrations of triphosphate. The standards were run in the same matrices as the test samples. Due to variations in phosphorylation levels between hepatocyte donors, an internal reference compound is required in each run of the assay in order to enable ranking the results from different runs to each other.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All documents referred to herein, including patents and patent applications, are incorporated by reference in their entirety.

The invention claimed is:

1. A compound represented by formula Ia:

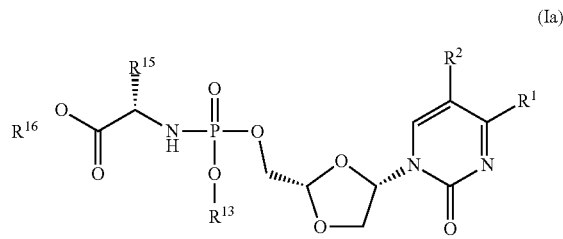

wherein:
$R^1$ is $OR^{11}$, or $NR^5R^{5'}$;
$R^2$ is F;
$R^5$ is H, $C_1$-$C_6$alkyl, OH, C(=O)$R^6$, OC(=O)$R^6$ or OC(=O)O$R^6$;
$R^{5'}$ is H or $C_1$-$C_6$alkyl;
$R^6$ is $C_1$-$C_{22}$alkyl or $C_3$-$C_7$cycloalkyl;
$R^{11}$ is H or $C_1$-$C_6$alkyl;
$R^{13}$ is H, phenyl, pyridyl, benzyl, indolyl or naphthyl wherein the phenyl, pyridyl, benzyl, indolyl and naphthyl is optionally substituted with 1, 2 or 3 $R^{22}$;
$R^{15}$ is $C_1$-$C_3$ alkyl;
$R^{16}$ is H, $C_1$-$C_{10}$alkyl, $C_2$-$C_{10}$alkenyl, $C_3$-$C_7$cycloalkyl, $C_3$-$C_7$cycloalkyl$C_1$-$C_3$alkyl, benzyl, or phenyl, any of which is optionally substituted with 1, 2 or 3 groups, each independently selected from halo, $OR^{18}$ and $N(R^{18})_2$;
each $R^{18}$ is independently H, $C_1$-$C_6$alkyl, $C_1$-$C_6$haloalkyl or $C_3$-$C_7$cycloalkyl;
each $R^{22}$ is independently selected from halo, $C_1$-$C_6$alkyl, $C_2$-$C_6$alkenyl, $C_1$-$C_6$haloalkyl, $C_1$-$C_6$alkoxy, $C_1$-$C_6$haloalkoxy, phenyl, hydroxy$C_1$-$C_6$alkyl, $C_3$-$C_6$cycloalkyl, $C_1$-$C_6$alkylcarbonyl, $C_3$-$C_6$cycloalkylcarbonyl, carboxy$C_1$-$C_6$alkyl, hydroxy, amino CN, and $NO_2$, or any two $R^{22}$ groups attached to adjacent ring carbon atoms can combine to form —O—(C$R^{23}R^{23'}$)$_{1-6}$—O—;
$R^{23}$ and $R^{23'}$ are independently H or $C_1$-$C_3$alkyl;
or a pharmaceutically acceptable salt thereof.

2. The compound according to claim 1, wherein $R^1$ is $NH_2$ or NHC(=O)$C_1$-$C_6$alkyl.

3. A compound according to claim 1, wherein $R^1$ is $NH_2$.

4. A compound according to claim 1, wherein $R^{15}$ is methyl.

5. A compound according to claim 1, wherein $R^{16}$ is $C_3$-$C_{10}$alkyl.

6. A compound according to claim 1, wherein $R^{16}$ is 2-propylpentyl or 2-ethylbutyl.

7. A compound according to claim 1, wherein $R^{16}$ is benzyl.

8. A compound according to claim 1, wherein $R^{16}$ is $C_3$-$C_7$cycloalky.

9. A compound according to claim 1, wherein $R^{13}$ is phenyl or naphthyl, any of which is optionally substituted with one or two $R^{22}$.

10. A compound according to claim 9, wherein $R^{13}$ is phenyl.

11. A compound according to claim 7, wherein $R^{16}$ is cyclopentyl or cyclohexyl.

12. A compound according to claim 1, with the formula

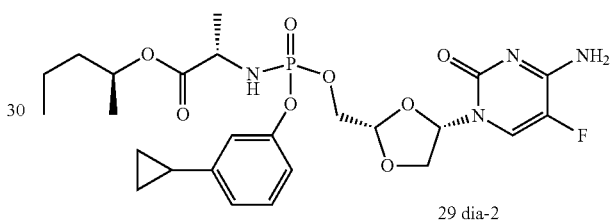

29 dia-2 or a pharmaceutically acceptable salt thereof.

13. A compound according to claim 1 with the formula

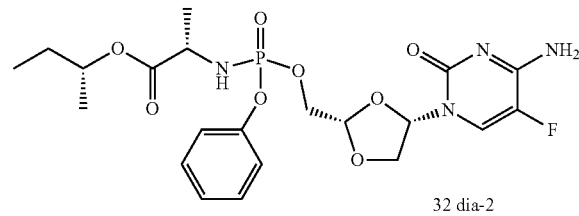 [SMILES: CC[C@@H](C)OC(=O)[C@H](C)NP(=O)(OC[C@H]1OC[C@@H](n2cc(F)c(N)nc2=O)O1)Oc1ccccc1]

32 dia-2 or a pharmaceutically acceptable salt thereof.

* * * * *